(12) United States Patent
Hsieh et al.

(10) Patent No.: US 8,138,194 B2
(45) Date of Patent: Mar. 20, 2012

(54) FUSED BICYCLIC PYRIMIDINE COMPOUNDS AS AURORA KINASE INHIBITORS

(75) Inventors: Hsing-Pang Hsieh, Miaoli County (TW); Selvaraj Mohane Coumar, Pondicherry (IN); Tsu-An Hsu, Taipei (TW); Su-Ying Wu, Miaoli County (TW); Yu-Sheng Chao, Monmouth Junction, NJ (US)

(73) Assignee: National Health Research Institutes, Miaoli County (TW)

( * ) Notice: Subject to any disclaimer, the term of this patent is extended or adjusted under 35 U.S.C. 154(b) by 226 days.

(21) Appl. No.: 12/428,044

(22) Filed: Apr. 22, 2009

(65) Prior Publication Data

US 2009/0275533 A1    Nov. 5, 2009

Related U.S. Application Data

(60) Provisional application No. 61/049,063, filed on Apr. 30, 2008.

(51) Int. Cl.
- A01N 43/90 (2006.01)
- A61K 31/519 (2006.01)
- A01N 43/54 (2006.01)
- A61K 31/505 (2006.01)
- C07D 487/00 (2006.01)
- C07D 491/00 (2006.01)

(52) U.S. Cl. ............... 514/260.1; 514/267; 544/250; 544/280

(58) Field of Classification Search .............. None
See application file for complete search history.

(56) References Cited

U.S. PATENT DOCUMENTS

| | | |
|---|---|---|
| 2004/0053908 A1 | 3/2004 | Funahashi et al. |
| 2004/0259888 A1 | 12/2004 | Bischoff et al. |
| 2005/0004142 A1 | 1/2005 | Adams et al. |
| 2005/0153989 A1 | 7/2005 | Grotzfeld et al. |
| 2005/0165029 A1 | 7/2005 | Patel et al. |
| 2005/0227992 A1 | 10/2005 | Hurley et al. |
| 2006/0035908 A1* | 2/2006 | Lew et al. ............ 514/260.1 |
| 2006/0040961 A1 | 2/2006 | Buchanan et al. |
| 2007/0027166 A1 | 2/2007 | Oslob et al. |

FOREIGN PATENT DOCUMENTS

| | | |
|---|---|---|
| DE | 10141212 | 3/2003 |
| EP | 447891 | * 3/1991 |
| WO | WO0232872 | * 4/2002 |
| WO | WO03/018589 | 3/2003 |
| WO | WO03/022852 | 3/2003 |
| WO | WO2005/067546 | 7/2005 |
| WO | WO2005/092896 | 10/2005 |
| WO | WO2006/004658 | 1/2006 |
| WO | WO2006/036266 | 4/2006 |
| WO | WO2007/013964 | 2/2007 |
| WO | 2007/053343 | 5/2007 |

OTHER PUBLICATIONS

Dorwald F. A. Side Reactions in Organic Synthesis, 2005, Wiley: VCH, Weinheim p. IX of Preface.*
Monge, et. al., Archiv der Pharmazie (Weinheim, Germany) (1993), 326(11), 879-85.*

* cited by examiner

*Primary Examiner* — Jeffrey Murray
(74) *Attorney, Agent, or Firm* — Occhiuti Rohlicek & Tsao LLP

(57) ABSTRACT

Fused bicyclic pyrimidine compounds of formula (I):

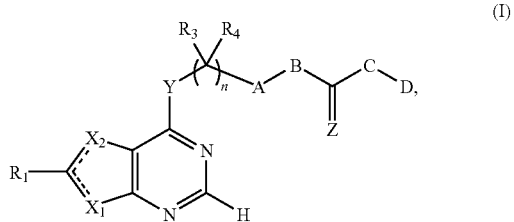

wherein $R_1$, $R_3$, $R_4$, $X_1$, $X_2$, Y, Z, A, B, C, D, n, and the two ═ bonds are defined herein. Also disclosed are a method for inhibiting Aurora kinase activity and a method for treating cancer with these compounds.

34 Claims, No Drawings

FUSED BICYCLIC PYRIMIDINE COMPOUNDS AS AURORA KINASE INHIBITORS

CROSS-REFERENCE TO RELATED APPLICATION

This application claims the benefit of the priority pursuant to 35 U.S.C. §119(e) of U.S. Provisional Patent Application No. 61/049,063, filed Apr. 30, 2008. The content of the prior application is incorporated herein by its entirety.

BACKGROUND

Protein kinases play important roles in cellular signal pathways that regulate various cell functions such as differentiation, proliferation, migration and apoptosis. Deregulation of protein kinases is implicated in a number of diseases including cancer. Thus protein kinases are attractive therapeutic targets in cancer treatment.

Aurora kinases, belonging to the serine/threonine subclass of kinases, are involved in the regulation of mitosis. Three isoforms A, B and C are known. Aurora A is involved in centrosome maturation and separation, bi-polar spindle assembly and mitotic entry; Aurora B and C are essential for accurate chromosome segregation and cytokinesis. The deregulated Aurora kinase activity has been linked to genetic instability, defects in centrosome function, spindle assembly, chromosome alignment, and cytokinesis, all of which can lead to tumorigenesis. For example, both Aurora A and B levels are up-regulated in various cancers, including breast and colorectal cancers. Thus, it is of great interest to develop Aurora kinase inhibitors as anti-cancer drugs.

SUMMARY

This invention is based on the discovery that certain fused bicyclic pyrimidine compounds can be used to inhibit activity of Aurora kinase (e.g., Aurora A, Aurora B, and or Aurora C), which allows these compounds to be applied in treating Aurora kinase mediated disorders such as cancer.

In one aspect, this invention relates to a furanopyrimidine or pyrrolopyrimidine compound of formula (I):

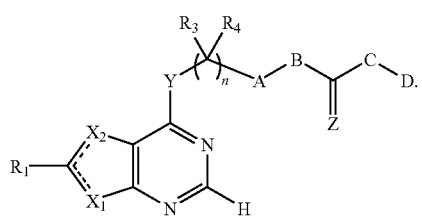

In formula (I), one of the two ═══bonds is a single bond and the other is a double bond; $X_1$ is O or $NR_a$ and $X_2$ is $CR_2$, or $X_1$ is $CR_2$ and $X_2$ is O or $NR_a$, in which $R_a$ is H, alkyl, alkenyl, alkynyl, aryl, or heteroaryl; each of Y and Z, independently, is O, S, or $NR_b$, in which $R_b$ is H, alkyl, alkenyl, alkynyl, aryl, heteroaryl, cycloalkyl, cycloalkenyl, heterocycloalkyl, heterocycloalkenyl, cyano, or $NO_2$; each of $R_1$ and $R_2$, independently, is H, alkyl, alkenyl, alkynyl, aryl, heteroaryl, cycloalkyl, cycloalkenyl, heterocycloalkyl, heterocycloalkenyl, halo, cyano, nitro, $OR_c$, $OC(O)R_c$, $C(O)R_c$, $C(O)OR_c$, $C(O)NR_cR_d$, $NR_cR_d$, $NHC(O)R_c$, $NHC(O)NR_cR_d$, $NHC(S)R_c$, $NHC(O)OR_c$, $SO_3R_c$, or $SO_2NR_cR_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl; or $R_1$ and $R_2$, together with the carbon atoms to which they are bonded, are cycloalkenyl, heterocycloalkenyl, aryl, or heteroaryl; each of $R_3$ and $R_4$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl; A is arylene or heteroarylene; B is O, S or $NR_e$, in which $R_e$ is H, alkyl, alkenyl, or alkynyl; C is O, S, alkylene, or $NR_f$, in which $R_f$ is H, alkyl, alkenyl, or alkynyl; or B and C, together with the carbon atom to which they are bonded, are heterocycloalkyl or heterocycloalkenyl; D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl, or heteroaryl; and n is 0, 1, 2, 3, or 4.

One subset of the above-described furanopyrimidine or pyrrolopyrimidine compounds includes those in which $X_1$ is O or NH and $X_2$ is $CR_2$. In these compounds, $R_1$ can be H, alkyl, alkynyl, aryl (e.g., phenyl optionally substituted with hydroxy or alkoxy), or heteroaryl; $R_2$ can be H, alkyl, alkynyl, halo, aryl (e.g., phenyl optionally substituted with hydroxy, alkoxy, or acylamino), or heteroaryl; each of $R_3$ and $R_4$ can be H; Y can be NH; Z can be O; A can be phenyl; each of B and C can be NH; D can be alkyl, aryl, heteroaryl, or cycloalkyl; or n can be 2.

Another subset of the furanopyrimidine or pyrrolopyrimidine compounds includes those in which $R_1$ is H, alkyl, alkynyl, aryl, or heteroaryl. In these compounds, $R_1$ can be phenyl optionally substituted with hydroxy or alkoxy; $R_2$ can be H, alkyl, alkynyl, halo, aryl (e.g., phenyl optionally substituted with hydroxy, alkoxy, or acylamino), or heteroaryl; each of $R_3$ and $R_4$ can be H; Y can be NH; Z can be O; A can be phenyl; each of B and C can be NH; D can be alkyl, aryl, heteroaryl, or cycloalkyl; or n can be 2.

Yet another subset of the furanopyrimidine or pyrrolopyrimidine compounds includes those in which Z is O and each of B and C is NH. In these compounds, $R_1$ can be H, alkyl, alkynyl, aryl (e.g., phenyl optionally substituted with hydroxy or alkoxy), or heteroaryl; $R_2$ can be H, alkyl, alkynyl, halo, aryl (e.g., phenyl optionally substituted with hydroxy, alkoxy, or acylamino), or heteroaryl; each of $R_3$ and $R_4$ can be H; Y can be NH; Z can be O; A can be phenyl; each of B and C can be NH; D can be alkyl, aryl, heteroaryl, or cycloalkyl; or n can be 2.

Still another two subsets of the furanopyrimidine or pyrrolopyrimidine compounds include those in which $X_1$ is $CR_2$ and $X_2$ is O or NH and those in which $R_1$ and $R_2$, together with the carbon atoms to which they are bonded, are cycloalkenyl, heterocycloalkenyl, aryl, or heteroaryl.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_{10}$). Examples of alkylene include, but are not limited to, methylene and ethylene. The term "alkenyl" refers to a straight or branched monovalent or bivalent hydrocarbon containing 2-20 carbon atoms (e.g., $C_2$-$C_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., $C_2$-$C_{10}$) and one or more triple bonds. Examples of alkynyl include, but are not limited to, ethynyl, ethynylene, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent or bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, and cyclooctyl. The term "cycloalkenyl" refers to a monovalent or bivalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent or bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, alkylamino, aryl, heteroaryl, alkylene, arylene, and heteroarylene mentioned above include both substituted and unsubstituted moieties. Possible substituents on alkylamino, cycloalkyl, heterocycloalkyl, cycloalkenyl, heterocycloalkenyl, aryl, arylene, heteroaryl, and heteroarylene include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino (RC(O)NR'—, in which each of R and R', independently, can be H, alkyl, alkenyl, alkynyl, cycloalkyl, cycloalkenyl, heterocycloalkyl, heterocycloalkenyl, aryl, or heteroaryl), aminoacyl (NRR'C(O)—), aminothioacyl, amidino, mercapto, amido (NRR'C(O)—), thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention relates to a thienopyrimidine compound of formula (I):

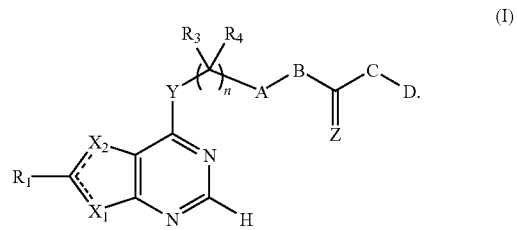

In formula (I), one of the two ═══bonds is a single bond and the other is a double bond; $X_1$ is S and $X_2$ is $CR_2$, or $X_1$ is $CR_2$ and $X_2$ is S; each of Y and Z, independently, is O, S, or $NR_b$, in which $R_b$ is H, alkyl, alkenyl, alkynyl, aryl, heteroaryl, cycloalkyl, cycloalkenyl, heterocycloalkyl, heterocycloalkenyl, or cyano; each of $R_1$ and $R_2$, independently, is alkynyl, aryl, heteroaryl, $NR_cR_d$, $NHC(O)R_c$, $NHC(O)NR_cR_d$, or $NHC(S)R_c$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl; or $R_1$ and $R_2$, together with the carbon atoms to which they are bonded, are cycloalkenyl, heterocycloalkenyl, aryl, or heteroaryl; each of $R_3$ and $R_4$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl; A is arylene or heteroarylene; B is O, S or $NR_e$, in which $R_e$ is H, alkyl, alkenyl, or alkynyl; C is O, S, alkylene, or $NR_f$, in which $R_f$ is H, alkyl, alkenyl, or alkynyl; or B and C, together with the carbon atom to which they are bonded, are heterocycloalkyl or heterocycloalkenyl; D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl, or heteroaryl; and n is 0, 1, 2, 3, or 4.

One subset of the above-described thienopyrimidine compounds includes those in which $X_1$ is S and $X_2$ is $CR_2$. In these compounds, $R_1$ and $R_2$, together with the carbon atoms to which they are bonded, can be cycloalkenyl (e.g., cyclohexenyl), heterocycloalkenyl, aryl, or heteroaryl; each of $R_3$ and $R_4$ can be H; Y can be NH; Z can be O; A can be phenyl; each of B and C can be NH; D can be alkyl, aryl, heteroaryl, or cycloalkyl; or n can be 2.

Another subset of the thienopyrimidine compounds includes those in which Z is O and each of B and C is NH. In these compounds, one of $R_1$ and $R_2$ can be alkynyl optionally substituted with alkyl, alkylamino, or amido, and the other can be aryl or heteroaryl.

The fused bicyclic pyrimidine compounds described above (i.e., furanopyrimidine pyrrolopyrimidine, and thienopyrimidine compounds of formula (I)) include the compounds themselves, as well as their salts, their solvates, and their prodrugs, if applicable. A salt, for example, can be formed between an anion and a positively charged group (e.g., amino) on a fused bicyclic pyrimidine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a fused bicyclic pyrimidine compound. Suitable cations include sodium ion, potassium ion, magnesium ion, calcium ion, and an ammonium cation such as tetramethylammonium ion. The fused bicyclic pyrimidine compounds also include those salts containing quaternary nitrogen atoms. Examples of prodrugs include esters and other pharmaceutically acceptable derivatives, which, upon administration to a subject, are capable of providing active fused bicyclic pyrimidine compounds.

In still another aspect, this invention relates to a method of inhibiting Aurora kinase activity by contacting a cell expressing Aurora kinase with an effective amount of one or more of the fused bicyclic pyrimidine compounds described above. The cell can be a tumor cell or a cell that over-expresses Aurora kinase.

In yet another aspect, this invention relates to a method of treating an Aurora kinase mediated disorder such as cancer by administering to a subject in need thereof an effective amount of one or more of the fused bicyclic pyrimidine compounds described above.

Also within the scope of this invention is a pharmaceutical composition containing one or more of the above-described fused bicyclic pyrimidine compounds for use in treating caner, as well as this therapeutic use and use of the compounds for the manufacture of a medicament for treating cancer.

The details of one or more embodiments of the invention are set forth in the description below. Other features, objects, and advantages of the invention will be apparent from the description and from the claims.

DETAILED DESCRIPTION

Shown below are exemplary compounds of this invention:

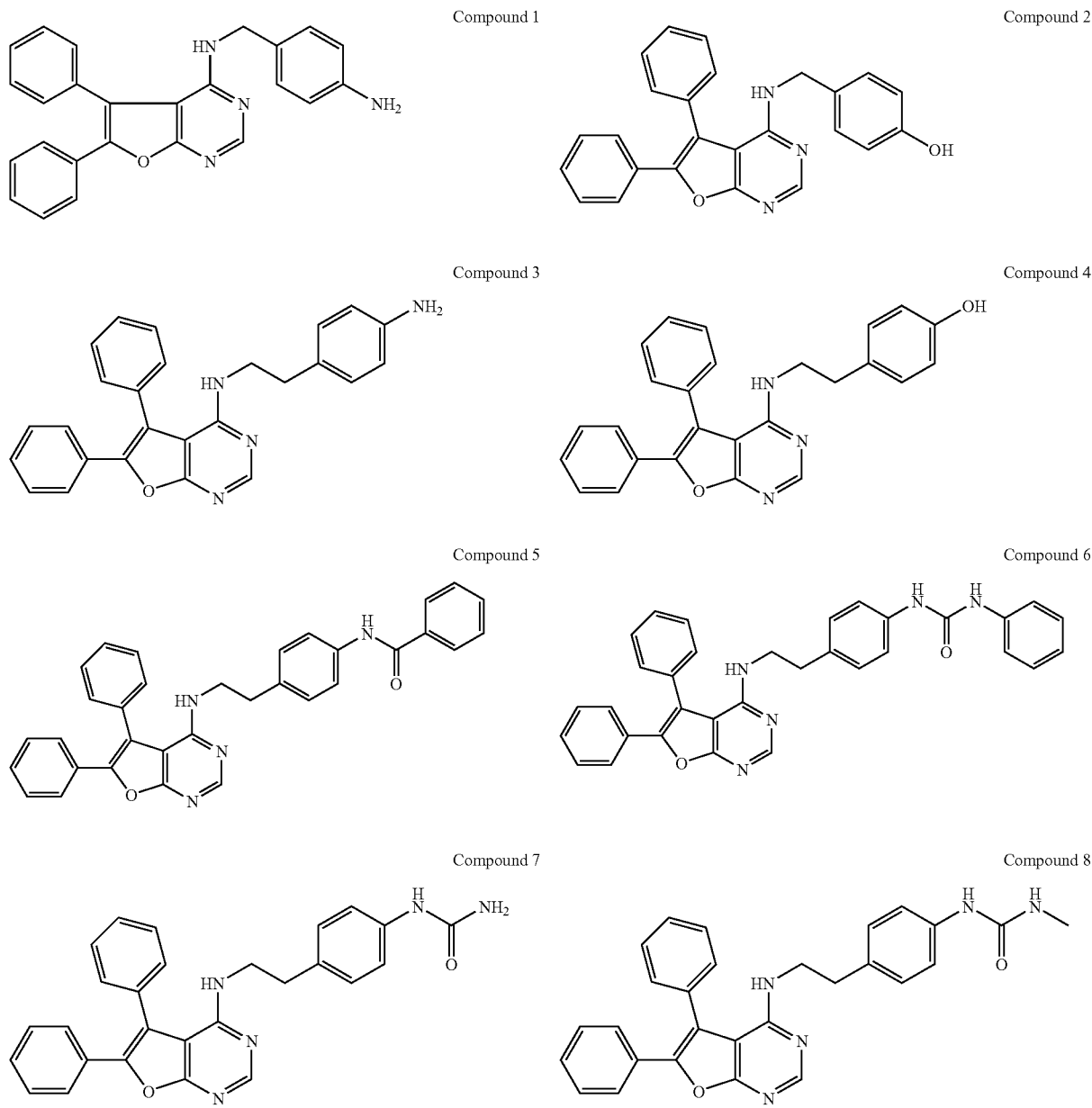

-continued
Compound 9
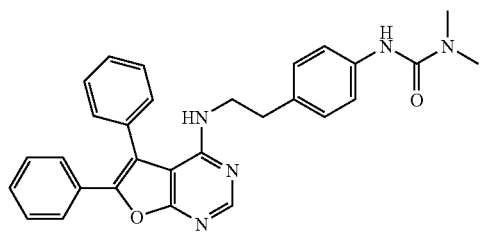
Compound 10
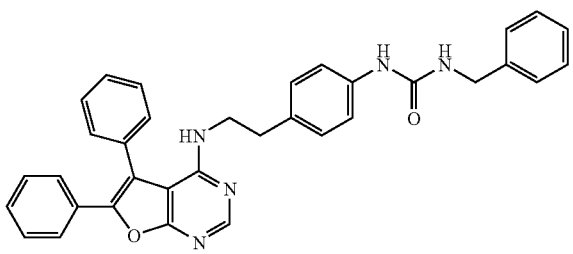
Compound 11
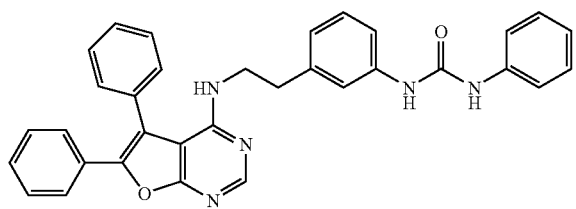
Compound 12
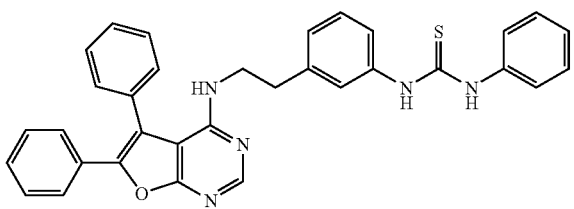
Compound 13
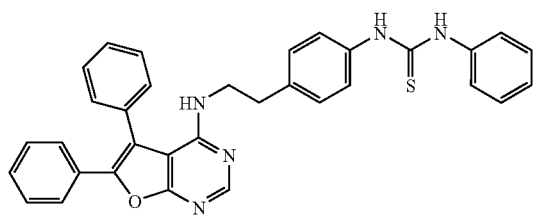
Compound 14
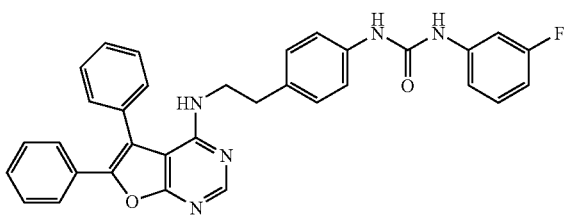
Compound 15
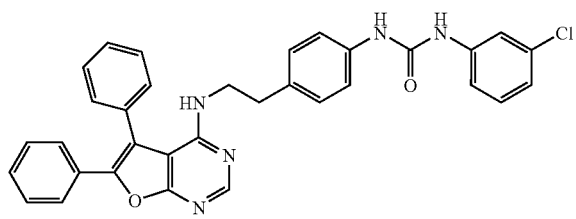
Compound 16
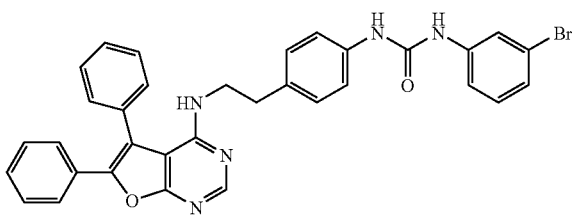
Compound 17
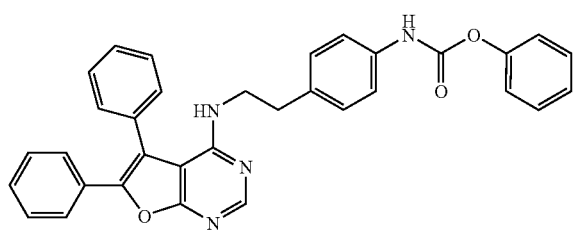
Compound 18
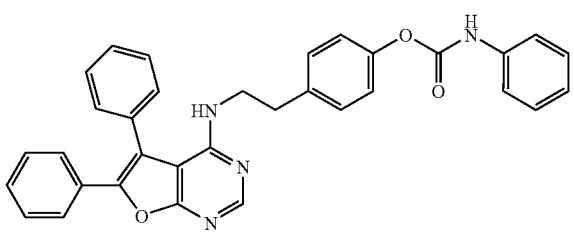
Compound 19
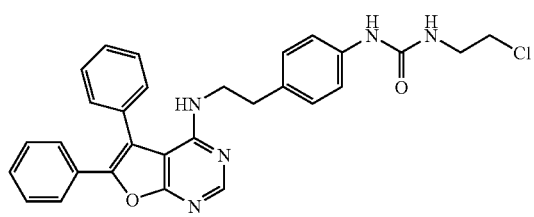
Compound 20
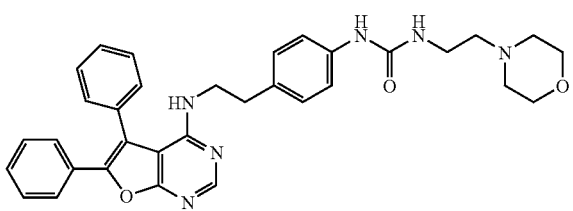

-continued
Compound 21
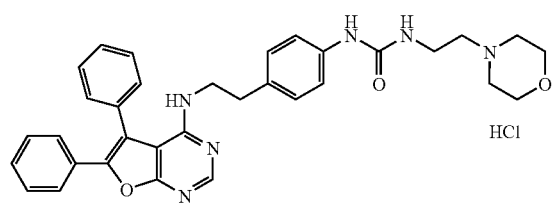
HCl
Compound 22
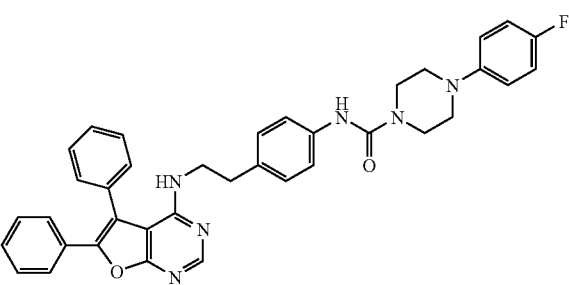
Compound 23
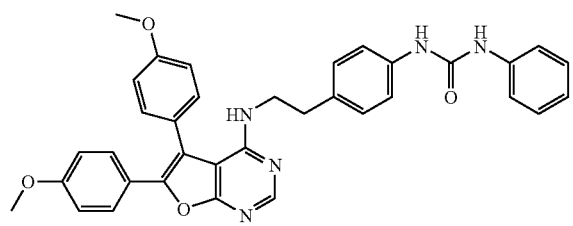
Compound 24
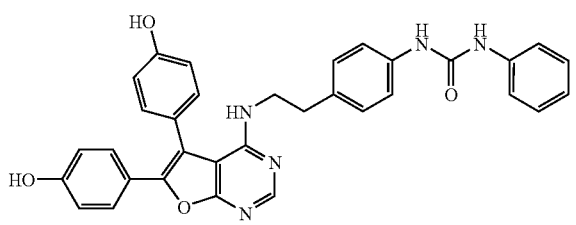
Compound 25
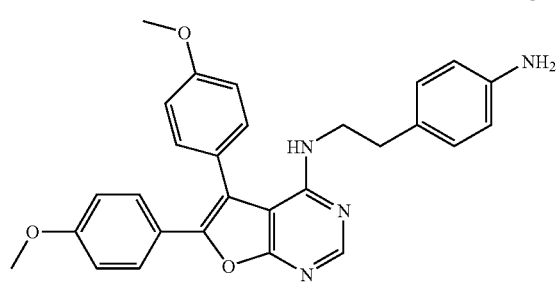
Compound 26
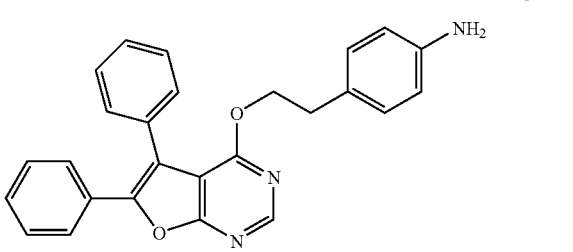
Compound 27
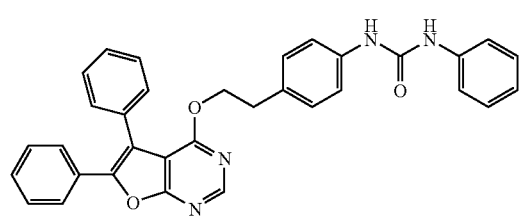
Compound 28
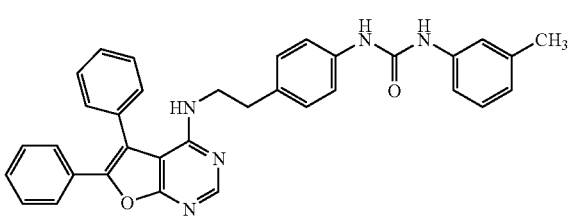
Compound 29
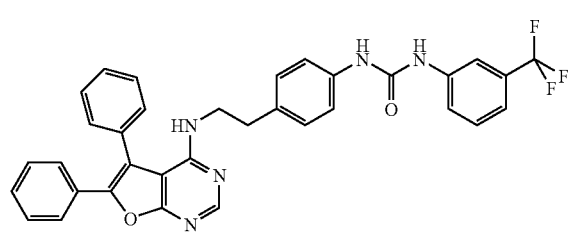
Compound 30
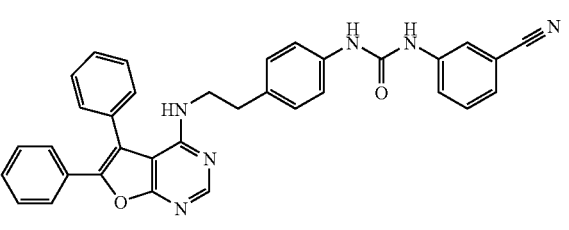
Compound 31
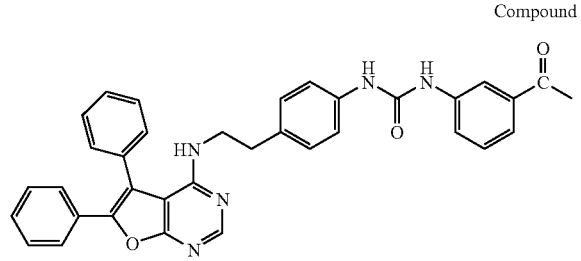
Compound 32
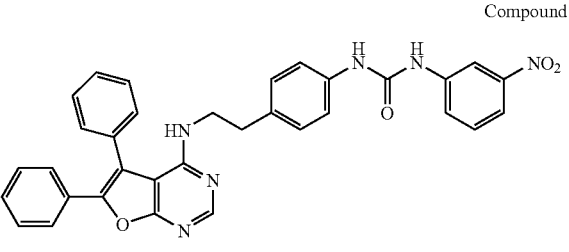

-continued
Compound 33
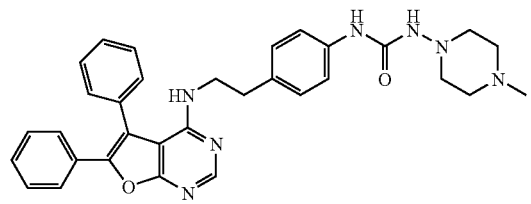
Compound 34
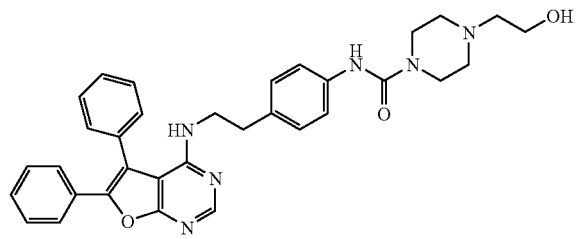
Compound 35
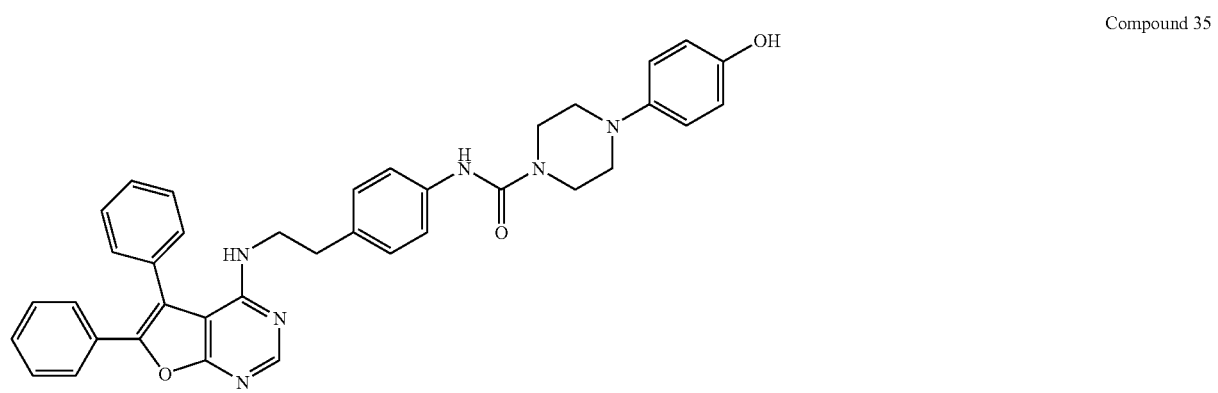
Compound 36
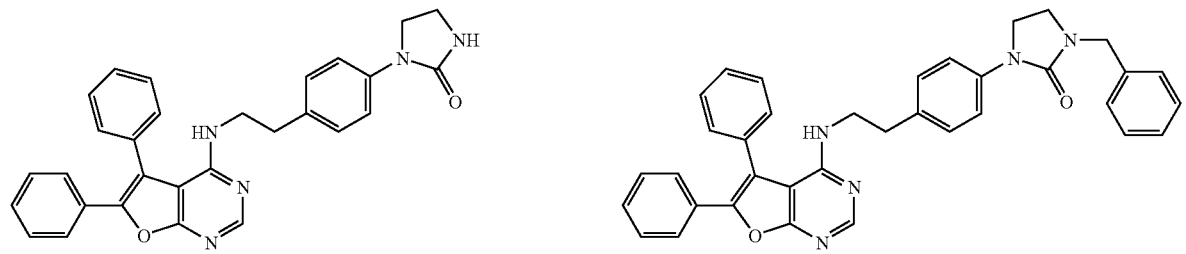
Compound 37
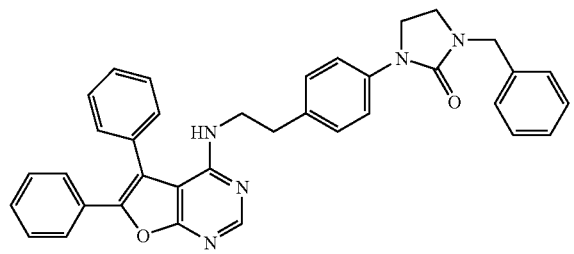
Compound 38
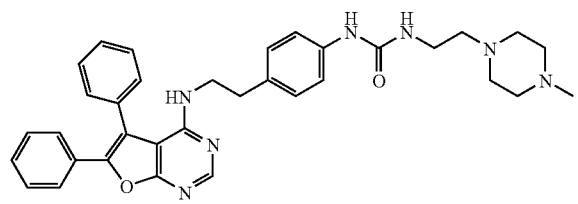
Compound 39
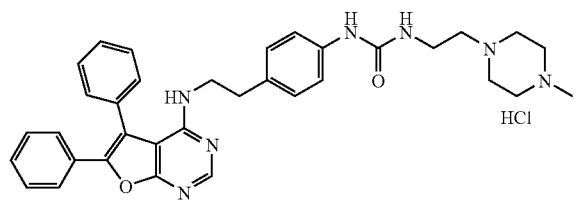
Compound 40
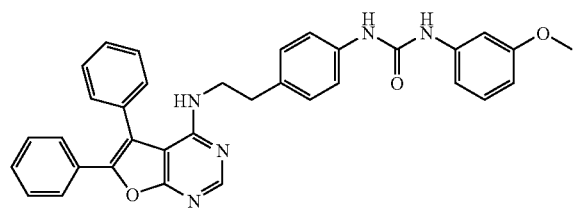
Compound 41
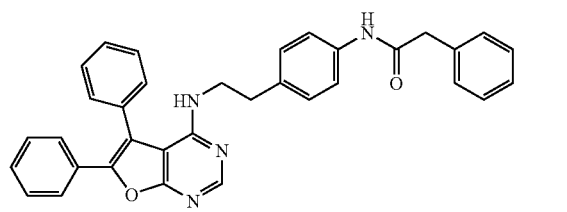

-continued
Compound 42
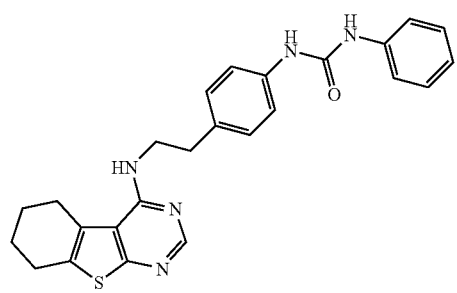
Compound 43
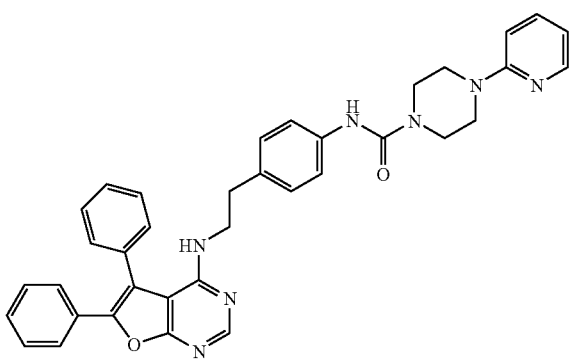
Compound 44
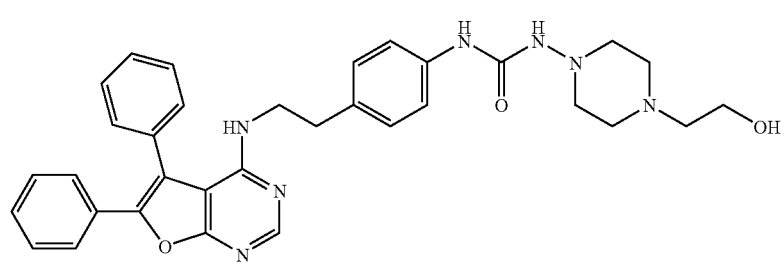
Compound 45
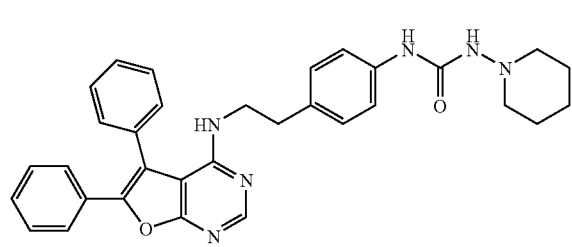
Compound 46
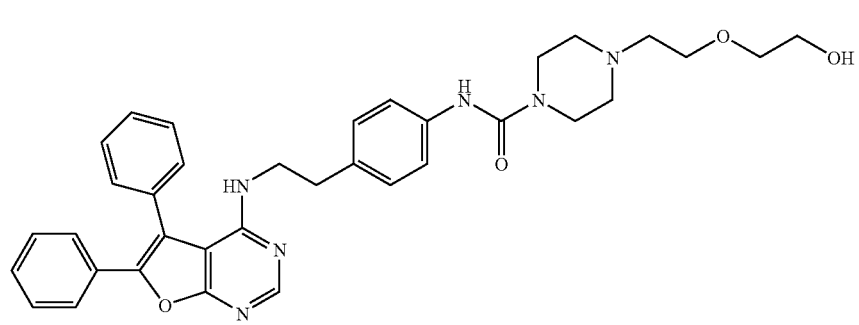
Compound 47
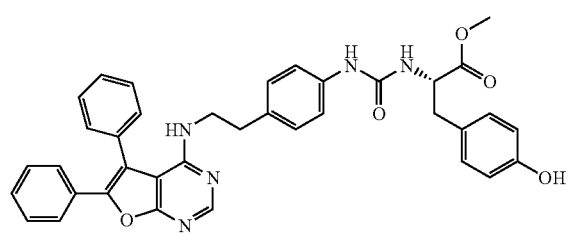
Compound 48
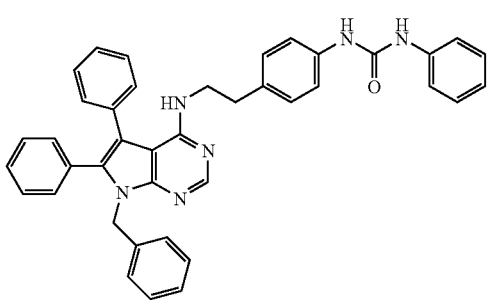

-continued
Compound 49
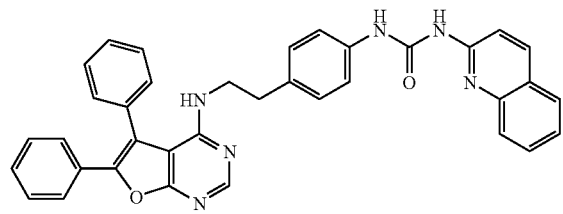
Compound 50
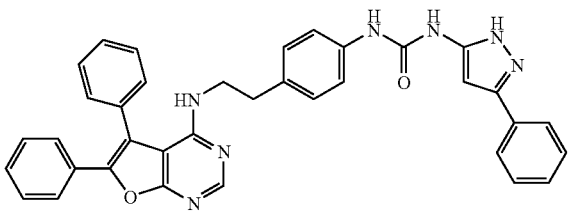
Compound 51
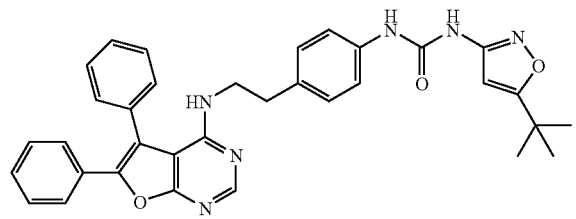
Compound 52
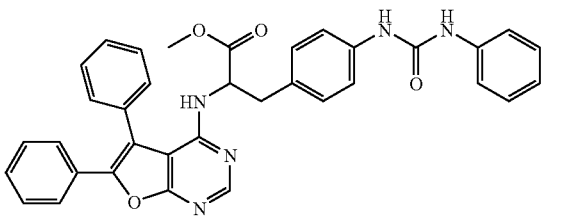
Compound 53
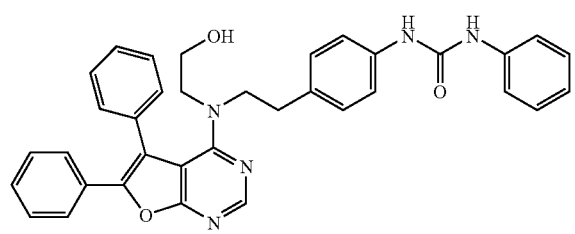
Compound 54
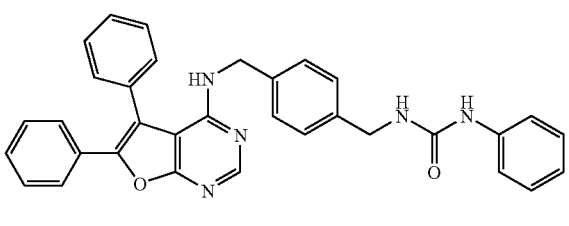
Compound 55
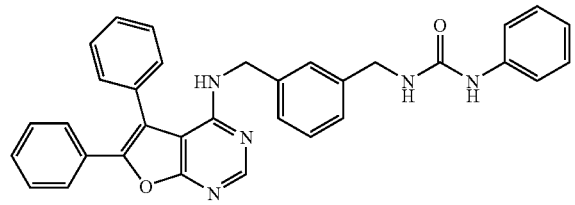
Compound 56
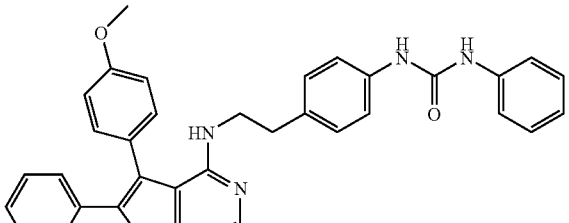
Compound 57
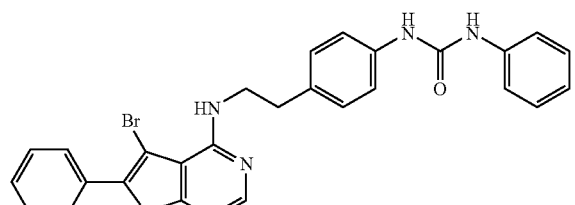
Compound 58
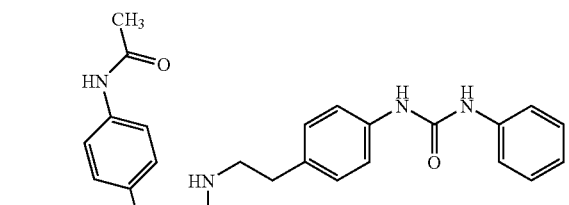
Compound 59
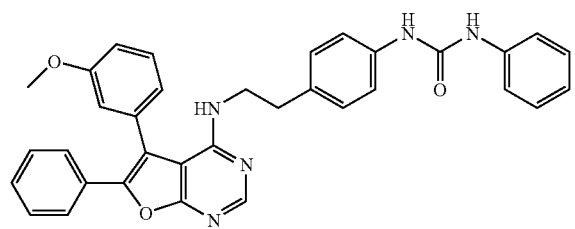
Compound 60
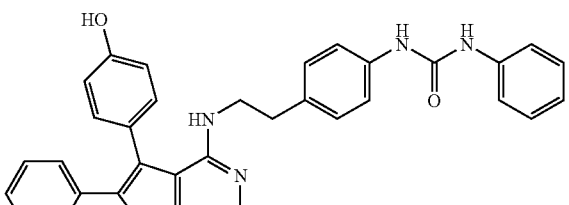

-continued

-continued
Compound 75
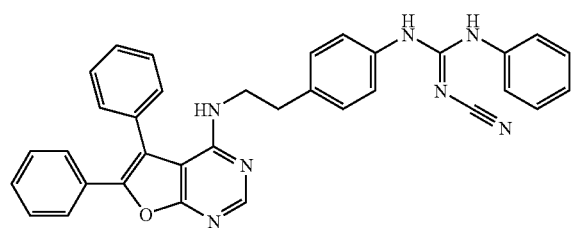
Compound 76
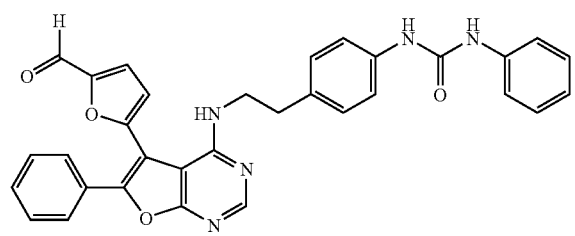
Compound 77
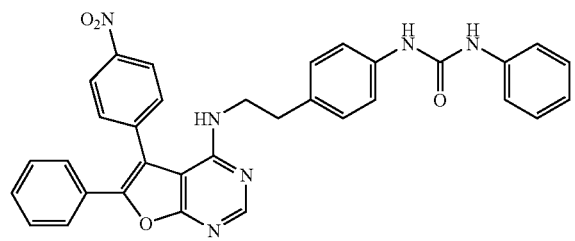
Compound 78
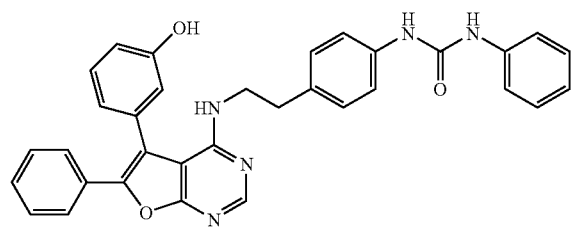
Compound 79
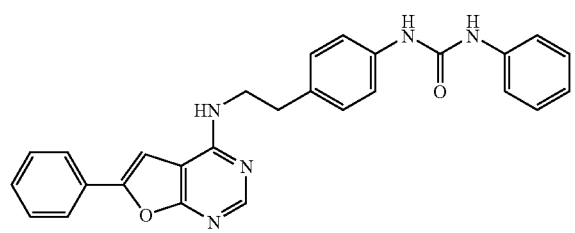
Compound 80
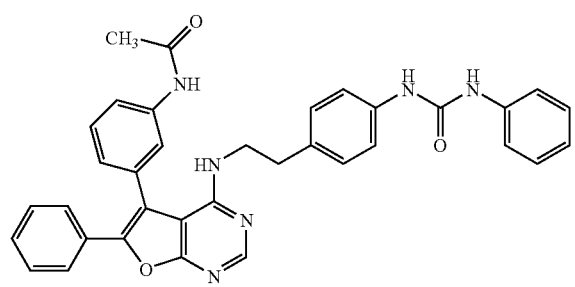
Compound 81
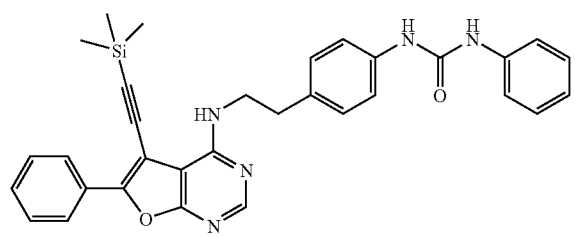
Compound 82
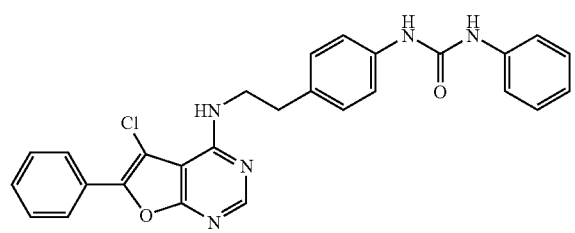
Compound 83
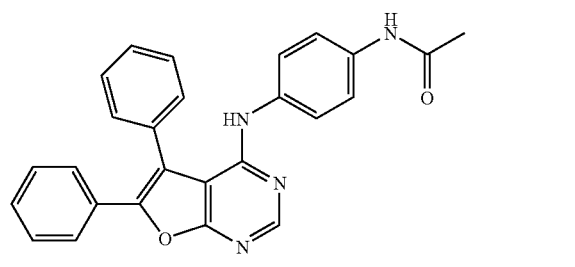
Compound 84
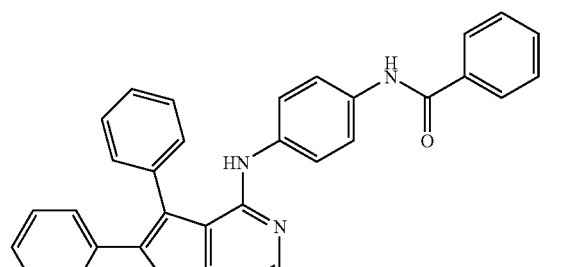

-continued
Compound 85
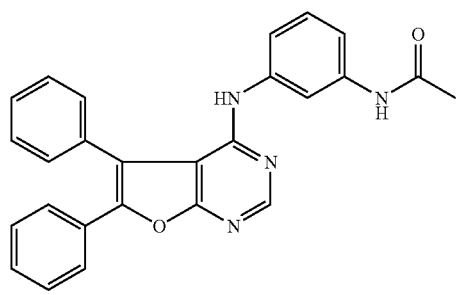
Compound 86
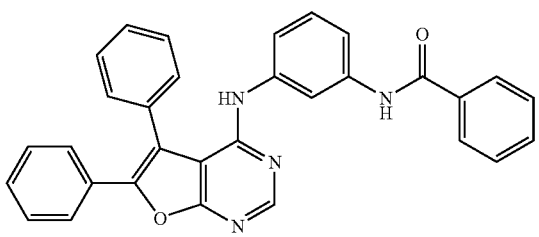
Compound 87
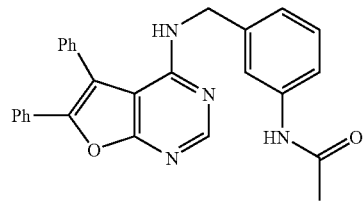
Compound 88
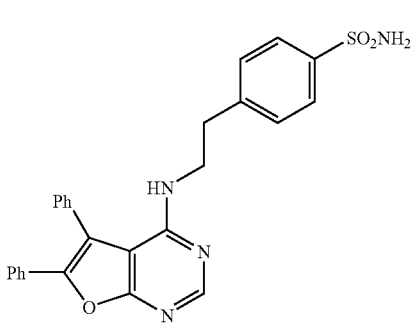
Compound 89
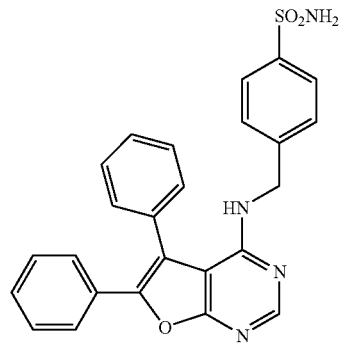
Compound 90
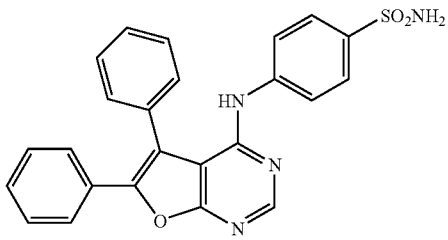
Compound 91
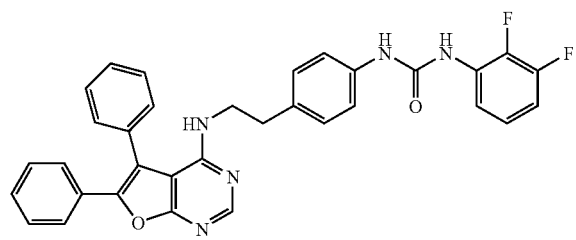
Compound 92
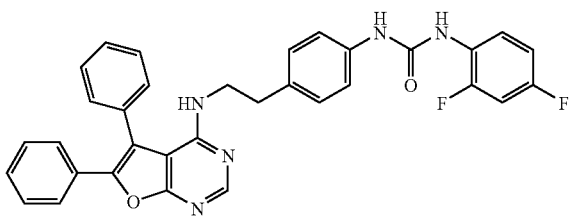
Compound 93
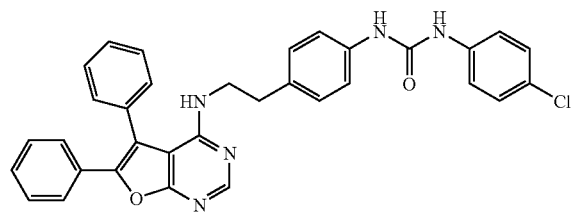
Compound 94
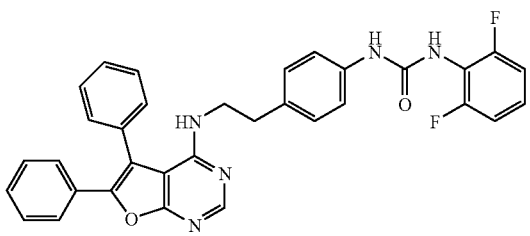

Compound 95
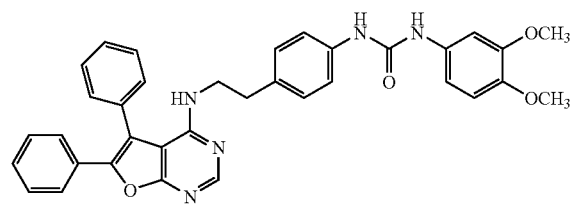
Compound 96
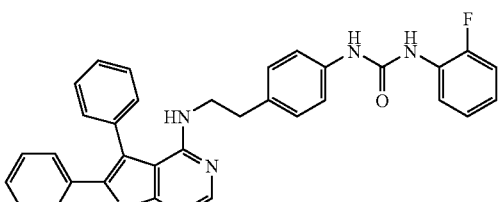
Compound 97
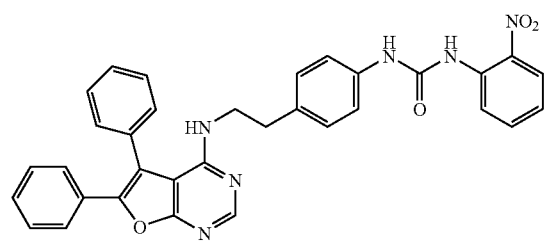
Compound 98
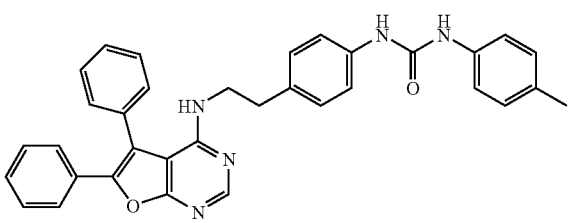
Compound 99
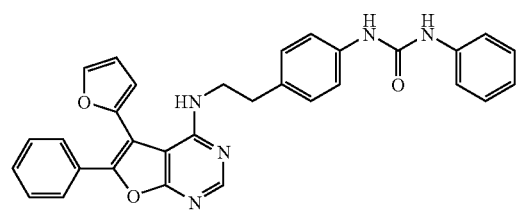
Compound 100
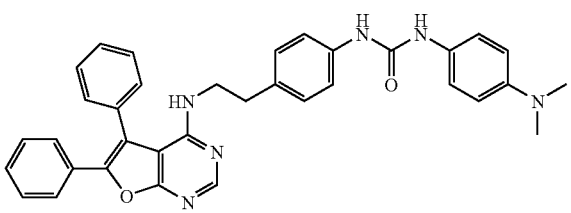
Compound 101
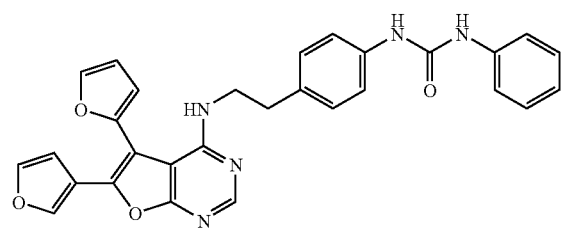
Compound 102
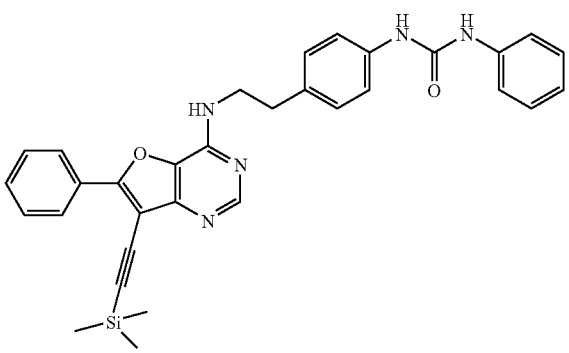
Compound 103
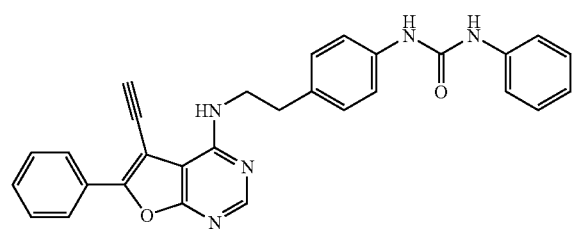
Compound 104
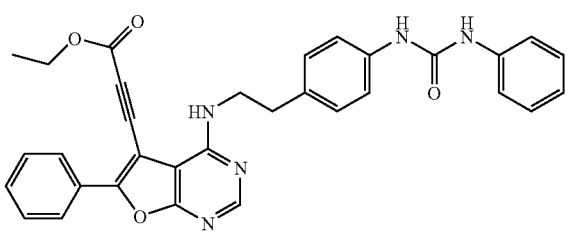
Compound 105
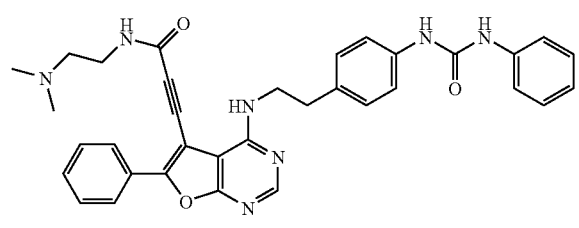
Compound 106
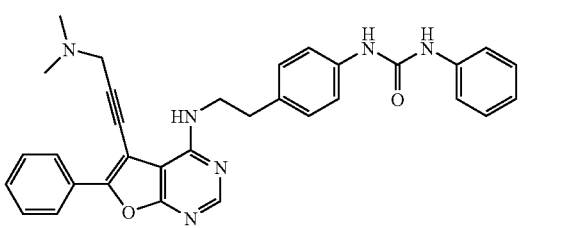

-continued
Compound 107
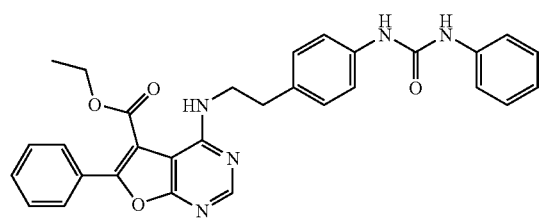
Compound 108
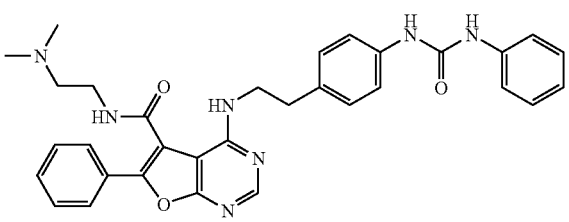
Compound 109
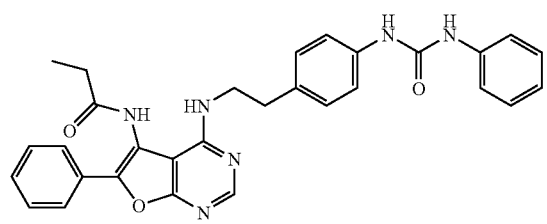
Compound 110
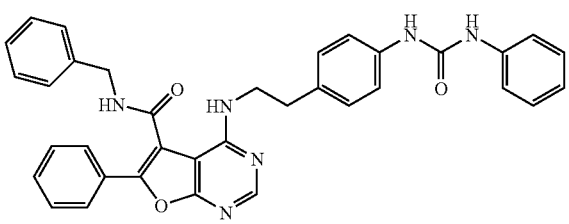
Compound 111
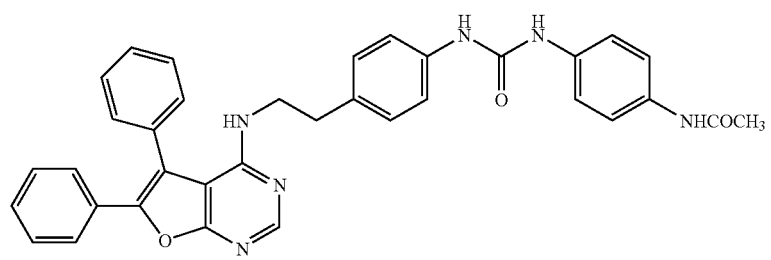
Compound 112
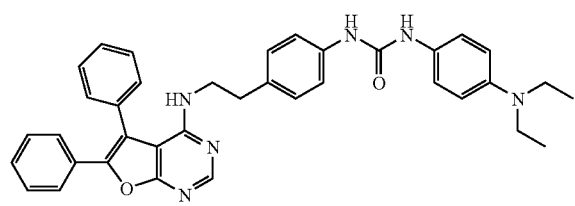
Compound 113
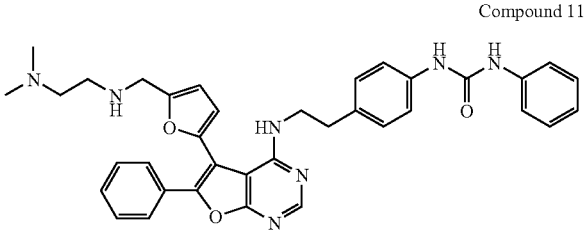
Compound 114
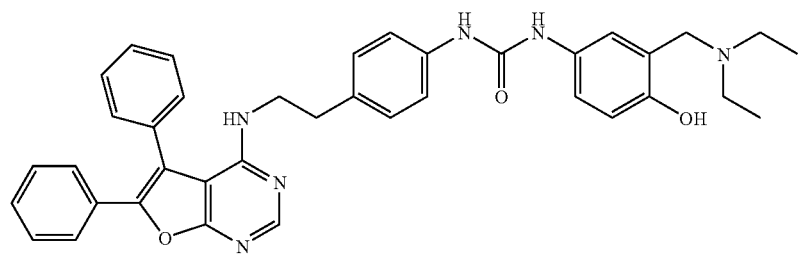
Compound 115
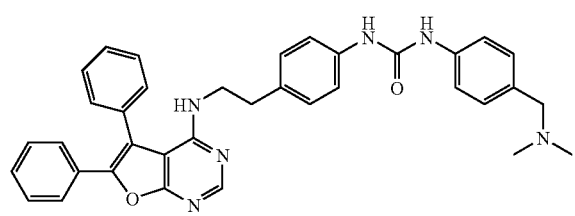
Compound 116
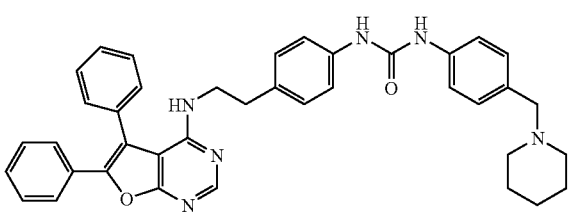

-continued
Compound 117
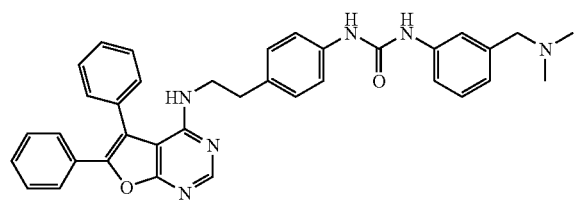
Compound 118
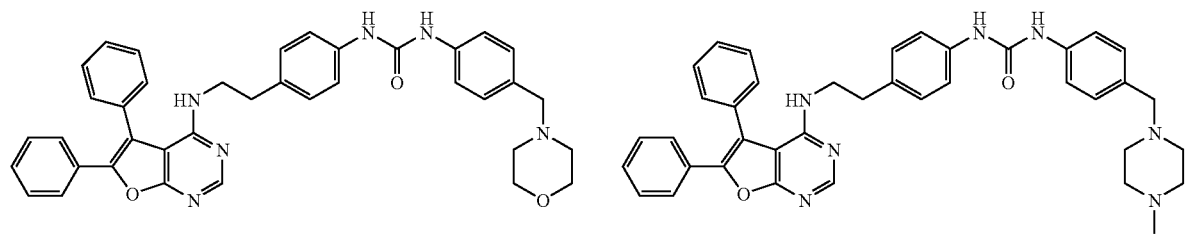
Compound 119
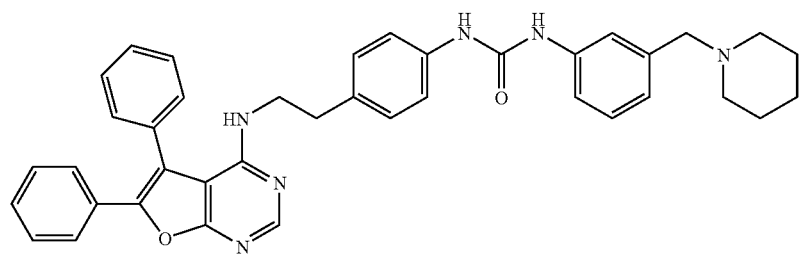
Compound 120
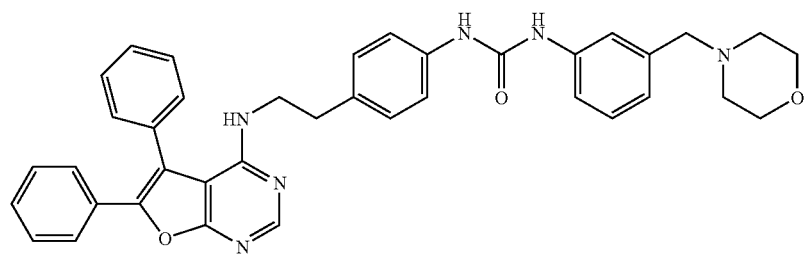
Compound 121
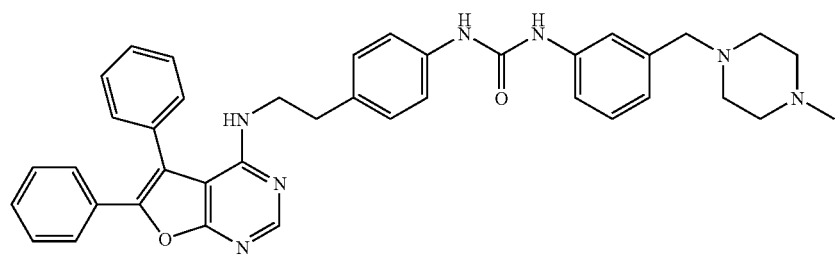
Compound 122
Compound 123
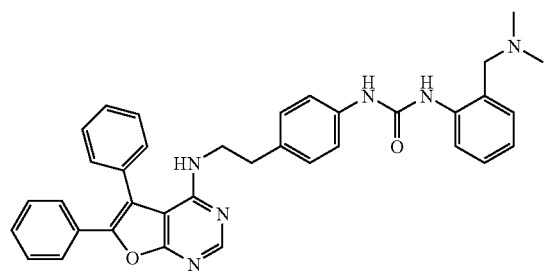
Compound 124
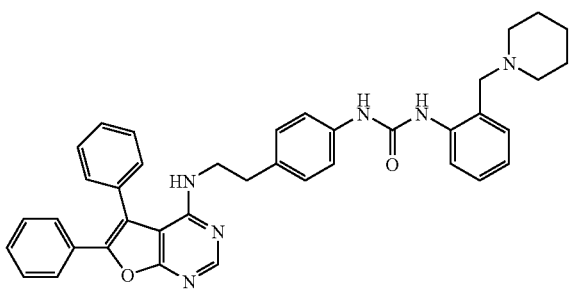

-continued
Compound 125
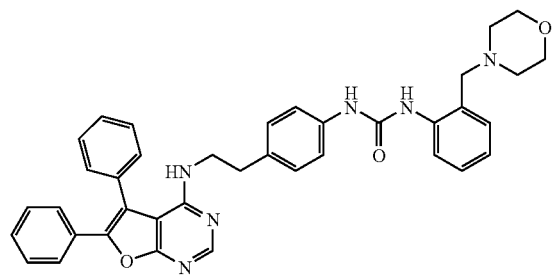
Compound 126
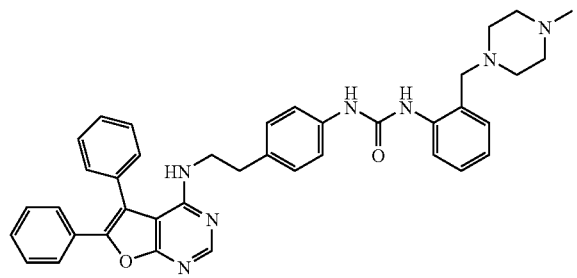
Compound 127
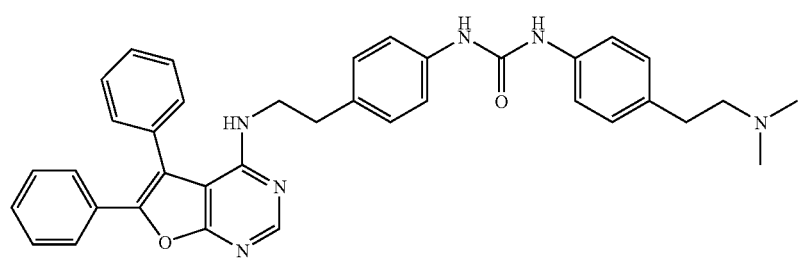
Compound 128
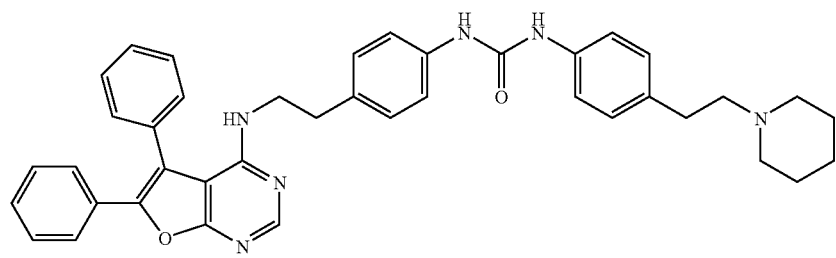
Compound 129
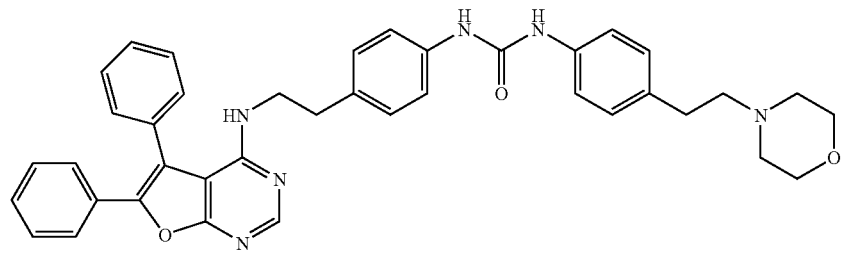
Compound 130
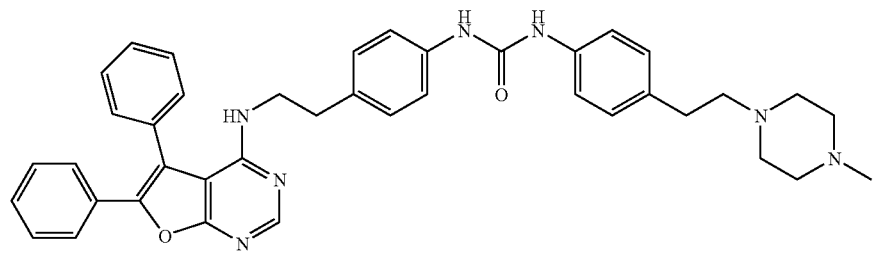
Compound 131
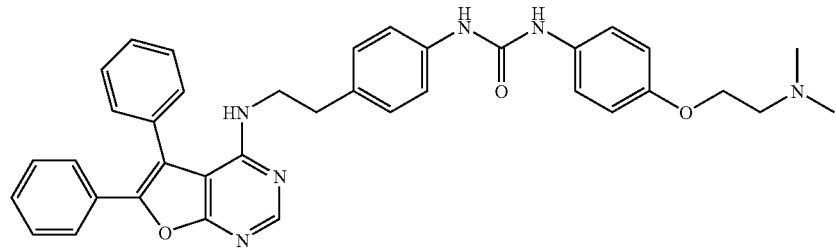

-continued
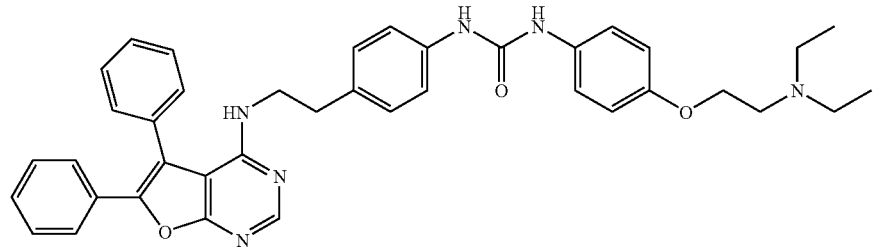
Compound 132
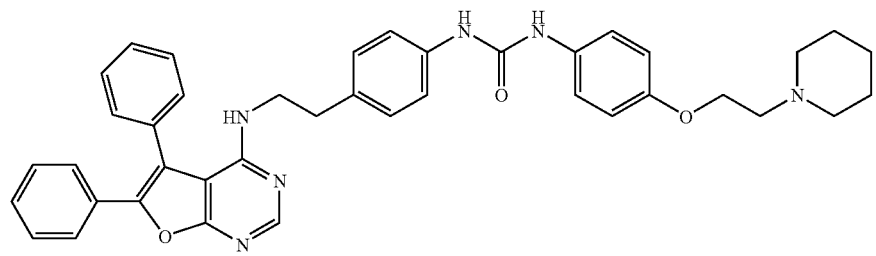
Compound 133
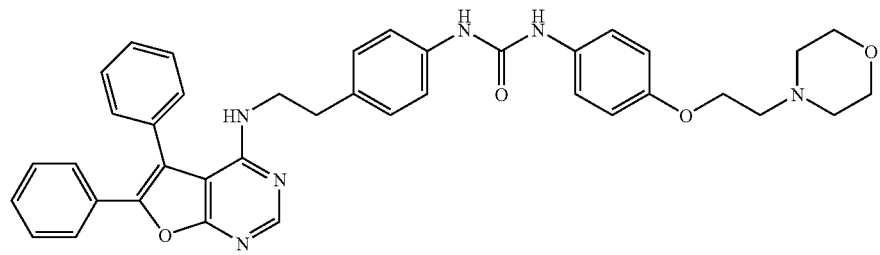
Compound 134
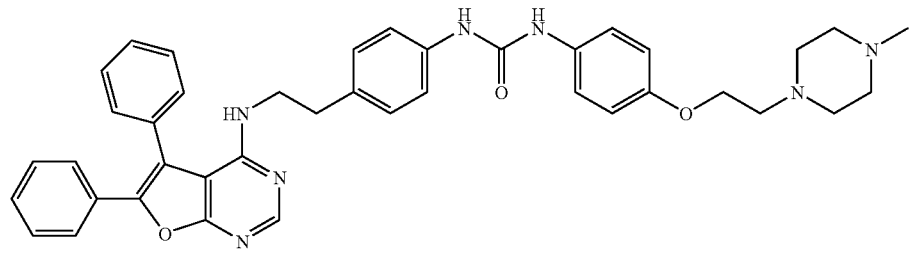
Compound 135
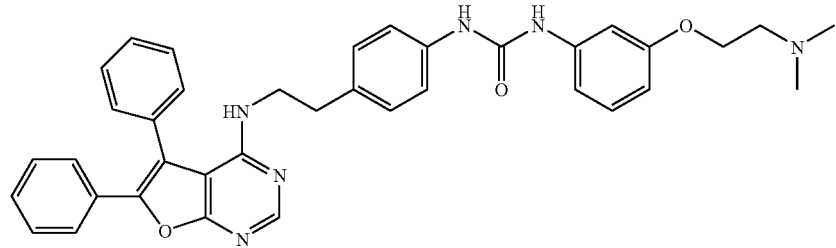
Compound 136
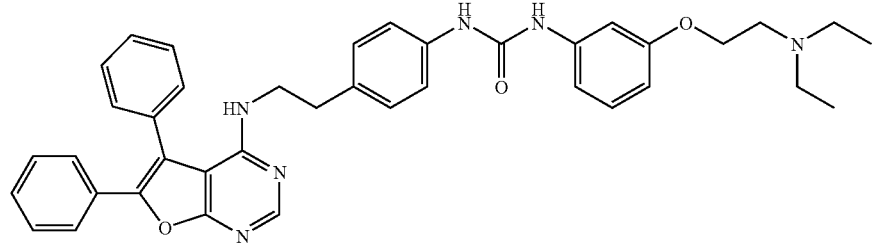
Compound 137

-continued
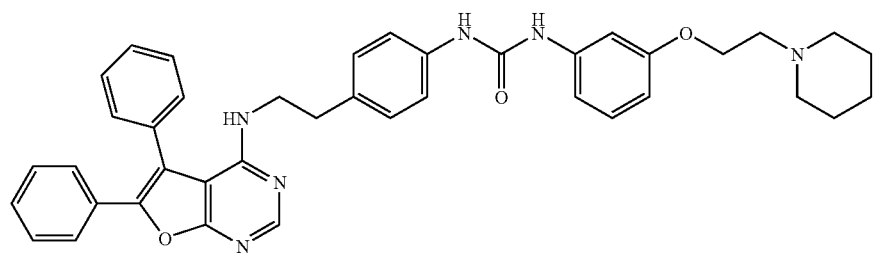
Compound 138
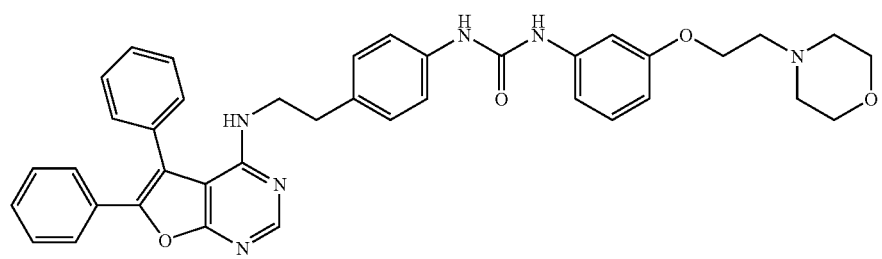
Compound 139
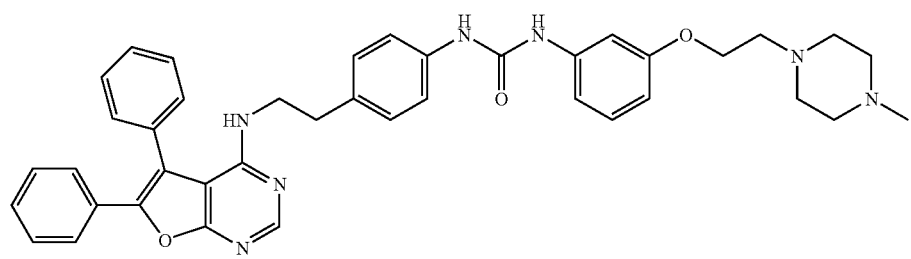
Compound 140
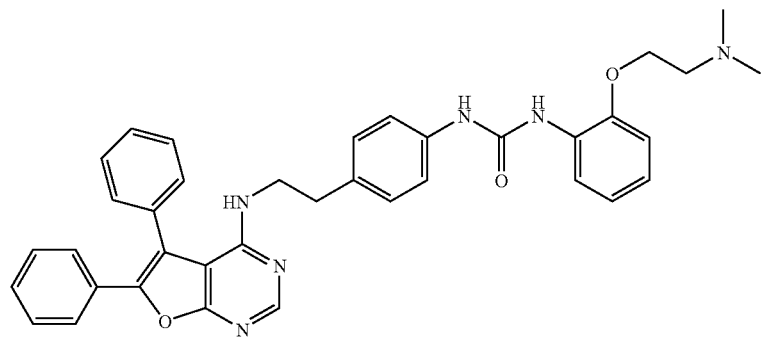
Compound 141
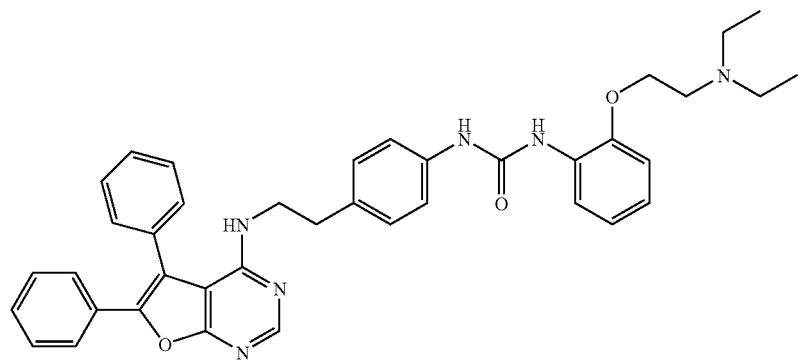
Compound 142

-continued
Compound 143
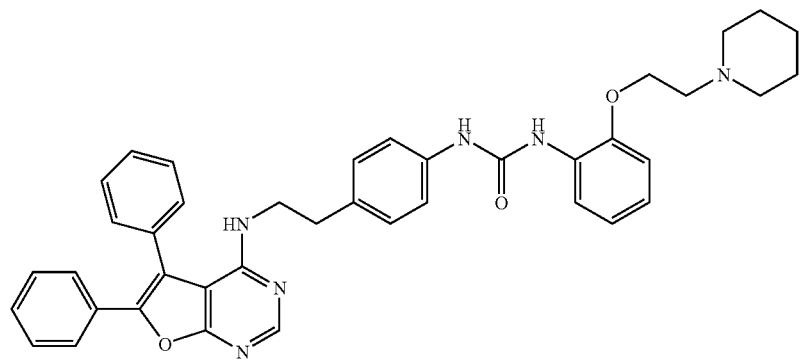
Compound 144
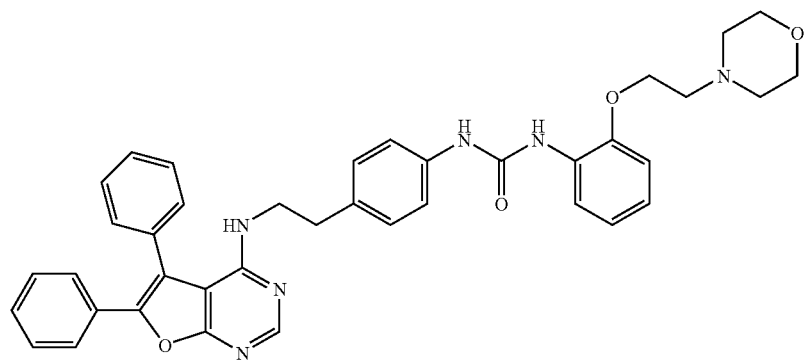
Compound 145
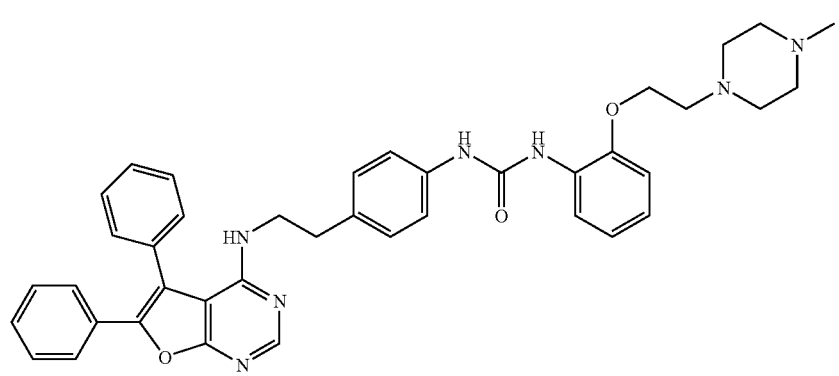
Compound 146
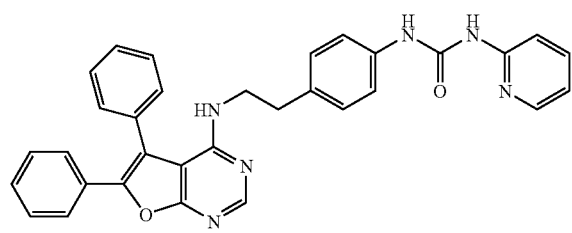
Compound 147
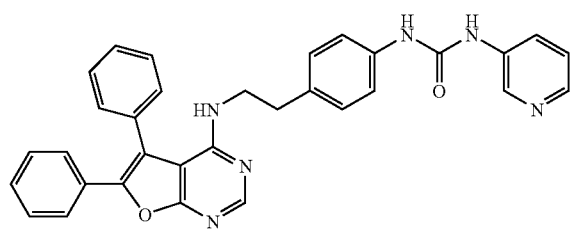
Compound 148
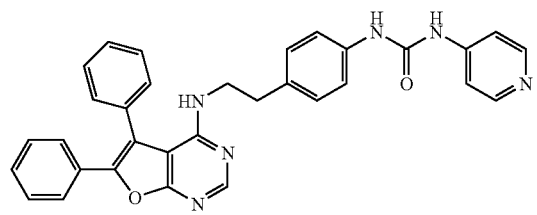
Compound 149
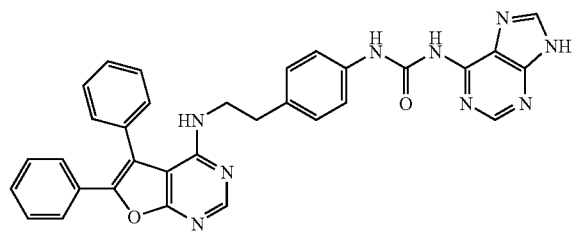

-continued
Compound 150
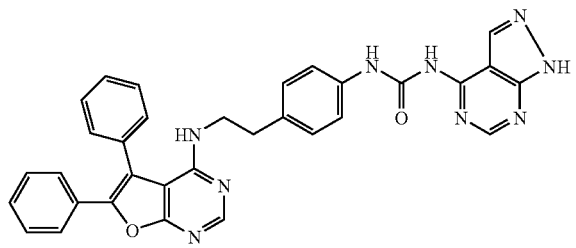
Compound 151
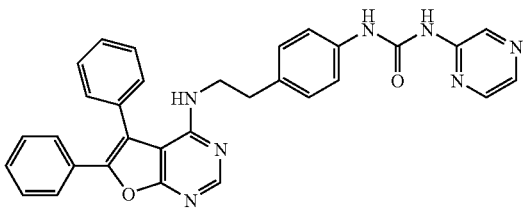
Compound 152
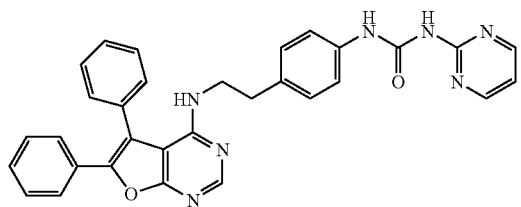
Compound 153
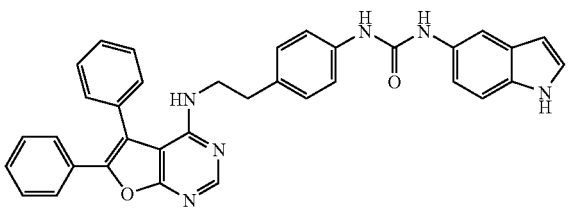
Compound 154
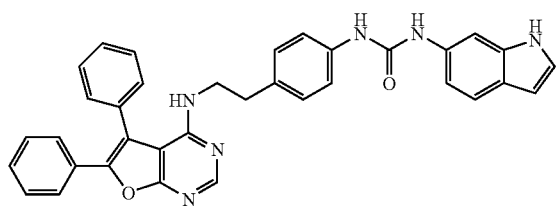
Compound 155
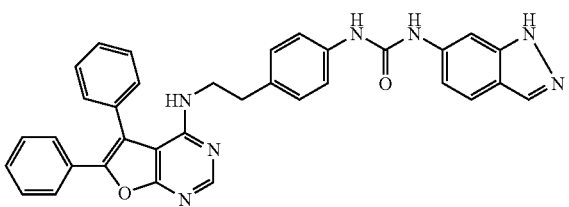
Compound 156
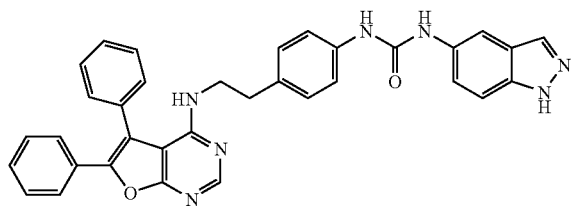
Compound 157
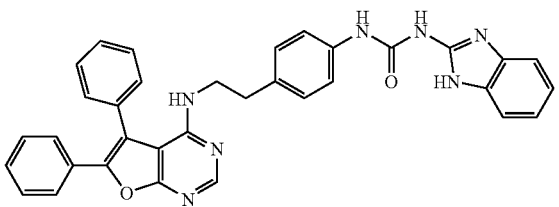
Compound 158
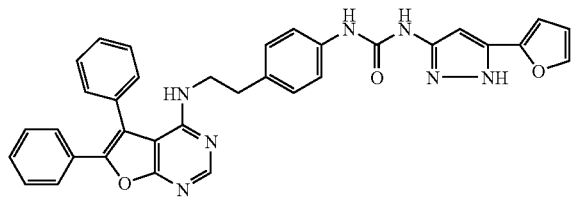
Compound 159
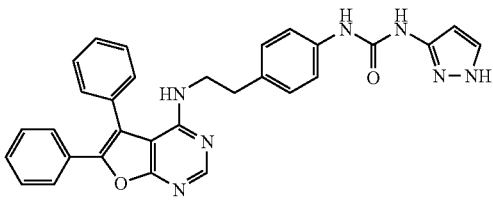
Compound 160
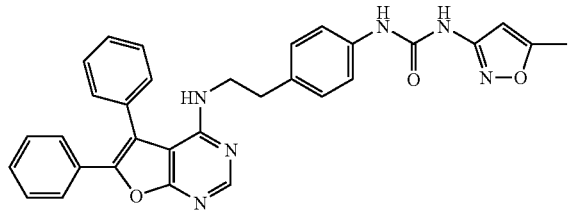
Compound 161
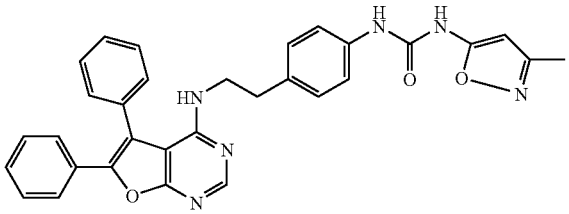

Compound 162
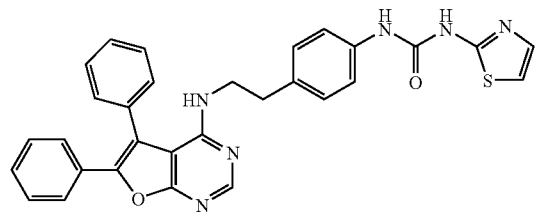
Compound 163
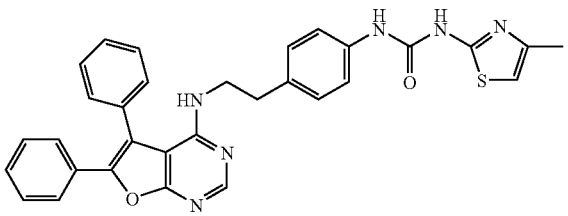
Compound 164
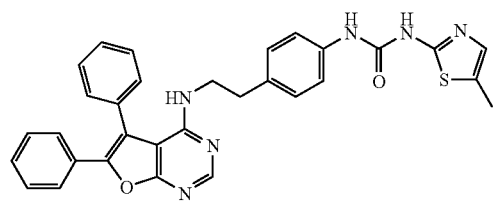
Compound 165
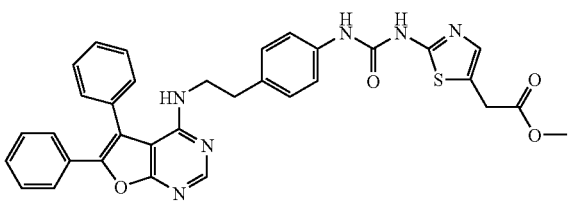
Compound 166
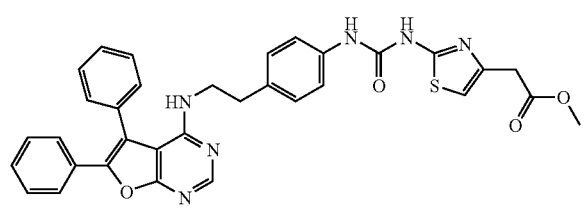
Compound 167
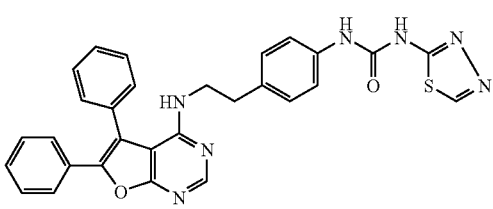
Compound 168
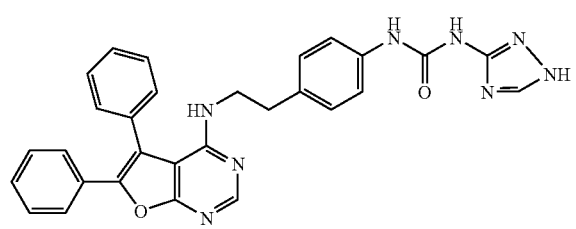
Compound 169
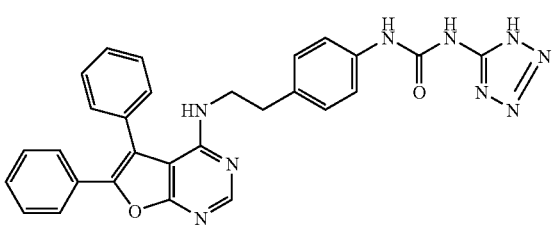
Compound 170
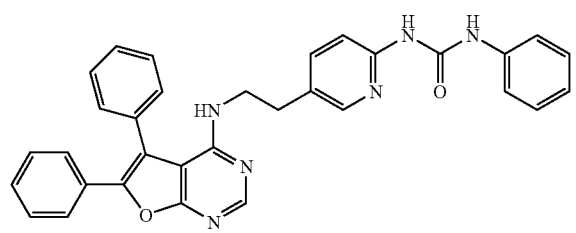
Compound 171
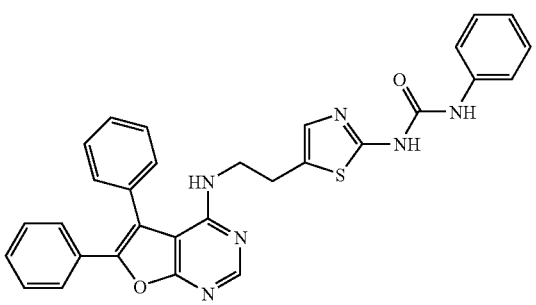
Compound 172
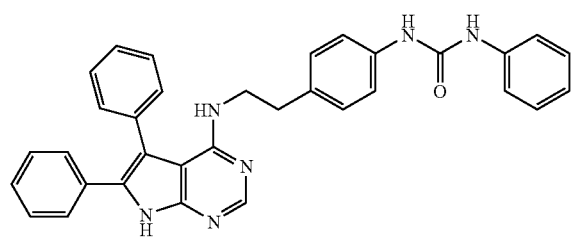
Compound 173
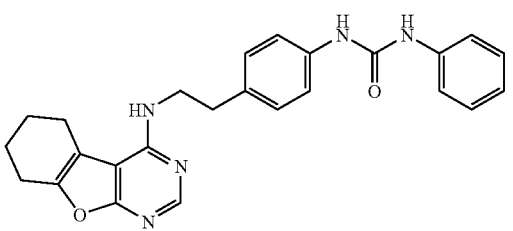

-continued
Compound 174
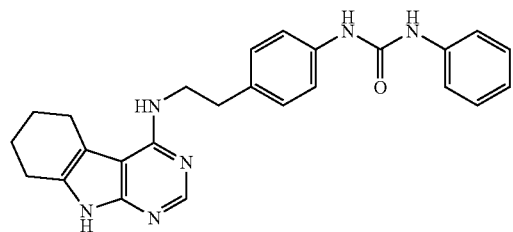
Compound 175
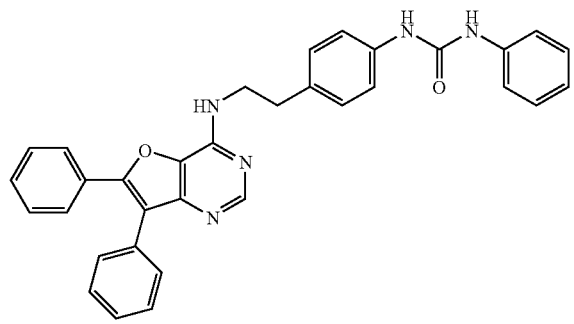
Compound 176
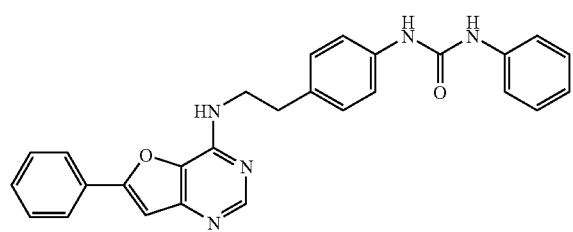
Compound 177
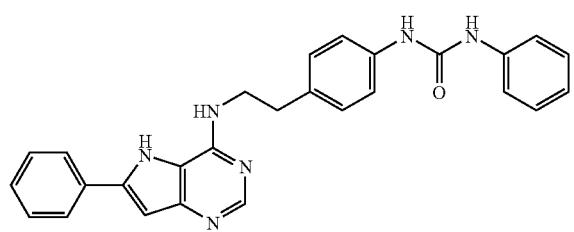
Compound 178
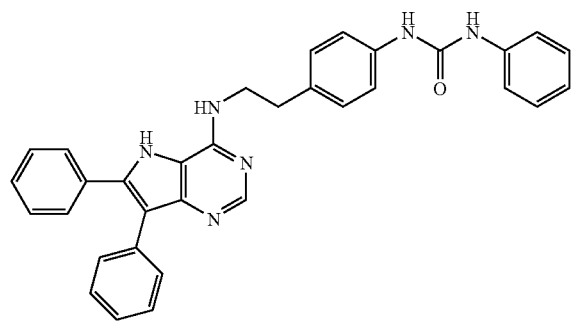
Compound 179
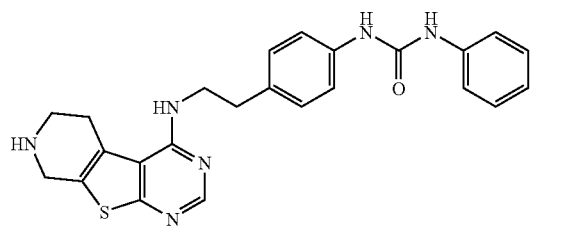
Compound 180
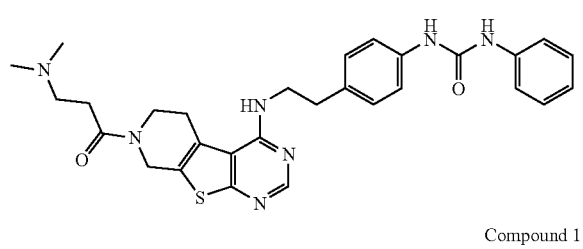
Compound 181
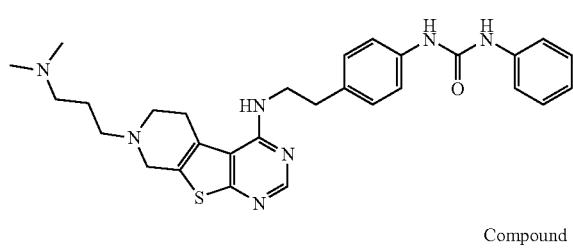
Compound 182
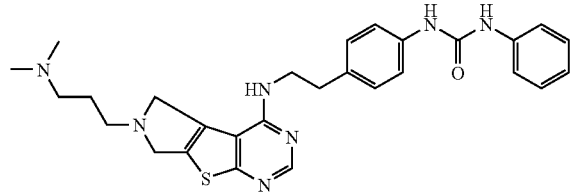
Compound 183
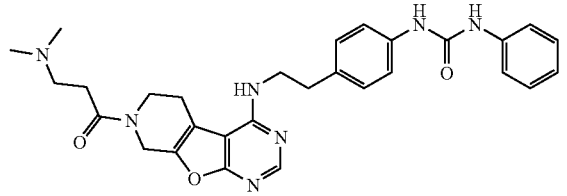
Compound 184
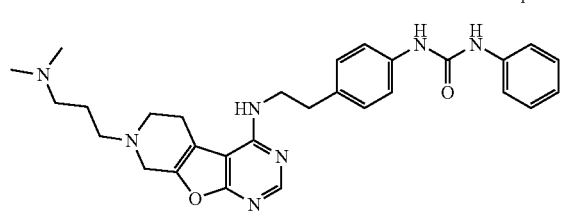
Compound 185
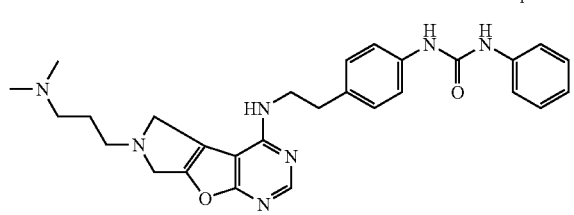

Compound 186
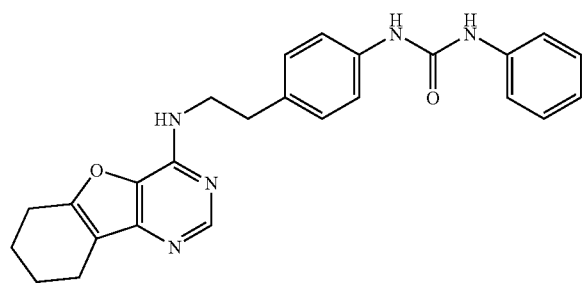
Compound 187
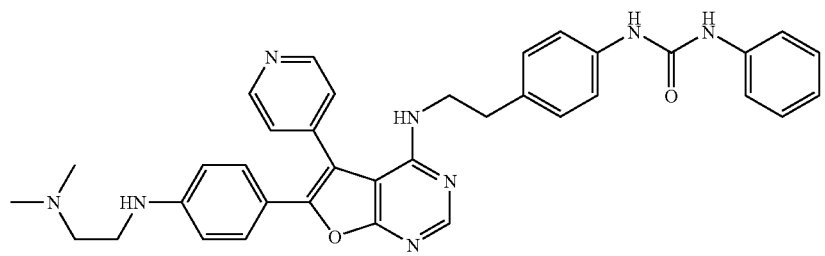
Compound 188
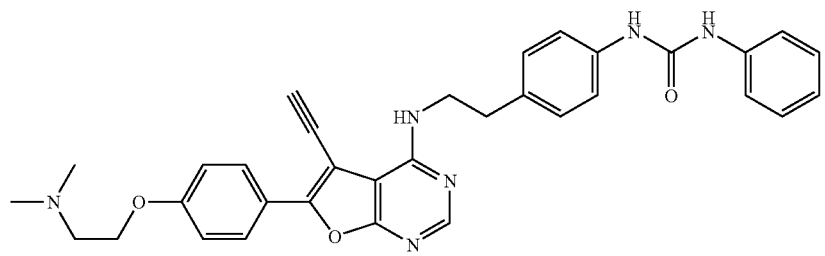
Compound 189
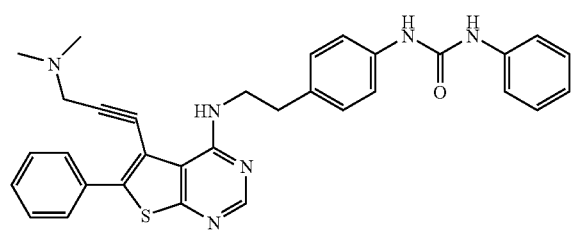
Compound 190
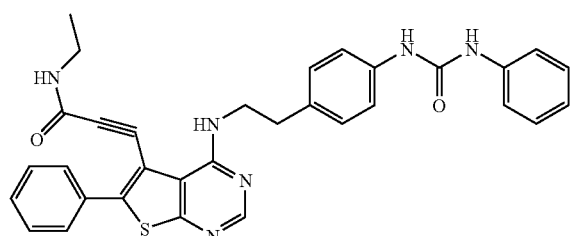
Compound 191
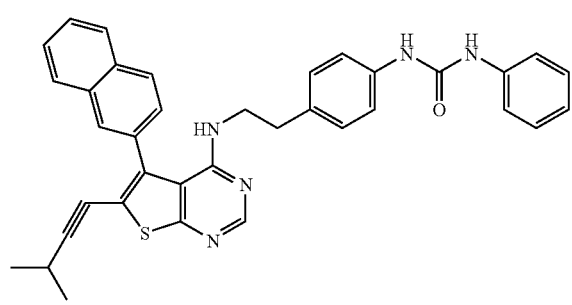
Compound 192
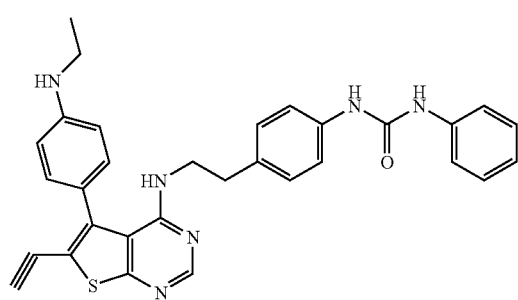
Compound 193
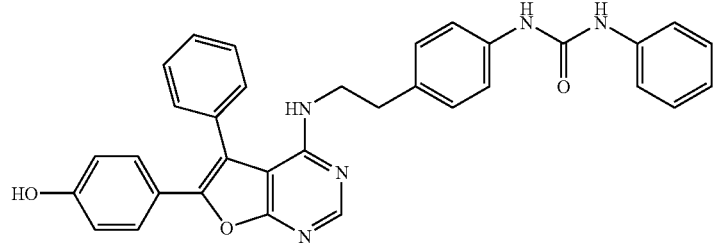

-continued
Compound 194
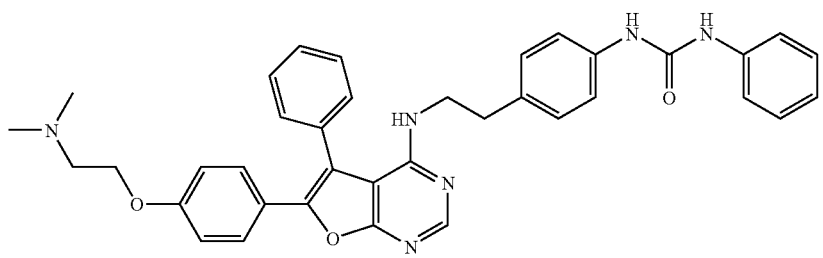
Compound 195
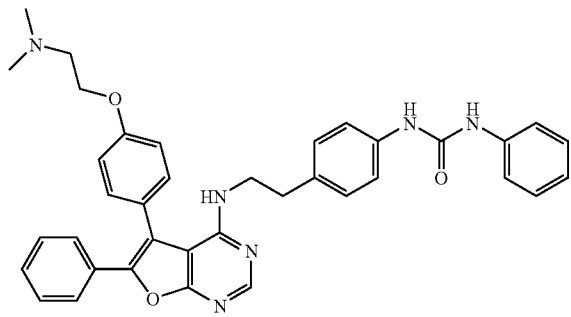
Compound 196
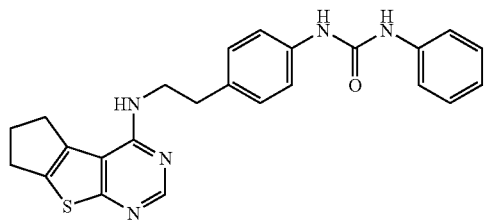
Compound 197
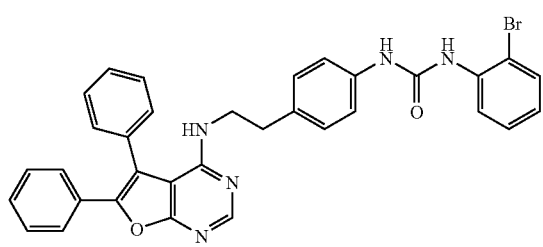
Compound 198
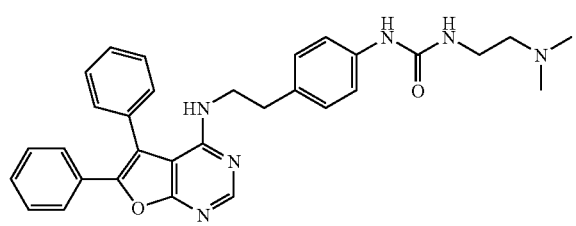
Compound 199
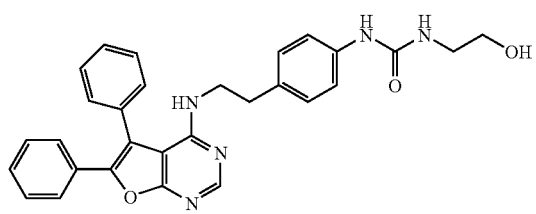
Compound 200
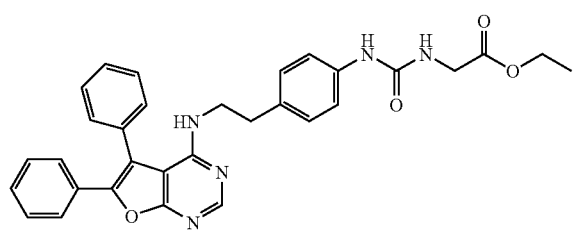
Compound 201
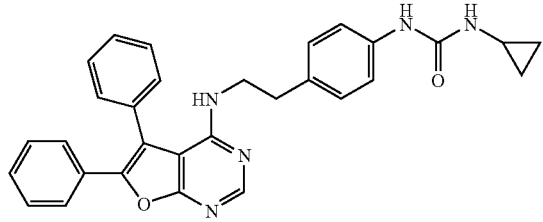
Compound 202
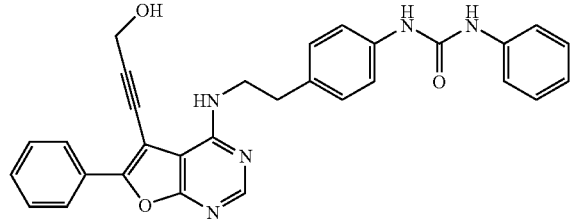
Compound 203
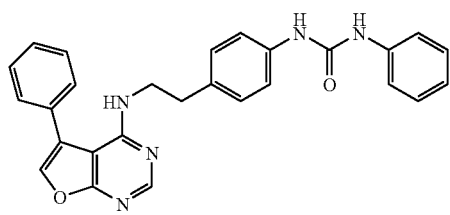
Compound 204
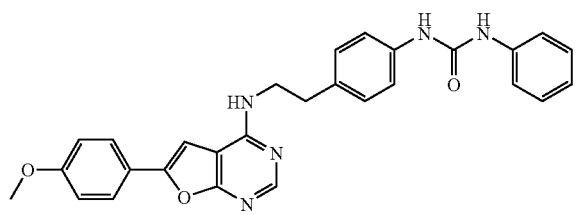

-continued
Compound 205
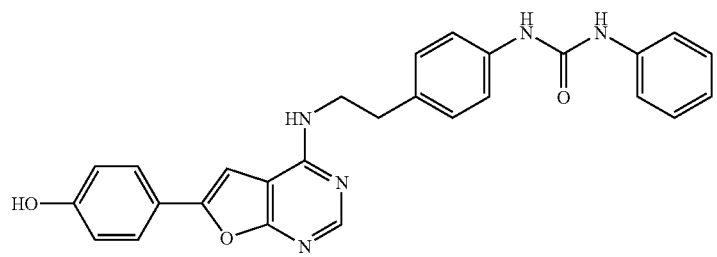
Compound 206
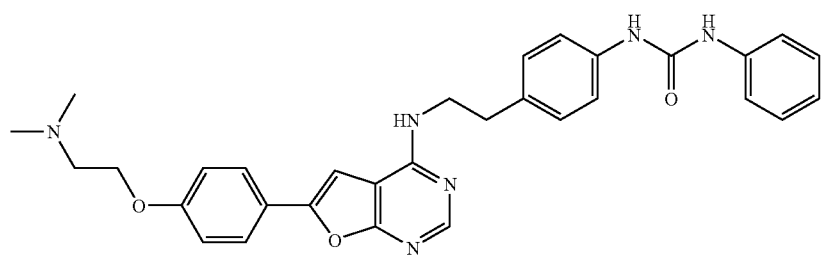
Compound 207
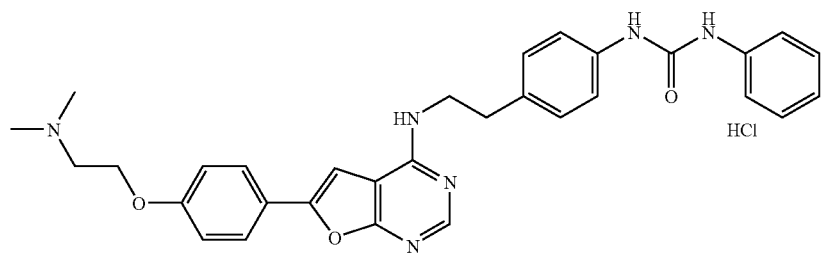
Compound 208
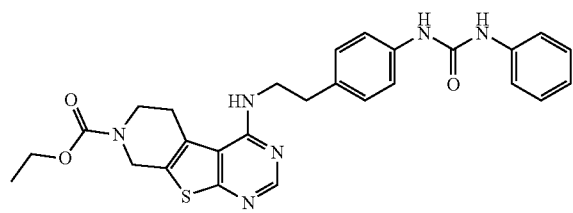
Compound 209
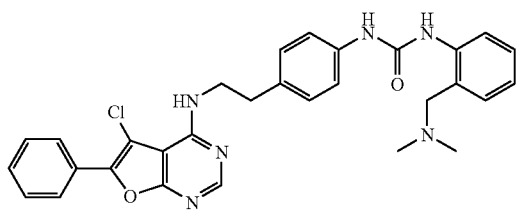
Compound 210
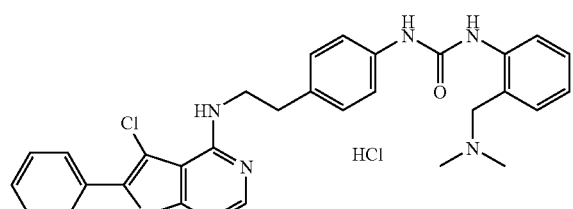
Compound 211
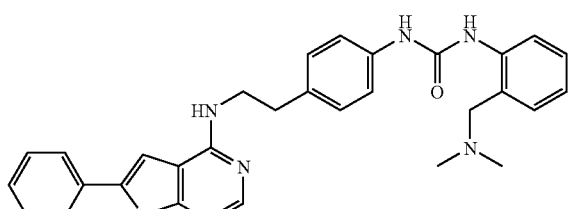
Compound 212
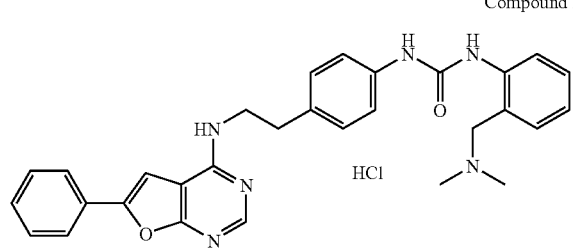
Compound 213
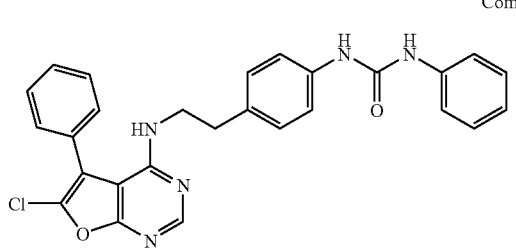

-continued
Compound 214
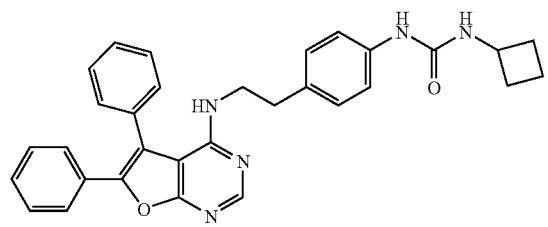
Compound 215
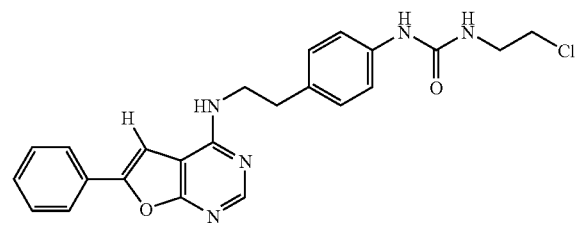
Compound 216
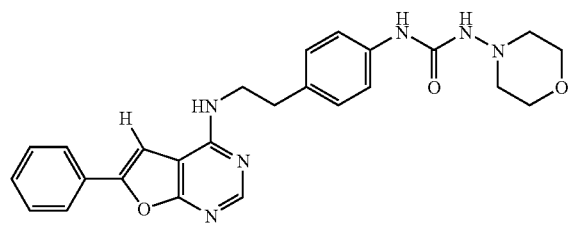
Compound 217
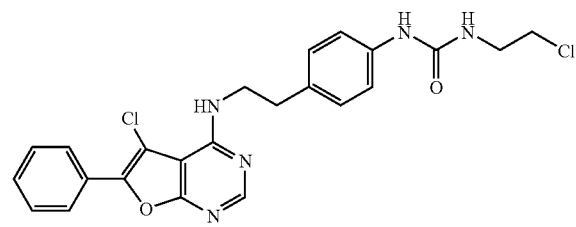
Compound 218
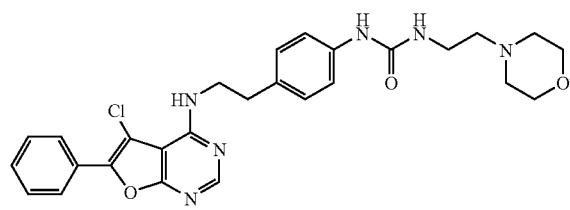
Compound 219
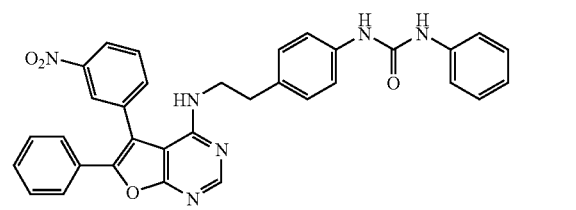
Compound 220
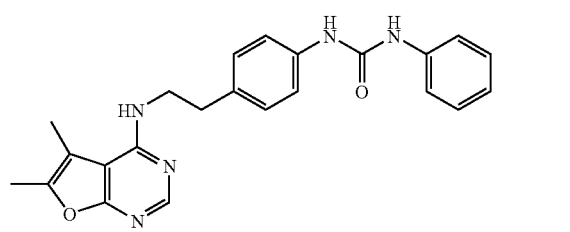
Compound 221
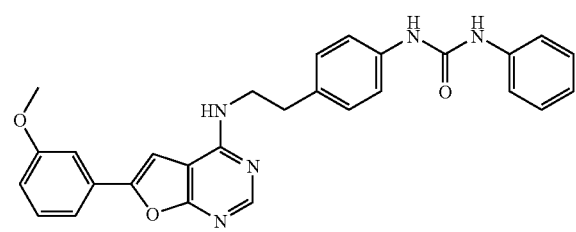
Compound 222
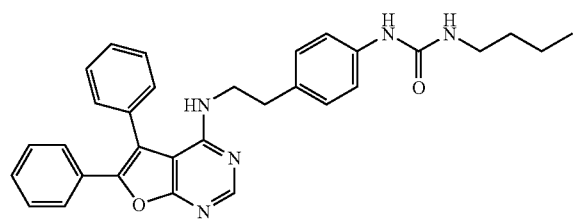
Compound 223
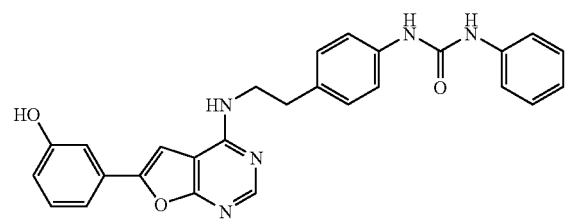
Compound 224
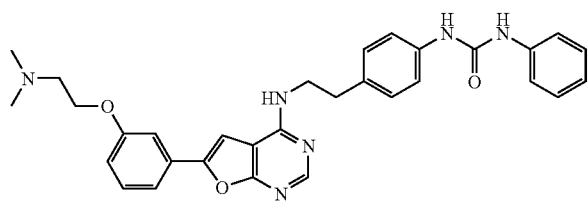
Compound 225
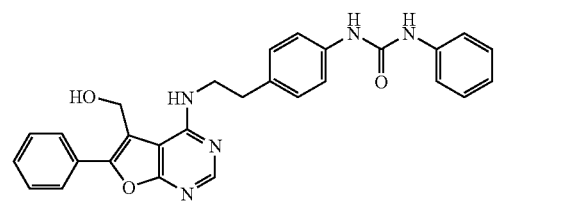

-continued
Compound 226
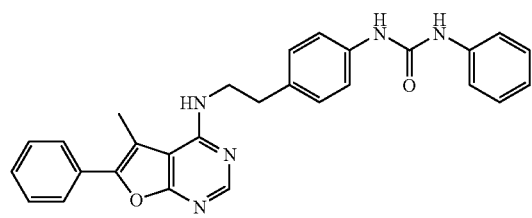
Compound 227
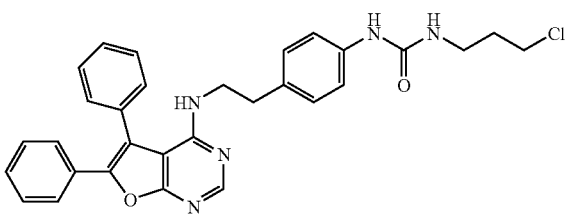
Compound 228
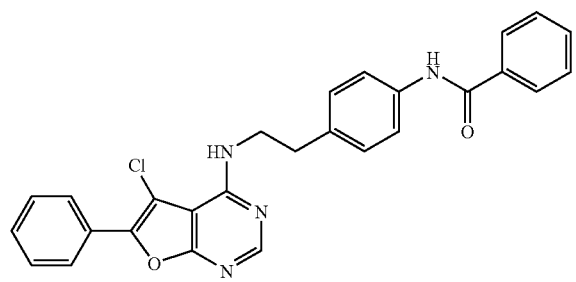
Compound 229
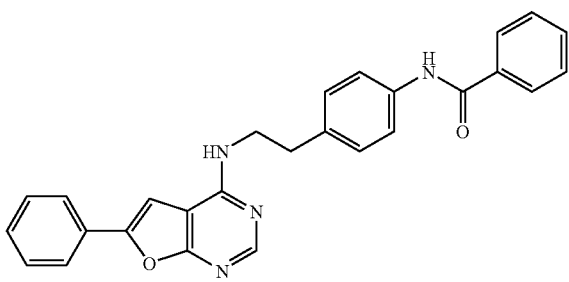
Compound 230
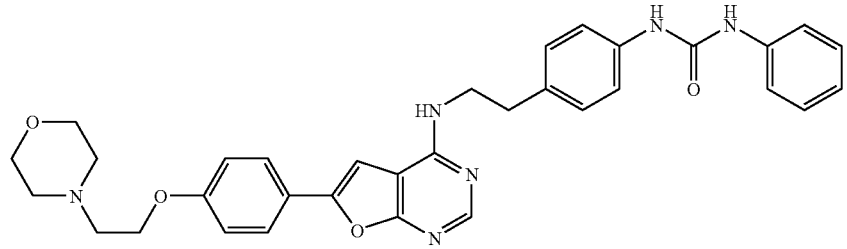
Compound 231
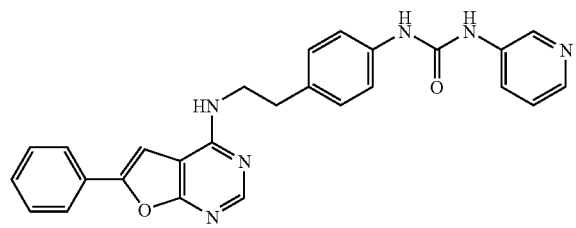
Compound 232
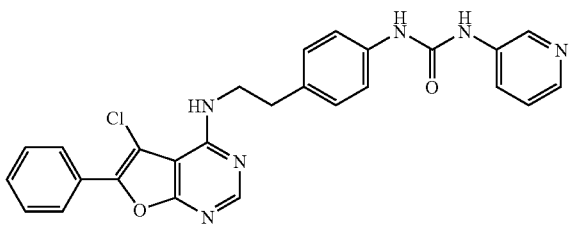
Compound 233
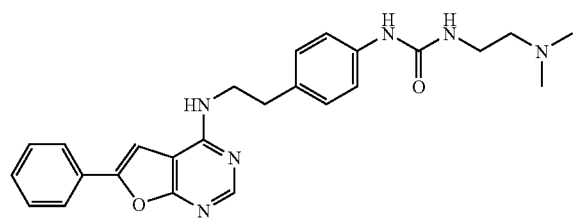
Compound 234
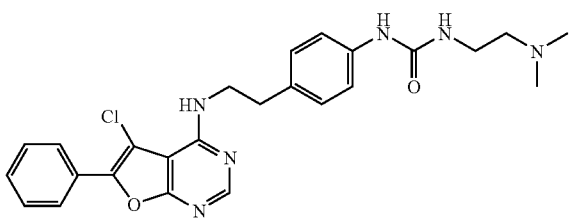
Compound 235
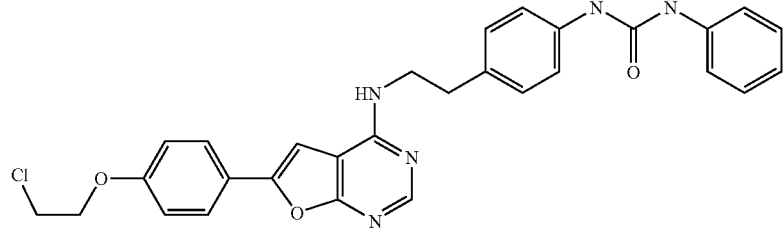

-continued
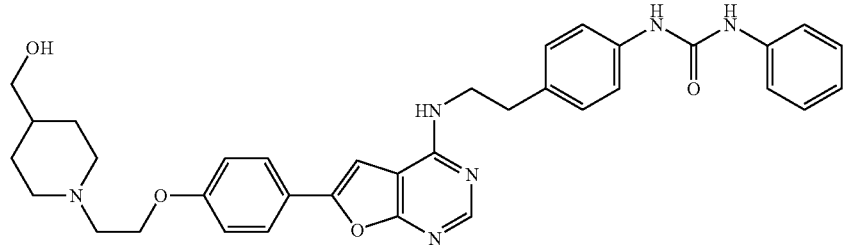
Compound 236
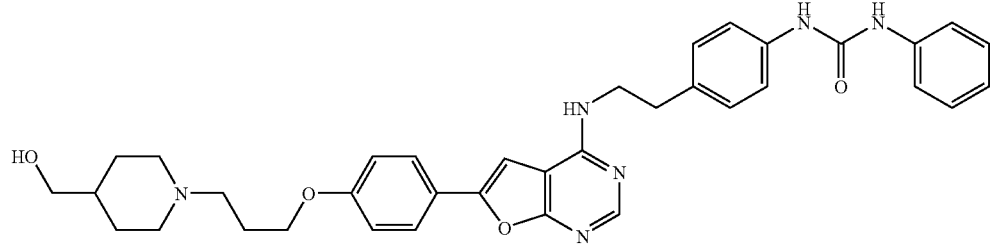
Compound 237
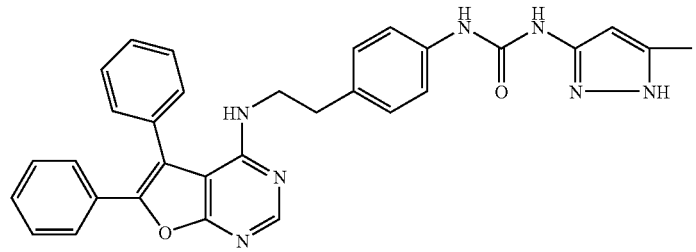
Compound 238
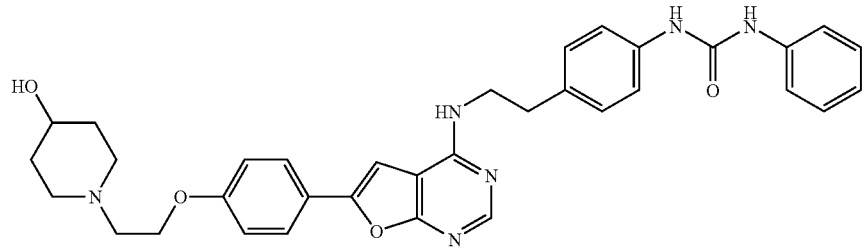
Compound 239
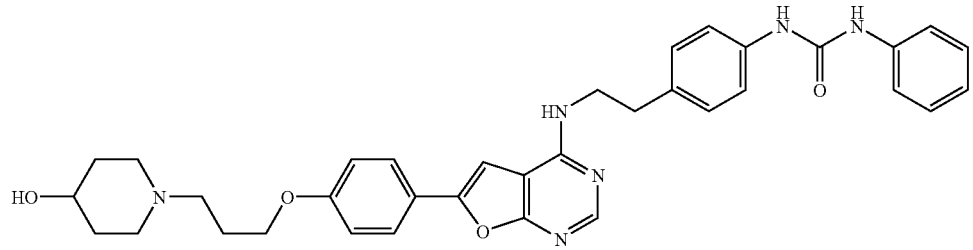
Compound 240
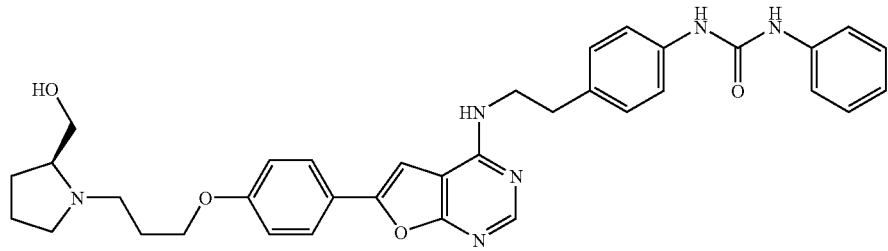
Compound 241

Compound 242
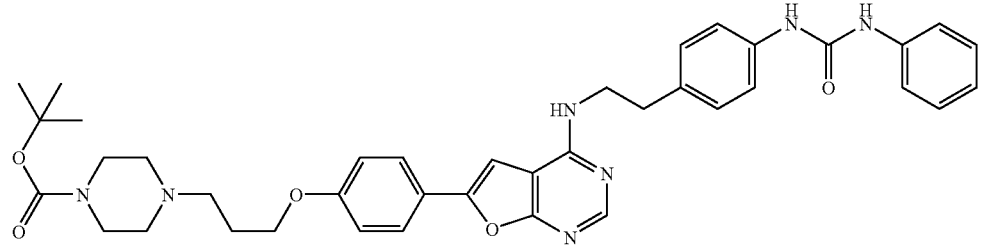
Compound 243
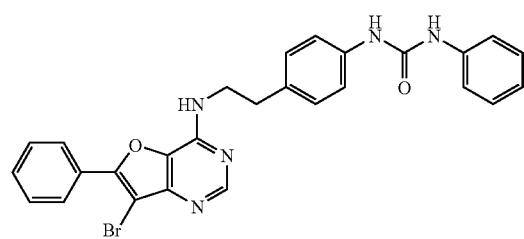
Compound 244
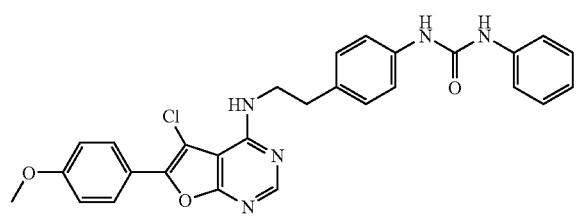
Compound 245
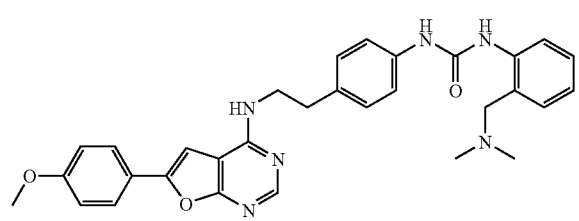
Compound 246
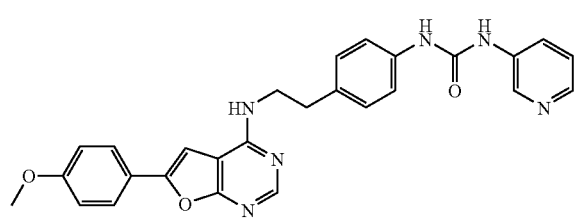
Compound 247
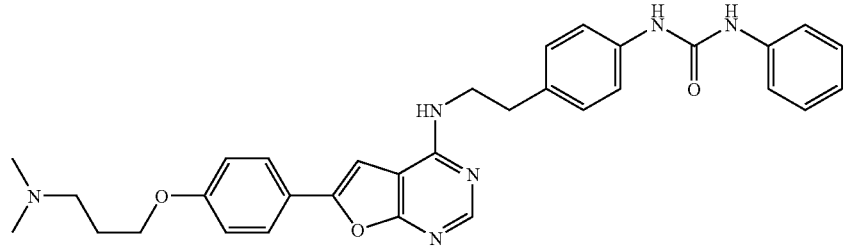
Compound 248
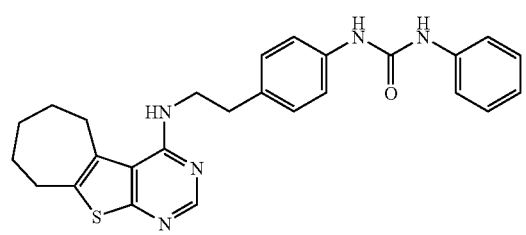
Compound 249
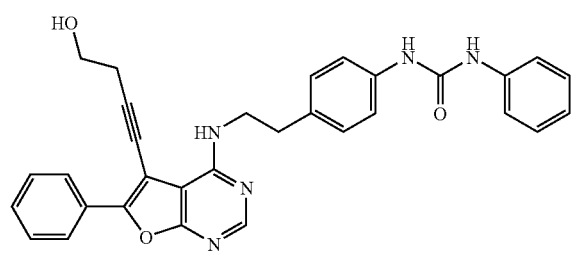
Compound 250
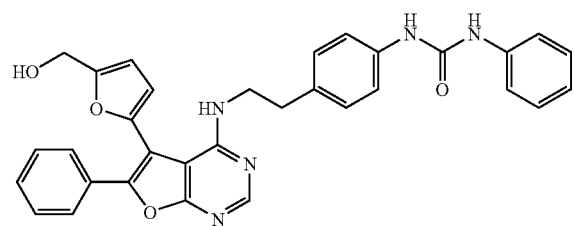
Compound 251
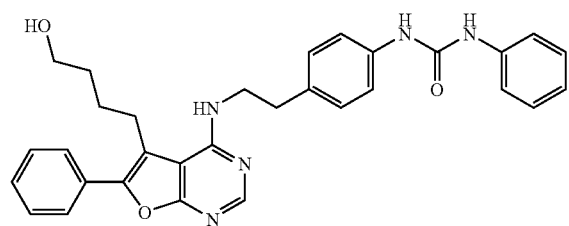

-continued
Compound 252
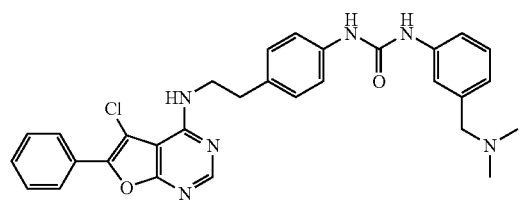
Compound 253
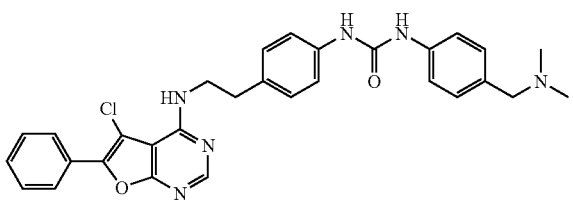
Compound 254
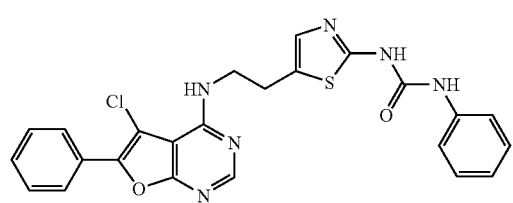
Compound 255
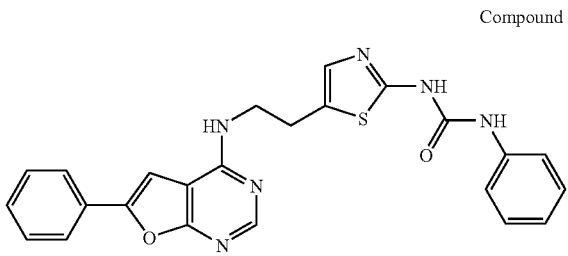
Compound 256
Compound 257
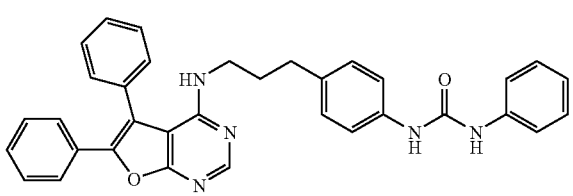
Compound 258
Compound 259
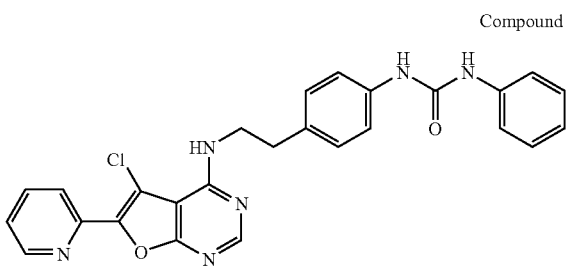
Compound 260
Compound 261
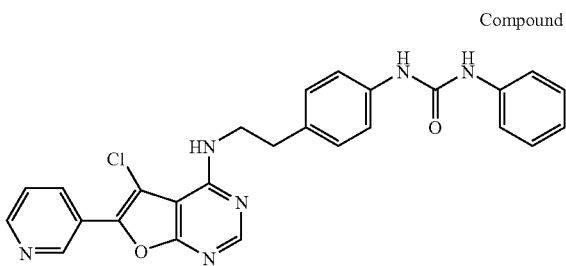
Compound 262
Compound 263
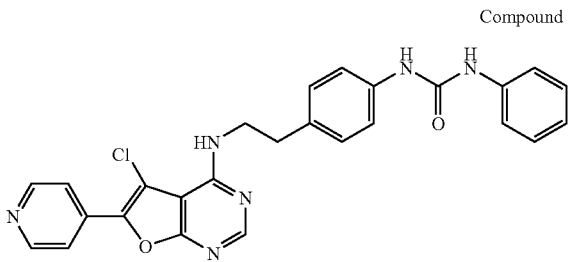

Compound 264

Compound 265

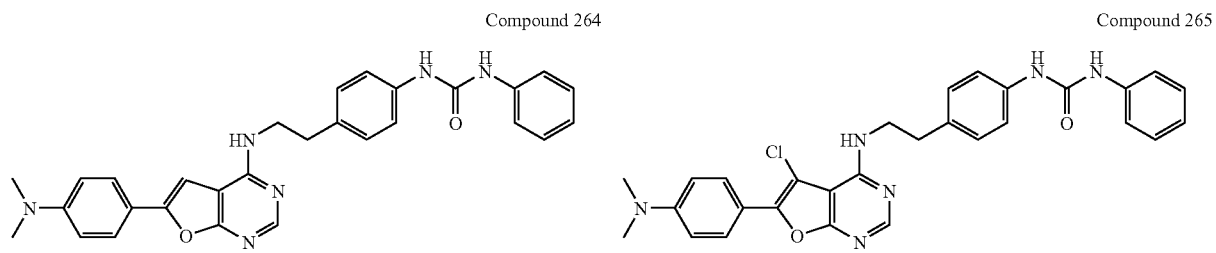

The fused bicyclic pyrimidine compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1 and 2 below show transformations for synthesizing compounds of this invention.

The route shown in Scheme 1 exemplifies synthesis of the furanopyrimidine compounds (VIII) of the present invention. To a mixture of appropriately substituted benzoin (I) and malanonitrile (II) in DMF maintained at 0° C., diethylamine is added dropwise over a time of 30 min. The reaction mixture is allowed to stir for 16 h. Water is then added to the reaction mixture. A precipitate thus formed is collected and crystallized in ethanol to give substituted furan (III). To a mixture of furan (III) and formic acid maintained at 0° C., acetic anhydride is added dropwise over a period of 30 min. Then the reaction is maintained at 100° C. for 16 h. Water is then added to the reaction mixture and a precipitate is formed to afford a furanopyrimidinone (IV). A mixture of (IV) and POCl$_3$ is heated at 55-65° C. for 3 h. Water is then added followed by sodium bicarbonate. The resulting mixture is extracted with ethyl acetate. Concentration of the organic layer, followed purification of the residue by column chromatography, affords a chlorine-substituted furanopyrimidine (V). Reaction of (V) with amine (VI) by heating in n-butanol for 16 h affords amino-substituted furanopyrimidine (VII). Compound (VIII) can be synthesized via reacting (VII) with appropriate isocyanates in refluxing dichloromethane or by reacting (VII) with 1,1'-carbonyldiimidazole (CDI) in dichloromethane, followed by reaction with the desired amines or anilines.

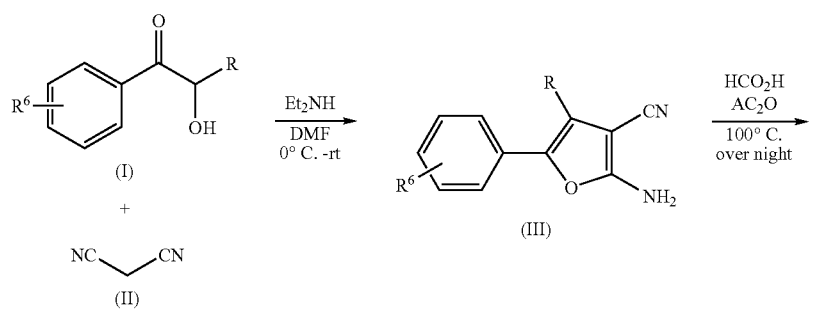

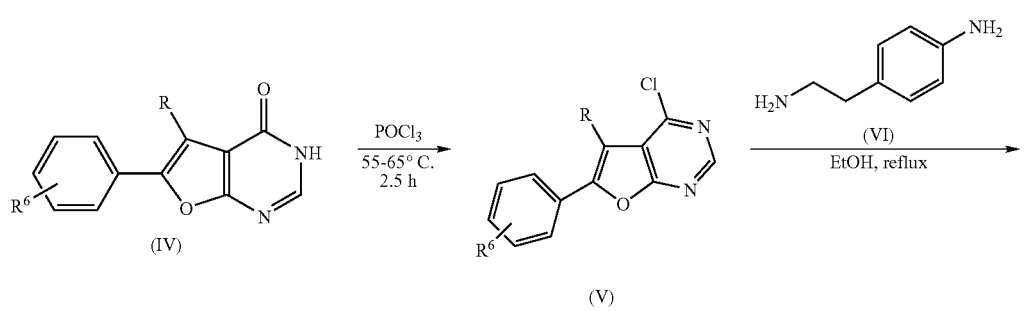

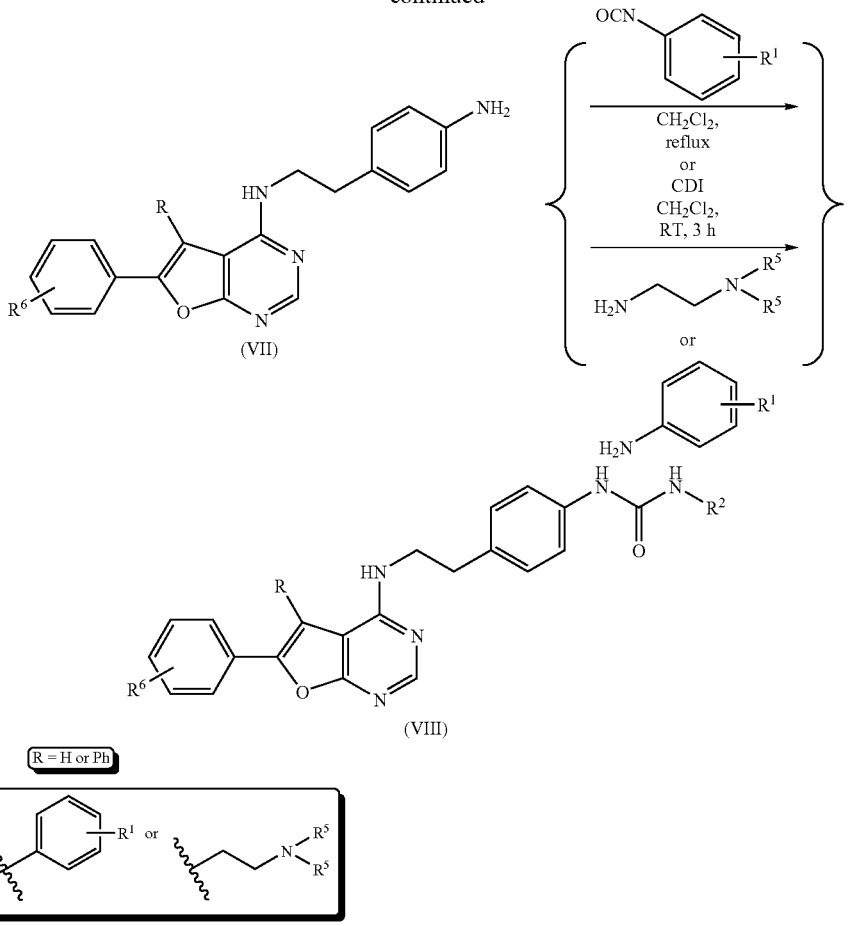

The furanopyrimidine compounds of this invention can also be synthesised by alternative methods. Schemes 2 and 3 below exemplify such alternative synthetic routes.

As shown in Scheme 2 below, bromination of a chloro-substituted furanopyrimidine (IX) using N-bromosuccinimide (NBS) in DMF affords the bromo, chloro-substituted furanopyrimidine (X). Alternative use of N-chlorosuccinimide (NCS) can afford the corresponding chloro derivative of (X). Reaction of (X) with the amine (VI) by refluxing in ethanol gives bromo, amino-substituted furanopyrimidine (XI). Compound (XII) is then synthesized by reacting (XI) with appropriate isocyanates in refluxing dichloromethane or by reacting (XI) with 1,1'-carbonyldiimidazole (CDI) in dichloromethane, followed by reaction with the desired amines or anilines. Furanopyrimidine compound (XIII) of this invention can be synthesized under standard Suzuki coupling condition by reacting compound (XII) with appropriate boronic acid, in the presence of Pd(OAc)$_2$, PPh$_3$, and sodium carbonate in a mixture of water and dioxane under refluxing conditions for 2-3 h. Furanopyrimidine compound (XIV) of this invention can be synthesized under standard Sonagashira coupling condition by reacting compound (XII) with appropriate alkynyl compound, in the presence of Pd(PPh$_3$)$_2$Cl$_2$, PPh$_3$ and diisopropylethyl amine (DIPEA) in DMF at 60° C. for 16 h.

Scheme 2

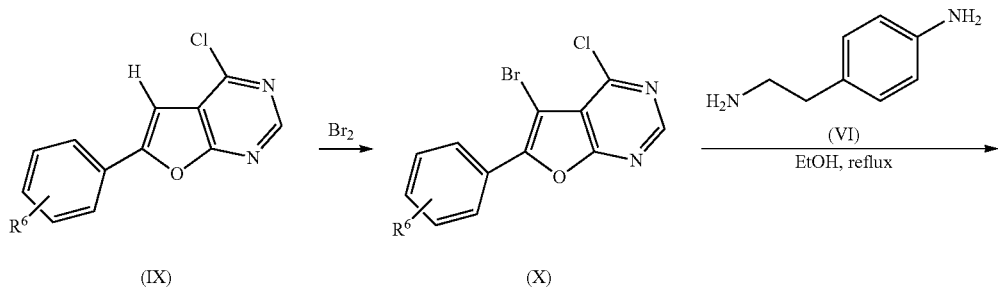

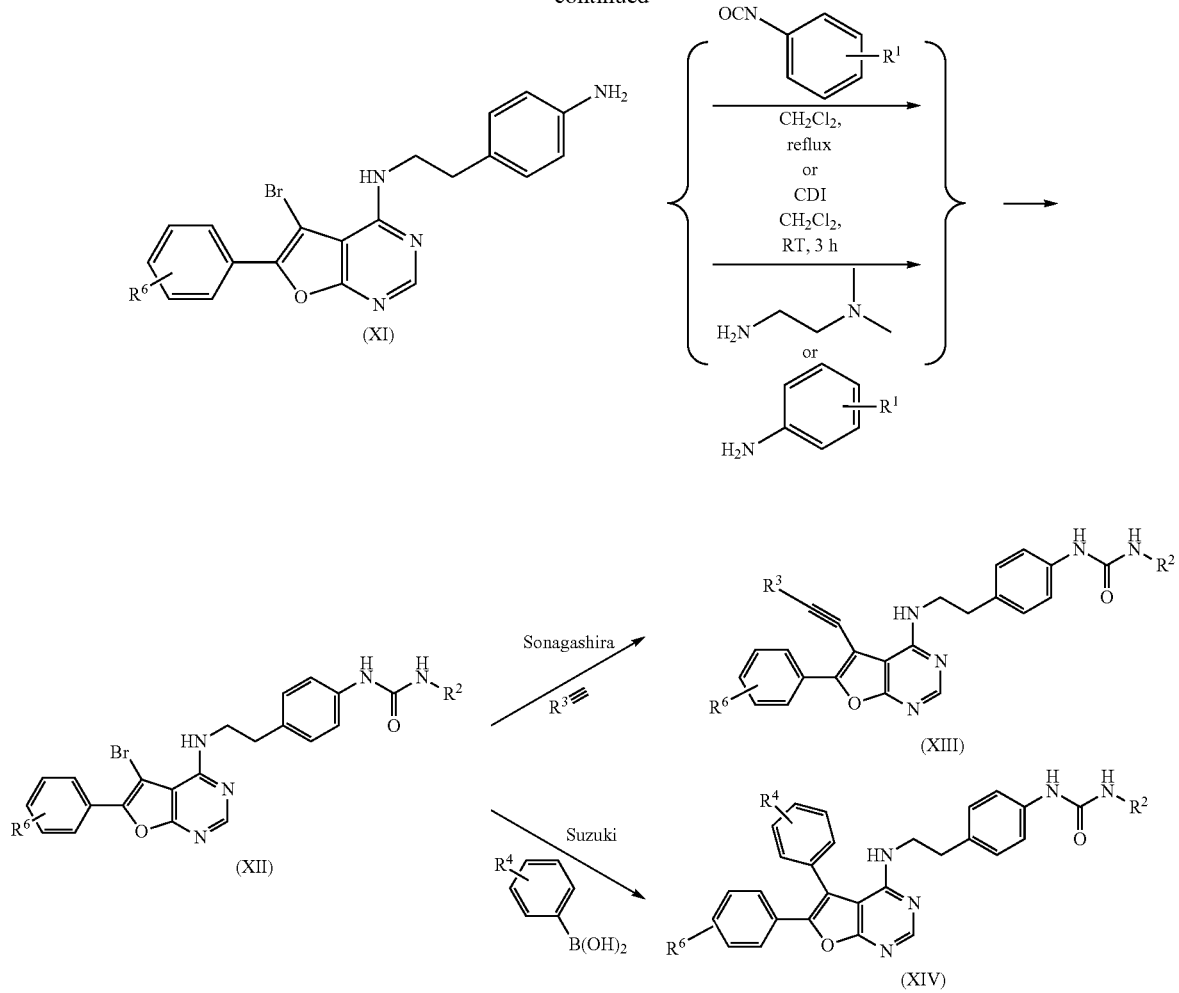

As shown in Scheme 3 below, compound (XV) is reacted with the amine (VI) by refluxing in ethanol to give furanopyrimidine (XVI). Compound (XVII) is then synthesized by reacting (XVI) with an isocyanate of choice in refluxing dichloromethane or by reacting (XVI) with 1,1'-carbonyldiimidazole (CDI) in dichloromethane, followed by a reaction with a desired amine or aniline. Treatment of compound (XVII) with $BBr_3$ in dichloromethane affords demethylated compound (XVIII). This compound is alkylated with bromo-chloro-alkane compound (XIX) and then reacted with amine (XX) of choice to afford the desired product (XXI).

Scheme 3

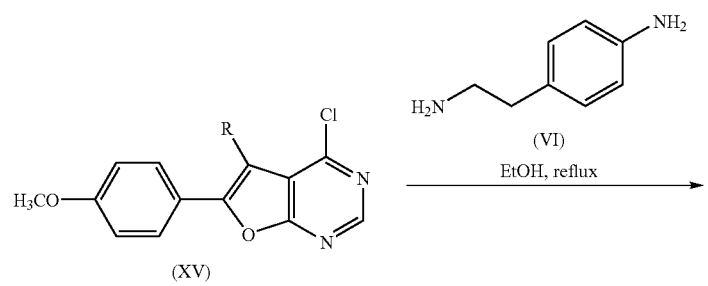

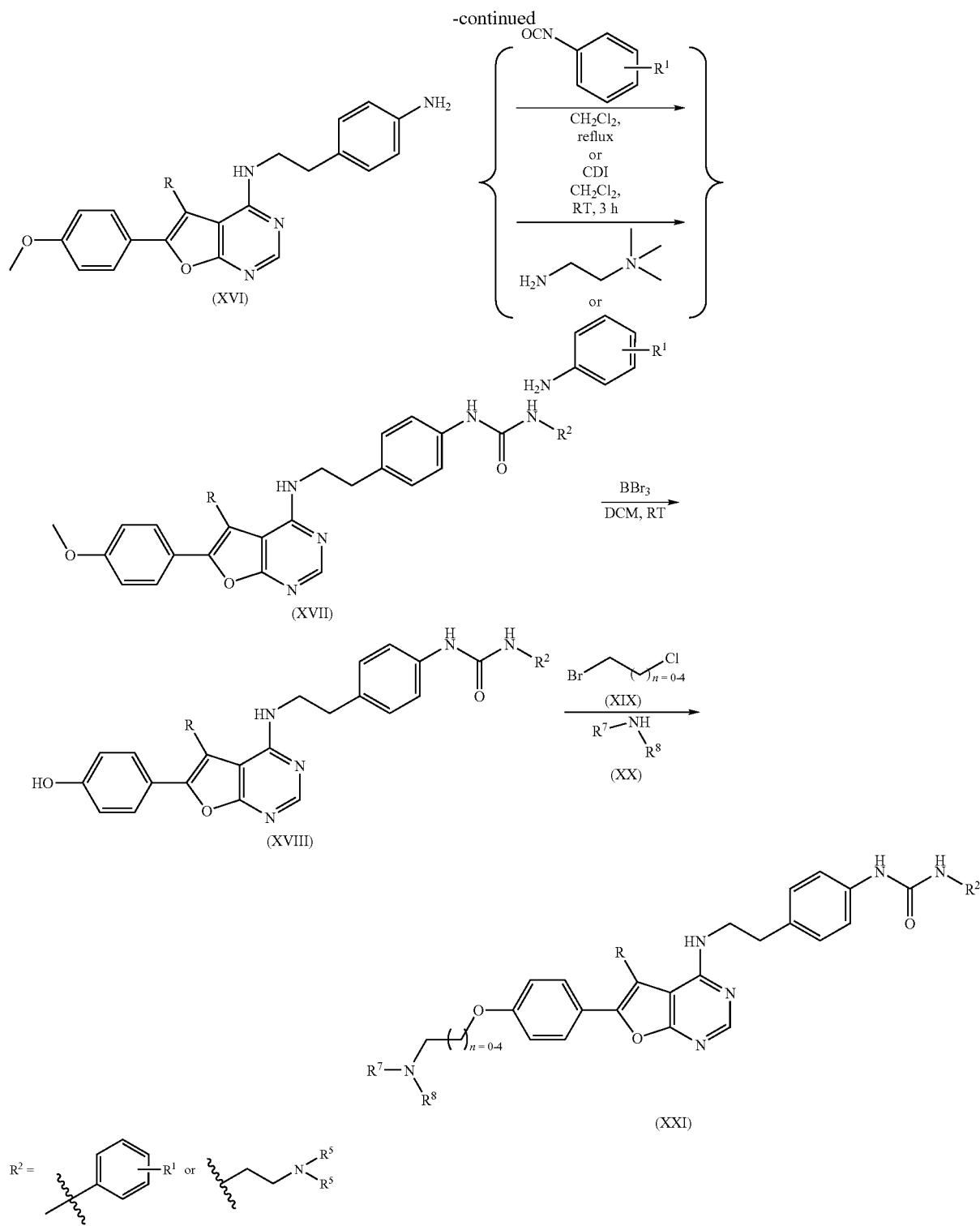

The thienopyrimidine and pyrrolopyrimidine compounds of this invention can also be synthesized in manners similar to those outlined in Schemes 1, 2, and 3 with necessary modifications as recognized by those skilled in the art.

A fused bicyclic pyrimidine compound thus synthesized can be further purified by flash column chromatography, high performance liquid chromatography, crystallization, or any other suitable methods.

Also within the scope of this invention are (1) a pharmaceutical composition that contains an effective amount of at least one of the fused bicyclic pyrimidine compounds of this invention and a pharmaceutically acceptable carrier, and (2) a method for treating an Aurora kinase mediated disorder such as cancer by administering to a subject in need of this treatment an effective amount of such a fused bicyclic pyrimidine compound.

As used herein, the term "treating" refers to administering a fused bicyclic pyrimidine compound to a subject that has an Aurora kinase mediated disorder such as cancer, or has a symptom of or a predisposition toward it, with the purpose to cure, heal, alleviate, relieve, alter, remedy, ameliorate, improve, affect, or reduce the risk of, the disorder, the symptoms of or the predisposition toward the disorder. For example, certain compounds of this invention can be used to reduce the risk of metastasis. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention includes both solid and haematological tumours of various organs. Examples of solid tumors include pancreatic cancer; bladder cancer including urothelium cancer; colorectal cancer; breast cancer, including metastatic breast cancer; male genital tract cancer such as seminal vesicle cancer, testes cancer, germ cell tumors, and prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; uterus cancer; gestational trophoblastic disease such as choriocarcinoma; gastric cancer; bile duct cancer; gallbladder cancer; small intestine cancer; esophageal cancer; oropharyngeal cancer; hypopharyngeal cancer; eye cancer, including, retinoblastoma; nerve cancer, including, Schwannoma, meningioma; neuroblastoma and neuroma; head and neck cancer, including, e.g., squamous cell carcinoma of the head and neck; melanoma; plasmacytoma; endocrine gland neoplasm, including, pituitary adenoma, thyroid cancer, and adrenal tumor; neuroendocrine cancer, including metastatic neuroendocrine tumors; brain tumors, including, e.g., glioma, anaplastic oligodendroglioma, glioblastoma multiforme, and astrocytoma such as adult anaplastic astrocytoma; bone cancer; and sarcomas from soft tissue or bone such as Kaposi's sarcoma. Examples of hematologic malignancy include acute myeloid leukemia (AML) or chloroma; chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma, cutaneous T-cell lymphoma (such as mycosis fungoides), and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. Other cancer types, in which Aurora kinase activity is upregulated/dysregulated, are described in WO 2006/003440 A1, WO 2004/058781, US Patent Publication 2007/0149561, EP 1771450, and Cancer treatment reviews 34, 175-182 (2008).

The compounds of this invention can be administered in conjunction with cytotoxic agents, radiotherapy, or immunotherapy. Non-limiting examples of cytotoxic agents suitable for use in combination with the Aurora kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A fused bicyclic pyrimidine compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents which form more soluble complexes with the fused bicyclic pyrimidine compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the fused bicyclic pyrimidine compounds of this invention in inhibiting activity of Aurora kinase. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Certain compounds of this invention can also inhibit the activities of other protein kinases. For example, Compound 82 inhibits the activities of PLK4, PDGFRB, and FLT3. Therefore, this invention also features a method for inhibiting the activities of protein kinases other than Aurora kinase and a method for treating disorders mediated via such protein kinases by administering to a subject in need of this treatment an effective amount of the fused bicyclic pyrimidine compound described herein. Protein kinases that can be inhibited by the compounds of the invention include but are not limited to AURORA, BCR-ABL, VEGFR, PDGFR, EGFR, FLT3, JAK2, C-ABL, PDK1, CDK, CHK1, LCK, FGFR, RET, C-KIT, C-MET, EPH, SRC, MEK1, RAF, AKT, PI3K, MTOR, PLK, RET, TIE2, AXL, IKK, PIM, and ROCK kinase. Other target protein kinases are described by, e.g., Manning et al., *Science* 2002, 298, 1912 and Noble et al., *Science* 2004, 303, 1800. Diseases that are associated with protein kinases and can be treated by the methods of the invention include but are not limited to cancer, diabetes, inflammation, allergy/asthma, immune diseases, central nervous system diseases, and angiogenesis disorders.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Synthesis of N-(4-aminobenzyl)-5,6-diphenylfuro[2,3-d]pyrimidin-4-amine (Compound 1)

4-Chloro-5,6-diphenylfuro[2,3-d]pyrimidine (0.10 g) and 4-(aminomethyl)aniline (0.05 g) in n-butanol (5 mL) were heated at 80° C. for 16 h. The reaction mixture was concentrated and the residue was partitioned between water and ethyl acetate. The organic layer was concentrated and the residue was purified by silica gel column chromatography using a mixture of dichloromethane:methanol (40:1), to give N-(4-aminobenzyl)-5,6-diphenylfuro[2,3-d]pyrimidin-4-amine (0.09 g, 70%). $^1$H NMR (300 MHz, CDCl$_3$): δ 8.44 (s, 1H), 7.54-7.44 (m, 8H), 7.27-7.25 (m, 2H), 6.93 (d, 2H), 6.10 (d, 2H), 4.87 (t, 1H), 4.51 (d, 2H), 3.65 (brs, 2H). LC-MS (ESI) m/z 393.7 (M+H).

EXAMPLES 2-5

Syntheses of Compounds 2-5

Compounds 2-5 were prepared in a manner similar to that described in Example 1. $^1$H NMR and MS data of these compounds are listed below:

Compound 2: LC-MS (ESI) m/z 394.2 (M+H).

Compound 3: $^1$H NMR (300 MHz, CDCl$_3$): δ 8.42 (s, 1H), 7.47-7.22 (m, 10 H), 6.79 (d, 2H), 6.59 (d, 2H), 4.68 (brt, 1H), 3.69-3.63 (m, 4H), 2.67 (t, 2H).

Compound 4: LC-MS (ESI) m/z 408.2 (M+H).

Compound 5: $^1$H NMR (400 MHz, CDCl$_3$): δ 8.44 (s, 1H), 7.90 (d, J=8.0 Hz, 2H), 7.79 (bs, 1H), 7.23~7.60 (m, 15H), 7.02 (d, J=8.0 Hz, 2H), 4.67 (bt, J=5.2 Hz, 1H), 3.72 (q, J=6.4 Hz, 2H), 2.80 (t, J=6.4 Hz, 2H); LC-MS (ESI) m/z 511.2 (M+H).

EXAMPLE 6

Synthesis of 1-(4-(2-(5,6-diphenylfuro[2,3-d]pyrimidin-4-ylamino)ethyl)phenyl)-3-phenylurea (Compound 6)

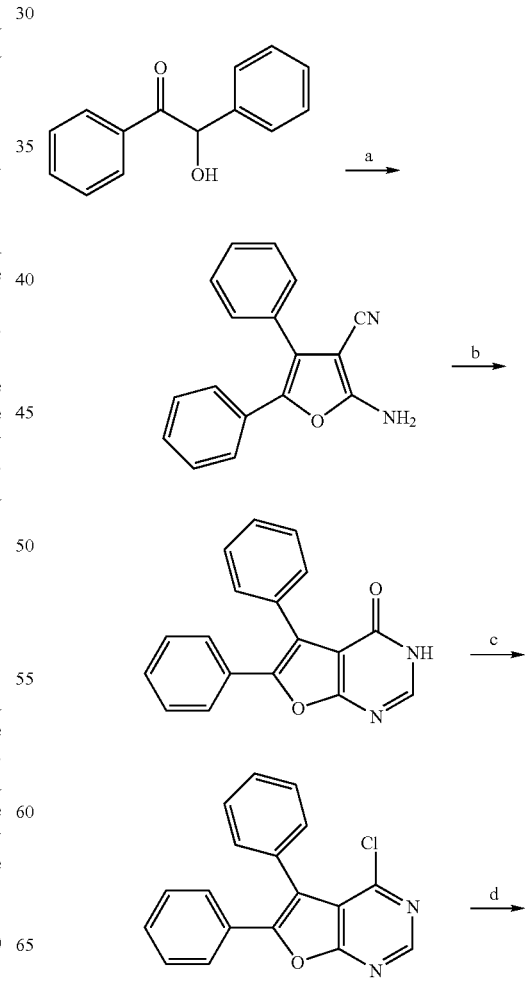

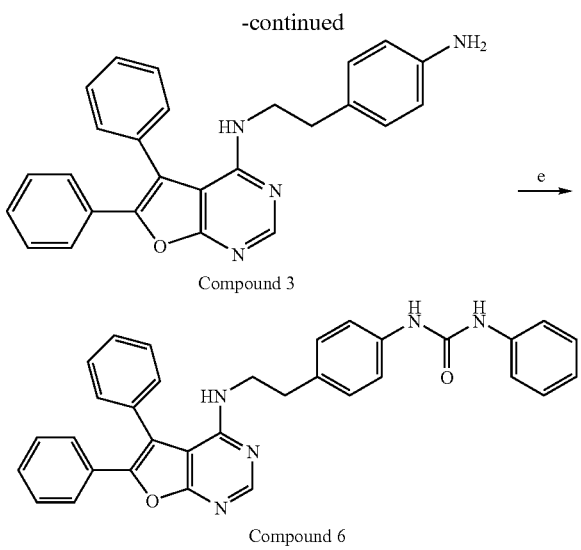

Compound 3

Compound 6

2-Amino-4,5-diphenylfuran-3-carbonitrile (step a): Diethylamine (13.8 g) was added dropwise over a period of 30 min to a mixture of benzoin (10 g) and malononitrile (3.8 g) in DMF (30 ml) at 0° C. (the reaction temperature should not exceed 40° C.). After the resulting mixture was stirred at room temperature for 16 h, water (100 mL) was added. The resulting precipitate was filtered, washed with sufficient amount of water, then with hexanes, and dried. The solid was recrystallized from ethanol to provide yellowish-brown solid product of 2-amino-4,5-diphenylfuran-3-carbonitrile (6 g, 49%). $^1$H NMR (300 MHz, CDCl$_3$): δ 7.47-7.34 (m, 8H), 7.28-7.18 (m, 2H), 4.94 (br, 2H). LC-MS (ESI) m/z 261.1 (M+H).

5,6-Diphenylfuro[2,3-d]pyrimidin-4(3H)-one (step b): A mixture of 2-amino-4,5-diphenylfuran-3-carbonitrile (2.0 g) and formic acid (24 mL) was cooled to 0° C. and acetic anhydride (24 mL) was added dropwise. The resulting mixture was stirred for 1 h. The reaction mixture was then warmed to 100° C. and stirred for 16 h. The reaction mixture was cooled and water was added (40 mL). The precipitated was filtered and washed thoroughly with water and hexanes to give 5,6-diphenylfuro[2,3-d]pyrimidin-4(3H)-one (2.1 g, 95%). $^1$H NMR (300 MHz, CDCl$_3$): δ 7.94 (s, 1H), 7.56-7.52 (m, 4H), 7.46-7.43 (m, 3H), 7.32-7.28 (m, 3H), 7.22 (s, 1H). LC-MS (ESI) m/z 289.1 (M+H).

4-Chloro-5,6-diphenylfuro[2,3-d]pyrimidine (step c): A mixture of 5,6-diphenylfuro[2,3-d]pyrimidin-4(3H)-one (3 g) and POCl$_3$ (30 mL) was heated at 55-65° C. for 3 h. Water was then added followed by sodium bicarbonate. The resulting mixture was extracted with ethyl acetate. The organic layer was concentrated and the crude compound was purified by silica gel column chromatography using a mixture of hexanes:ethyl acetate (95:5), to give white solid 4-chloro-5,6-diphenylfuro[2,3-d]pyrimidine (2 g, 63%). $^1$H NMR (300 MHz, CDCl$_3$): δ 8.77 (s, 1H), 7.61-7.58 (m, 2H), 7.52-7.46 (m, 5H), 7.35-7.32 (m, 3H). LC-MS (ESI) m/z 307.0 (M+H).

N-(4-aminophenethyl)-5,6-diphenylfuro[2,3-d]pyrimidin-4-amine (step d, Compound 3): 4-Chloro-5,6-diphenylfuro[2,3-d]pyrimidine (0.200 g) and 4-(2-aminoethyl)aniline (0.107 g) in n-butanol (5 mL) were heated at 80° C. for 16 h. The reaction mixture was concentrated and the residue was partitioned between water and ethyl acetate. The organic layer was concentrated and the crude compound was purified by silica gel column chromatography using a mixture of dichloromethane:methanol (40:1), to give N-(4-aminophenethyl)-5,6-diphenylfuro[2,3-d]pyrimidin-4-amine (0.195 g, 74%).

1-(4-(2-(5,6-Diphenylfuro[2,3-d]pyrimidin-4-ylamino)ethyl)phenyl)-3-phenylurea (step e, Compound 6): To a solution of N-(4-aminophenethyl)-5,6-diphenylfuro[2,3-d]pyrimidin-4-amine (0.195 g) in acetonitrile (10 mL) was added phenyl isocyanate (0.063 g). After stirring at room temperature for 16 h, the reaction mixture was concentrated and the residue was partitioned between water and ethyl acetate. The organic layer was concentrated and the crude compound was purified by silica gel column chromatography using a mixture of hexanes:ethyl acetate (1:1), to give 1-(4-(2-(5,6-diphenylfuro[2,3-d]pyrimidin-4-ylamino)ethyl)phenyl)-3-phenylurea (0.240 g, 95%). $^1$H-NMR (CDCl$_3$, 300 MHz): δ 8.42 (s, 1H), 7.58 (brs, 1H), 7.43-7.39 (m, 5H), 7.33-7.18 (m, 11H), 7.03-6.98 (m, 1H), 6.86-6.83 (m, 2H), 4.67 (t, 1H), 3.63 (q, 2H), 2.66 (t, 2H). LC-MS (ESI) m/z 526.2 (M+H).

EXAMPLES 7-41

Syntheses of Compounds 7-41

Compounds 7-41 were prepared in a manner similar to that described in Example 6. $^1$H NMR and MS data of these compounds are listed below:

Compound 7: $^1$H-NMR (CDCl$_3$, 400 MHz): δ 8.42 (s, 1H), 7.38~7.47 (m, 5H), 7.28~7.32 (m, 2H), 7.18~7.25 (m, 5H), 6.97 (d, J=8.4 Hz, 2H), 4.79 (bs, 2H), 4.65 (bt, J=5.6 Hz, 1H), 3.69 (q, J=6.4 Hz, 2H), 2.75 (t, J=6.4 Hz, 2H); LC-MS (ESI) m/z 450.2 (M+H).

Compound 8: $^1$H-NMR (CDCl$_3$, 400 MHz): δ 8.43 (s, 1H), 7.39~7.49 (m, 6H), 7.30~7.33 (m, 2H), 7.23~7.27 (m, 2H), 7.18 (d, J=8.0 Hz, 2H), 6.95 (d, J=8.0 Hz, 2H), 6.31 (bs, 1H), 4.67 (bq, J=4.8 Hz, 1H), 4.65 (bt, J=5.6 Hz, 1H), 3.69 (q, J=6.4 Hz, 2H), 2.86 (d, J=4.8 Hz, 3H), 2.75 (t, J=6.4 Hz, 2H); LC-MS (ESI) m/z 464.2 (M+H).

Compound 9: $^1$H-NMR (CDCl$_3$, 400 MHz): δ 8.43 (s, 1H), 7.40~7.50 (m, 5H), 7.23~7.31 (m, 7H), 6.92 (d, J=8.4 Hz, 2H), 6.28 (bs, 1H), 4.66 (bt, J=5.2 Hz, 1H), 3.69 (q, J=6.4 Hz, 2H), 3.05 (s, 6H), 2.74 (t, J=6.4 Hz, 2H); LC-MS (ESI) m/z 478.2 (M+H).

Compound 10: $^1$H-NMR (CDCl$_3$, 400 MHz): δ 8.42 (s, 1H), 7.37~7.48 (m, 6H), 7.23~7.32 (m, 9H), 7.17 (d, J=8.4 Hz, 2H), 6.93 (d, J=8.4 Hz, 2H), 6.37 (bs, 1H), 5.05 (bt, J=5.6 Hz, 1H), 4.64 (bt, J=5.2 Hz, 1H), 4.46 (d, J=5.6 Hz, 2H), 3.67 (q, J=6.4 Hz, 2H), 2.73 (t, J=6.4 Hz, 2H); LC-MS (ESI) m/z 540.2 (M+H).

Compound 11: $^1$H-NMR (CDCl$_3$, 400 MHz): δ 8.40 (s, 1H), 7.27~7.45 (m, 11H), 7.16~7.24 (m, 4H), 7.09 (t, J=7.2 Hz, 1H), 6.94~7.01 (m, 2H), 6.72 (d, J=7.6 Hz, 1H), 4.68 (bt, J=5.6 Hz, 1H), 3.67 (q, J=6.4 Hz, 2H), 2.72 (t, J=6.4 Hz, 2H); LC-MS (ESI) m/z 526.2 (M+H).

Compound 12: $^1$H-NMR (CDCl$_3$, 400 MHz): δ 8.41 (s, 1H), 7.74 (bs, 1H), 7.65 (bs, 1H), 7.29~7.49 (m, 15H), 7.24~7.26 (m, 2H), 7.04 (s, 1H), 6.93 (d, J=7.6 Hz, 1H), 4.65 (bt, J=5.6 Hz, 1H), 3.71 (q, J=6.4 Hz, 2H), 2.80 (t, J=6.4 Hz, 2H); LC-MS (ESI) m/z 542.2 (M+H).

Compound 13: $^1$H-NMR (CDCl$_3$, 400 MHz): δ 8.43 (s, 1H), 7.75 (bs, 1H), 7.72 (bs, 1H), 7.58~7.63 (m, 1H), 7.32~7.49 (m, 12H), 7.30 (d, J=8.4 Hz, 2H), 7.24~7.26 (m, 2H), 7.05 (d, J=8.4 Hz, 2H), 4.69 (bt, J=5.6 Hz, 1H), 3.72 (q, J=6.4 Hz, 2H), 2.80 (t, J=6.4 Hz, 2H); LC-MS (ESI) m/z 542.2 (M+H).

Compound 14: $^1$H-NMR (CDCl$_3$, 300 MHz): δ 8.42 (s, 1H), 7.54-7.47 (m, 1H), 7.47-7.37 (m, 5H), 7.31-7.27 (m, 3H), 7.24-7.17 (m, 5 H), 7.04-7.01 (m, 1 H), 6.93-6.90 (m, 2 H), 6.76-6.69 (m, 1 H), 4.68 (t, 1 H), 4.66 (q, 2 H), 2.71 (t, 2 H).

Compound 15: $^1$H-NMR (CDCl$_3$, 300 MHz): δ 8.42 (s, 1 H), 7.82 (brs, 1 H), 7.72 (brs, 1 H), 7.64-7.51 (m, 1 H), 7.44-7.37 (m, 5 H), 7.30-7.26 (m, 3 H), 7.22-7.17 (m, 5 H), 7.14-7.09 (m, 1 H), 6.96-6.93 (m, 1 H), 6.88-6.85 (m, 2 H), 4.69 (t, 1 H), 3.64 (q, 2 H), 2.68 (t, 2 H).

Compound 16: $^1$H-NMR (CDCl$_3$, 300 MHz): δ 8.41 (s, 1 H), 7.89 (brs, 1 H), 7.81 (brs, 1 H), 7.62-7.57 (m, 1 H), 7.51-7.50 (m, 1 H), 7.43-7.36 (m, 5 H), 7.30-7.23 (m, 2 H), 7.20-7.17 (m, 5 H), 7.10-7.03 (m, 2 H), 6.87-6.84 (m, 2 H), 4.69 (t, 1 H), 3.63 (q, 2 H), 2.67 (t, 2 H).

Compound 17: $^1$H-NMR (CDCl$_3$, 300 MHz): δ 8.43 (s, 1H), 7.38~7.49 (m, 9H), 7.35 (d, J=8.0 Hz, 2H), 7.20~7.32 (m, 6H), 6.98 (d, J=8.0 Hz, 2H), 6.93 (bs, 1H), 4.65 (bt, J=5.6 Hz, 1H), 3.70 (q, J=6.4 Hz, 2H), 2.77 (t, J=6.4 Hz, 2H); LC-MS (ESI) m/z 527.2 (M+H).

Compound 18: $^1$H-NMR (CDCl$_3$, 300 MHz): δ 8.46 (s, 1H), 7.25~7.51 (m, 15H), 7.03~7.16 (m, 4H), 4.68 (t, J=5.4 Hz, 1H), 3.73 (q, J=6.0 Hz, 2H), 2.82 (t, J=6.3 Hz, 2H); LC-MS (ESI) m/z 527.2 (M+H).

Compound 19: $^1$H-NMR (CDCl$_3$, 400 MHz): δ 8.42 (s, 1H), 7.40~7.49 (m, 6H), 7.30~7.33 (m, 2H), 7.23~7.26 (m, 2H), 7.21 (d, J=8.4 Hz, 2H), 6.96 (d, J=8.4 Hz, 2H), 6.53 (bs, 1H), 5.26 (bt, J=5.6 Hz, 1H), 4.66 (bt, J=5.2 Hz, 1H), 3.59~3.72 (m, 6H), 2.75 (t, J=6.4 Hz, 2H). LC-MS (ESI) m/z 512.2 (M+H).

Compound 20: LC-MS (ESI) m/z 563.2 (M+H).
Compound 21: LC-MS (ESI) m/z 563.2 (M+H).
Compound 22: $^1$H NMR (300 MHz, CDCl$_3$): δ 8.42 (s, 1H), 7.49–7.41 (m, 5H), 7.32-7.22 (m, 7H), 7.02-6.87 (m, 6H), 6.46 (brs, 1H), 4.67 (t, 1H), 3.69-3.66 (m, 6H), 3.17-3.13 (m, 4H), 2.74 (t, 2H); LC-MS (ESI) m/z 612.7 (M+H).

Compound 23: LC-MS (ESI) m/z 586.1 (M+H).
Compound 24: $^1$H-NMR (CD$_3$OD, 300 MHz): δ 8.42 (s, 1 H), 7.26-7.45 (m, 8 H), 7.17-7.14 (m, 2 H), 7.05-7.00 (m, 3 H), 6.90-6.93 (m, 2 H), 6.74-6.71 (m, 2 H), 3.75 (t, 2 H), 2.86 (t, 2 H); LC-MS (ESI) m/z 558.3 (M+H).

Compound 25: LC-MS (ESI) m/z 467.1 (M+H).
Compound 26: LC-MS (ESI) m/z 408.1 (M+H).
Compound 27: $^1$NMR (400 MHz, CDCl$_3$): δ 8.51 (s, 1H), 7.28~7.59 (m, 10H), 6.73 (d, J=8.4 Hz, 2H), 6.53 (d, J=8.4 Hz, 2H), 4.55 (t, J=6.4 Hz, 2H), 3.56 (bs, 2H), 2.82 (t, J=6.4 Hz, 2H). 8.52 (s, 1H), 7.28~7.57 (m, 14H), 7.15 (d, J=8.4 Hz, 2H), 7.07~7.12 (m,1H), 6.86 (d, J=8.4 Hz, 2H), 6.59 (bs, 1H), 6.55 (bs, 1H), 4.59 (t, J=6.4 Hz, 2H), 2.89 (t, J=6.4 Hz, 2H); LC-MS (ESI) m/z 527.2 (M+H).

Compound 28: LC-MS (ESI) m/z 540.2 (M+H).
Compound 29: LC-MS (ESI) m/z 594.1 (M+H).
Compound 30: LC-MS (ESI) m/z 551.1 (M+H).
Compound 31: LC-MS (ESI) m/z 568.2 (M+H).
Compound 32: LC-MS (ESI) m/z 571.1 (M+H).
Compound 33: $^1$H NMR (300 MHz, CDCl$_3$): δ 8.42 (s, 1H), 7.50-7.39 (m, 5H), 7.31-7.23 (m, 8H), 6.94 (s, 1H), 6.91 (s, 1H), 6.32 (s, 1H), 4.65 (t, 1H), 3.68 (dd, 2H), 3.53 (t, 4H), 2.73 (t, 2H), 2.47 (t, 4H), 2.34 (s, 3H).

Compound 34: $^1$H NMR (300 MHz, CDCl$_3$): δ 8.42 (s, 1H), 7.50-7.40 (m, 5H), 7.31-7.23 (m, 8H), 6.94 (s, 1H), 6.92 (s, 1H), 6.35 (s, 1H), 4.64 (t, 1H), 3.71-3.64 (m, 4H), 3.54 (t, 4H), 2.73 (t, 2H), 2.64-2.56 (m, 6H); LC-MS (ESI) m/z 585.7 (M+Na).

Compound 35: $^1$H NMR (300 MHz, CDCl$_3$): δ 8.42 (s, 1H), 7.50-7.38 (m, 5H), 7.31-7.23 (m, 11H), 6.95 (s, 1H), 6.92 (s, 1H), 6.33 (s, 1H), 4.65 (t, 1H), 3.67-3.71 (m, 4H), 3.55-3.49 (m, 6H), 2.74 (t, 2H); LC-MS (ESI) m/z 633.7 (M+Na).

Compound 36: LC-MS (ESI) m/z 476.1 (M+H).
Compound 37: LC-MS (ESI) m/z 566.2 (M+H).
Compound 38: LC-MS (ESI) m/z 576.1 (M+H).
Compound 39: LC-MS (ESI) m/z 576.1 (M+H).
Compound 40: LC-MS (ESI) m/z 556.1 (M+H).
Compound 41: $^1$H NMR (400 MHz, CDCl$_3$): δ 8.42 (s, 1H), 7.35~7.48 (m, 11H), 7.23~7.30 (m, 6H), 7.01 (bs, 1H), 6.91 (d, J=8.4 Hz, 2H), 4.61 (bt, J=6.0 1H), 3.77 (s, 2H), 3.68 (q, J=6.4 Hz, 2H), 2.73 (t, J=6.4 Hz, 2H). LC-MS (ESI) m/z 525.2 (M+H).

EXAMPLE 42

Synthesis of N-phenyl-N'-4-[2-(5,6,7,8-tetrahydrobenzo[4,5]thieno[2,3-d]pyrimidin-4-ylamino)ethyl]phenylurea (Compound 42)

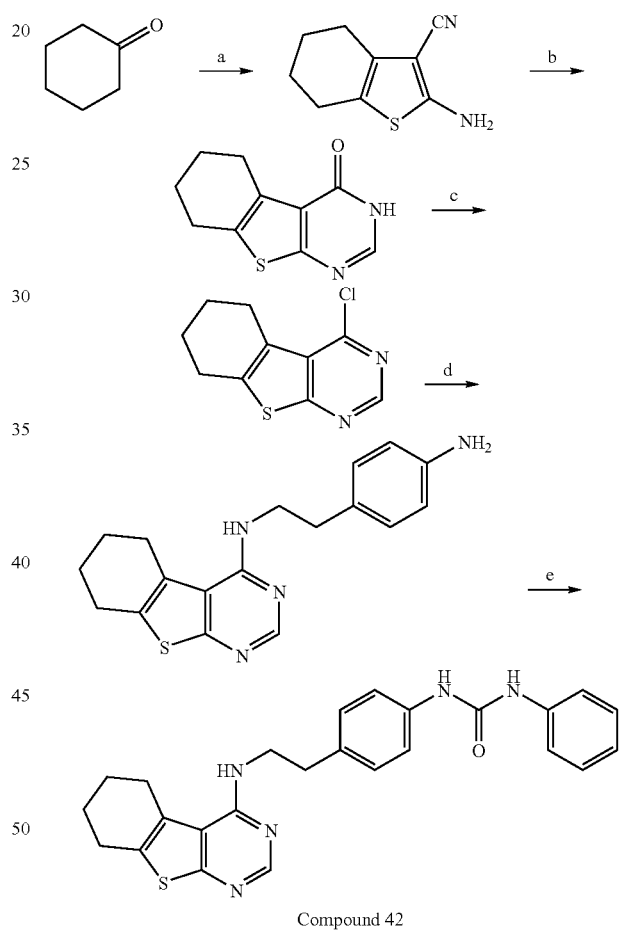

Compound 42

2-Amino-4,5,6,7-tetrahydrobenzo[b]thiophen-3-yl cyanide (step a): To a mixture of cyclohexanone (1.18 g), malononitrile (0.66 g) and sulphur (0.40 g) in absolute ethanol (3 ml) was added triethylamine (2 mL). After refluxed for 16 h, the reaction mixture was concentrated and the residue was partitioned between water and ethyl acetate. The organic layer was concentrated and the crude compound was purified by silica gel column chromatography using a mixture of hexanes:ethyl acetate (4:1), to give 2-amino-4,5,6,7-tetrahydrobenzo[b]thiophen-3-yl cyanide (0.94 g, 44%).

3,4,5,6,7,8-Hexahydrobenzo[4,5]thieno[2,3-d]pyrimidin-4-one (step b): To a mixture of 2-amino-4,5,6,7-tetrahydrobenzo[b]thiophen-3-yl cyanide (0.9 g) and formic acid (10 mL) was added 0.1 mL HCl. After refluxed for 16 h, the reaction mixture was cooled and water (20 mL) was added. The precipitated was filtered and washed thoroughly with water and hexanes to give 3,4,5,6,7,8-hexahydrobenzo[4,5]thieno[2,3-d]pyrimidin-4-one (0.8 g, 77%). $^1$H NMR (300 MHz, CDCl$_3$): δ 7.91 (s, 1H), 3.03-3.00 (m, 2H), 2.80-2.77 (m, 2H), 1.89-1.83 (m, 4H).

4-Chloro-5,6,7,8-tetrahydrobenzo[4,5]thieno[2,3-d]pyrimidine (step c): A mixture of 3,4,5,6,7,8-hexahydrobenzo[4,5]thieno[2,3-d]pyrimidin-4-one (0.8 g) and POCl$_3$ (10 mL) was heated at 55-65° C. for 3 h. Water was then added followed by sodium bicarbonate. The resulting mixture was extracted with ethyl acetate. The organic layer was concentrated and the crude compound was purified by silica gel column chromatography using a mixture of hexanes:ethyl acetate (20:1), to give 4-chloro-5,6,7,8-tetrahydrobenzo[4,5]thieno[2,3-d]pyrimidine (0.52 g, 60%). $^1$H NMR (300 MHz, CDCl$_3$): δ 8.69 (s, 1H), 3.10-3.07 (m, 2H), 2.88-2.86 (m, 2H), 1.89-1.92 (m, 4H). LC-MS (ESI) m/z 225.3 (M+H).

N-4-(4-Aminophenethyl)-5,6,7,8-tetrahydrobenzo[4,5]thieno[2,3-d]pyrimidin-4-amine (step d): A mixture of 4-chloro-5,6,7,8-tetrahydrobenzo[4,5]thieno[2,3-d]pyrimidine (0.075 g) and 4-(2-aminoethyl)aniline (0.055 g) in n-butanol (1 mL) was heated at 80° C. for 16 h. The reaction mixture was concentrated and the residue was partitioned between water and ethyl acetate. The organic layer was concentrated and the crude compound was purified by silica gel column chromatography using a mixture of dichloromethane:methanol (20:1), to give N-4-(4-aminophenethyl)-5,6,7,8-tetrahydrobenzo[4,5]thieno[2,3-d]pyrimidin-4-amine (0.088 g, 81%). $^1$H NMR (300 MHz, CDCl$_3$): δ 8.38 (s, 1H), 7.02 (d, 2H), 6.67 (d, 2H), 5.30 (brs, 1H), 3.77 (t, 2H), 2.86 (t, 2H), 2.76-2.59 (m, 4H), 1.81-1.83 (m, 4H). LC-MS (ESI) m/z 325.5 (M+H).

N-Phenyl-N'-4-[2-(5,6,7,8-tetrahydrobenzo[4,5]thieno[2,3-d]pyrimidin-4-ylamino)ethyl]phenylurea (step e, Compound 42): To N-4-(4-aminophenethyl)-5,6,7,8-tetrahydrobenzo[4,5]thieno[2,3-d]pyrimidin-4-amine (0.085 g) in dichloromethane (3 mL) was added phenyl isocyanate (0.04 g). The resulting mixture was stirred at room temperature for 16 h. The precipitate was filtered and washed well with dichloromethane to give N-phenyl-N'-4-[2-(5,6,7,8-tetrahydrobenzo[4,5]thieno[2,3-d]pyrimidin-4-ylamino)ethyl]phenylurea (0.075 g, 65%). $^1$H NMR (400 MHz, CDCl$_3$): δ 8.38 (s, 1H), 7.34-7.09 (m, 9H), 5.26-5.21 (m, 1H), 3.81 (dd, J=6.4, 12.0 Hz, 2H), 2.93 (t, J=6.8 Hz, 2H), 2.74-2.71 (m, 2H), 2.68-2.61 (m, 2H), 1.84-1.80 (m, 4H). LC-MS (ESI) m/z 444.2 (M+H).

EXAMPLES 43-183

Syntheses of Compounds 43-98, 100, 107, 115, 118, 119, 122-124, 126, 146-148, 151, 152, 160, 161, 163, 164, 171-173, 175, 176, and 196-257

Compounds 43-98, 100, 107, 115, 118, 119, 122-124, 126, 146-148, 151, 152, 160, 161, 163, 164, 171-173, 175, 176, and 196-257 were prepared in a manner similar to that described in Example 6 or 42. $^1$H NMR and MS data of these compounds are listed below.

Compound 43: $^1$H NMR (300 MHz, CDCl$_3$): δ 8.42 (s, 1H), 8.21-8.19 (m, 1H), 7.55-7.40 (m, 6H), 7.36-6.22 (m, 9H), 6.95 (s, 1H), 6.92 (s, 1H), 6.69-6.64 (m, 2H), 6.44 (s, 1H), 4.66 (t, 1H), 3.67 (brs, 8H), 2.74 (t, 2H); LC-MS (ESI) m/z 618.7 (M+Na).

Compound 44: $^1$H NMR (300 MHz, CDCl$_3$): δ 8.42 (s, 1H), 7.50-7.40 (m, 5H), 7.31-7.23 (m, 8H), 6.94 (s, 1H), 6.92 (s, 1H), 6.33 (s, 1H), 4.64 (t, 1H), 3.69-3.64 (m, 4H), 3.55-3.49 (m, 4H), 3.73 (t, 2H), 2.62-2.56 (m, 6H).

Compound 45: $^1$H NMR (300 MHz, CDCl$_3$): δ 8.42 (s, 1H), 7.49-7.39 (m, 5H, 7.32-7.21 (m, 8H), 6.94 (s, 1H), 6.92 (s, 1H), 6.44 (s, 1H), 4.66 (t, 1H), 3.67 (td, 2H), 3.48-3.46 (m, 4H), 2.72 (t, 2H), 1.64 (brs, 6H).

Compound 46: $^1$H NMR (300 MHz, CDCl$_3$): δ 8.42 (s, 1H), 7.49-7.39 (m, 5H), 7.31-7.23 (m, 7H), 6.94 (s, 1H), 6.91 (s, 1H), 6.33 (s, 1H), 4.65 (t, 1H), 3.73-3.61 (m, 8H), 3.55 (t, 4H), 2.73 (t, 2H), 2.66-2.58 (m, 6H); LC-MS (ESI) m/z 629.7 (M+Na).

Compound 47: $^1$H NMR (300 MHz, CDCl$_3$): δ 8.39 (s, 1H), 7.49-7.42 (m, 5H), 7.38-7.34 (m, 2H), 7.26-7.23 (m, 4H), 7.08 (s, 1H), 7.05 (s, 1H), 6.90 (s, 1H), 6.87 (s, 1H), 6.84-6.81 (m, 2H), 6.67 (s, 1H), 6.64 (s, 1H), 5.27 (d, 1H), 4.77-4.75 (m, 1H), 4.69 (t, 1H), 3.72 (s, 3H), 3.66-3.61 (m, 2H), 3.01 (t, 2H), 2.64 (t, 2H); LC-MS (ESI) m/z 628.7 (M+H).

Compound 48: LC-MS (ESI) m/z 615.2 (M+H).
Compound 49: LC-MS (ESI) m/z 577.2 (M+H).
Compound 50: LC-MS (ESI) m/z 592.1 (M+H).
Compound 51: LC-MS (ESI) m/z 573.2 (M+H).
Compound 52: LC-MS (ESI) m/z 584.1 (M+H).
Compound 53: LC-MS (ESI) m/z 570.2 (M+H).
Compound 54: $^1$H NMR (400 MHz, CDCl$_3$): δ 8.41 (s, 1H), 7.42~7.53 (m, 9H), 7.24~7.31 (m, 7H), 7.22 (d, J=8.0 Hz, 2H), 7.08 (d, J=8.0 Hz, 2H), 6.48 (bs, 1H), 5.14 (bt, J=5.6 Hz, 1H), 4.97 (bt, J=5.6 Hz, 1H), 4.61 (d, J=5.6 Hz, 2H), 4.40 (d, J=5.6 Hz, 2H); LC-MS (ESI) m/z 526.2 (M+H).

Compound 55: $^1$H NMR (400 MHz, CDCl$_3$): δ 8.38 (s, 1H), 7.41~7.52 (m, 8H), 7.00~7.28 (m, 11H), 6.64 (bs, 1H), 5.12 (bt, J=5.6 Hz, 1H), 4.99 (bt, J=5.6 Hz, 1H), 4.60 (d, J=5.6 Hz, 2H), 4.37 (d, J=5.6 Hz, 2H); LC-MS (ESI) m/z 526.2 (M+H).

Compound 56: $^1$H NMR (400 MHz, CDCl$_3$): δ 8.42 (s, 1H), 7.45-7.43 (m, 2H), 7.36-7.32 (m, 4H), 7.28-7.15 (m, 9H), 7.04 (t, J=7.6 Hz, 1H), 6.92-6.88 (m, 4H), 4.74 (t, J=6.0 Hz, 1H), 3.84 (s, 3H), 3.68 (dt, J=6.0, 6.0 Hz, 2 H), 2.71 (t, J=6.0 Hz, 2 H),; LC-MS (ESI) of Compound 56: m/z 556 (M+H).

Compound 57: $^1$H NMR (400 MHz, d$_6$-DMSO): δ 8.62 (s, 1H), 8.59 (s, 1H), 8.35 (s, 1H), 7.98 (d, J=8.0 Hz, 2H), 7.57-7.37 (m, 2H), 7.25 (t, J=7.6 Hz, 2H), 7.18 (d, J=7.6 Hz, 2H), 7.00 (t, J=7.6 Hz, 2H), 6.94 (t, J=7.6 Hz, 1H), 3.75 (dt, J=7.2, 7.2 Hz, 2H), 2.87 (t, J=7.2 Hz, 2 H); LC-MS (ESI) m/z 530 (M+2+H), 528 (M+H).

Compound 58: $^1$H NMR (300 MHz, d$_6$-DMSO): 10.15 (s, 1H), 8.64 (s, 1H), 8.56 (s, 1H), 8.36 (s, 1H), 7.43 (d, J=8.4 Hz, 2H), 7.45-7.23 (m, 13H), 6.96 (d, J=8.4 Hz, 2H), 6.95 (t, J=8.4 Hz, 1H), 5.12 (t, J=5.1 Hz, 1H), 3.60 (dt, J=5.1, 5.1 Hz, 2H), 2.68 (t, J=5.1 Hz, 2 H), 2.09 (s, 3H); LC-MS (ESI) m/z 583 (M+H).

Compound 59: $^1$H NMR (400 MHz, CDCl$_3$): 8.42 (s, 1H), 7.79 (brs, 2H), 7.45-7.42 (m, 2H), 7.32-7.29 (m, 3H), 7.21-7.17 (m, 7H), 6.99-6.94 (m, 2H), 6.85-6.82 (m, 4H), 4.78 (t, J=5.6 Hz, 1H), 3.70 (s, 3H), 3.63 (brs, 2H), 2.66 (t, J=5.6 Hz, 2 H); LC-MS (ESI) m/z 556 (M+H).

Compound 60: $^1$H NMR (400 MHz, CDCl$_3$): δ 8.88 (brs, 1H), 8.42 (s, 1H), 7.61 (brs, 1H), 7.58 (brs, 1H), 7.48-7.46 (m, 2H), 7.41 (d, J=7.6 Hz, 2H), 7.31 (t, J=7.6 Hz, 2H), 7.22 (d, J=8.4 Hz, 2H), 7.19-7.16 (m, 3H), 7.11 (t, J=7.6 Hz, 1H), 6.98-6.96 (m, 9H), 6.92 (d, J=8.4 Hz, 1H), 6.73-6.71 (m, 2H), 4.72 (t, J=5.6 Hz, 1H), 3.68 (dt, J=5.6, 5.6 Hz, 2H), 2.73 (t, J=5.6 Hz, 2 H); LC-MS (ESI) m/z 542 (M+H).

Compound 61: ¹H NMR (300 MHz, CDCl₃): δ 8.43 (s, 1H), 7.47-7.39 (m, 5H), 7.34-7.29 (m, 4H), 7.25-7.22 (m, 5H), 7.03-6.93 (m, 4H), 6.88 (s, 1H), 6.85 (s, 1H), 4.67 (t, 1H), 3.71-3.65 (m, 2H), 2.74 (t, 2H); LC-MS (ESI) m/z 544.3 (M+H).

Compound 62: ¹H NMR (300 MHz, CDCl₃): δ 8.40 (s, 1H), 8.06 (s, 1H), 7.90 (s, 1H), 7.44-7.36 (m, 5H), 7.32-7.28 (m, 3H), 7.20-7.14(m, 5H), 6.93-6.83 (m, 4H), 4.71 t, 1H), 3.64-3.58 (m, 2H), 2.65 (t, 2H); LC-MS (ESI) m/z 562.2 (M+H).

Compound 63: ¹H NMR (300 MHz, CDCl₃): δ 8.42 (s, 1H), 7.49-7.39 (m, 6H), 7.31-7.28 (m, 2H), 7.24-7.19 (m, 6H), 7.02-6.98 (m, 2H), 6.94 (d, 2H), 6.49-6.46 (m, 1H), 4.69 (t, 1H), 3.71-3.65 (m, 2H), 2.73 (t, 2H); LC-MS (ESI) m/z 562.3 (M+H).

Compound 64: ¹H NMR (300 MHz, CDCl₃): δ 8.42 (s, 1H), 7.56-7.55 (m, 2H), 7.48-7.40 (m, 6H), 7.32-7.29 (m, 2H), 7.25-7.22 (m, 4H), 7.19-7.16 (m, 2H), 7.12-7.08 (m, 3H), 6.93-6.91 (m, 2H), 4.65 (t, 1H), 3.69-3.65 (m, 2H), 2.72 (t, 2H); LC-MS (ESI) m/z 583.3 (M+H).

Compound 65: ¹H NMR (300 MHz, CDCl₃): δ 8.42 (s, 1H), 7.46-7.37 (m, 5H), 7.30-7.27 (m, 2H), 7.25-7.21 (m, 7H), 7.12 (s, 1H), 6.98 (s, 1H), 6.90-6.83 (m, 4H), 4.66 (t, 1H), 3.85-3.82 (m, 4H), 3.69-3.62 (m, 2H), 3.10-3.07 (m, 4H), 2.70 (t, 2H); LC-MS (ESI) m/z 583.3 (M+H).

Compound 66: LC-MS (ESI) m/z 572.2 (M+H).

Compound 67: ¹H-NMR (300 MHz, CDCl₃): δ 8.42 (s, H),7.36-7.43 (m, 4H), 7.23-7.31 (m, 10H), 4.96-5.00 (t, NH), 4.64-4.67 (t, NH), 3.64-3.70 (q, 2H), 3.20-3.25 (q, 2H), 2.70-2.74 (t, 2H), 1.33-1.57 (m, 2H), 0.91-0.94 (t, 3H); LC-MS (ESI) m/z 492.7 (M+H).

Compound 68: ¹H-NMR (300 MHz, CDCl₃):δ 8.34 (s, H), 7.40-7.47 (m, 4H), 7.25-7.38 (m, 10H), 4.63-4.67 (t, NH), 3.66-3.72 (q, 2H), 3.24-3.29 (q, 2H), 2.27-2.76 (t, 2H), 1.52-1.57 (t, 2H), 1.25-1.29 (m, 4H), 0.88-0.91 (t, 3H); LC-MS (ESI) m/z 518.7 (M+H).

Compound 69: ¹H-NMR (300 MHz, CDCl₃): δ 8.57 (s,H), 7.57-7.62 (m, 4H), 7.39-7.47 (m, 10H), 4.65-5.30 (t, NH), 3.66-3.72 (q, 2H), 3.22-3.29 (q, 2H), 2.72-2.76 (t, 2H), 1.49-1.54 (m, 2H), 1.26-1.29 (m, 6H), 0.85-0.89 (t, 3H); LC-MS (ESI) m/z 532.7 (M+H).

Compound 70: ¹H-NMR (300 MHz, CDCl₃):δ 8.41 (s, H), 7.38-7.46 (m, 4H),7.18-7.31 (m, 10H), 4.07-4.18 (m, H), 3.62-3.69 (q, 2H), 2.68-2.72 (t, 2H), 1.94-2.04 (m, 2H), 1.53-1.77 (m, 4H), 1.32-1.46 (m, 2H), 1.34-1.39 (t, 2H).

Compound 71: ¹H-NMR (300 MHz, CDCl₃):δ 8.56 (s, H), 7.38-7.44 (m, 4H), 7.17-7.30 (m, 10H), 4.64-4.68 (t, NH), 3.60-3.68 (m, 2H), 2.62-2.73 (t, 2H), 1.93-2.17 (m, 1H), 1.56-1.70 (m, 4H), 1.26-1.41 (m, 4H),1.06-1.17 (m, 2H).

Compound 72: ¹H-NMR (300 MHz, CDCl₃):δ 8.42 (s, H) 7.43-7.46 (m, 4H), 7.22-7.41 (m, 10H), 6.88-6.92 (q,4H), 6.61 (s, H), 6.49 (s, H), 3.80 (s, H), 3.67-3.68 (q, 2H), 2.71-2.75 (t, 2H).

Compound 73: ¹H-NMR (300 MHz, CDCl₃):δ 8.40 (s, H),7.28-7.43 (m, 12H), 7.16 (s, H), 6.85-6.90 (d,2H), 6.62 (s, 2H), 5.82-5.84 (d, 2H), 4.64-4.68 (t, H), 3.59-3.66 (q, 2H), 2.64-2.68 (t, 2H).

Compound 74: LC-MS (ESI) m/z 543.0 (M+H).

Compound 75: LC-MS (ESI) m/z 551.2 (M+H).

Compound 76: ¹H NMR (300 MHz, CDCl₃): 9.45 (s, 1H), 8.46 (s, 1H), 7.71-7.68 (m, 1H), 7.47-7.29 (m, 8H), 7.23-7.07 (m, 7H), 6.85 (brs, 1H), 6.68 (brs, 1H), 6.52 (d, J=3.6 Hz, 1H), 3.95 (dt, J=6.6, 6.6 Hz, 2H), 3.01 (t, J=6.6 Hz, 2 H); LC-MS (ESI) m/z 544 (M+H).

Compound 77: ¹H NMR (400 MHz, d₆-DMSO): δ 8.65 (s, 1H), 8.61 (s, 1H), 8.40 (s, 1H), 8.29-8.26 (m, 2H), 7.46-7.44 (m, 2H), 7.37-7.33 (m, 7H), 7.28-7.24 (m, 2H), 7.03 (d, J=8.4 Hz, 2H), 6.97-6.93 (m, 1H), 5.48 (t, J=6.4 Hz, 1H), 3.62 (dt, J=6.4, 6.4 Hz, 2H), 2.73 (t, J=6.4 Hz, 2 H); LC-MS (ESI) m/z 571 (M+H).

Compound 78: ¹H NMR (400 MHz, d₆-DMSO): 9.78 (s, 1H), 8.63 (s, 1H), 8.58 (s, 1H), 8.35 (s, 1H), 7.45-7.24 (m, 12H), 6.97-6.90 (m, 4H), 6.78-6.74 (m, 2H), 5.14 (t, J=6.0 Hz, 1H), 3.61 (dt, J=6.0, 6.0 Hz, 2H), 2.67 (t, J=6.0 Hz, 2 H); LC-MS (ESI) m/z 542 (M+H).

Compound 79: ¹H NMR (300 MHz, d₆-DMSO): 8.62 (s, 1H), 8.59 (s, 1H), 8.28 (s, 1H), 8.10 (brs, 1H), 7.78 (d, J=7.2 Hz, 2H), 7.52-7.37 (m, 8H), 7.28-7.17 (m, 4H), 6.94 (t, J=7.2 Hz, 1H), 3.70 (td, J=7.2, 7.2 Hz, 2 H), 2.87 (t, J=7.2 Hz, 2H); LC-MS (ESI) m/z 450 (M+H).

Compound 80: ¹H NMR (300 MHz, d₆-DMSO): 10.12 (s, 1H), 8.64 (s, 1H), 8.57 (s, 1H), 8.36 (s, 1H), 7.73-7.66 (m, 2H), 7.46-7.24 (m, 12H), 7.02-6.91 (m, 4H), 5.21 (t, J=5.4 Hz, 1H), 3.60 (dt, J=5.4, 5.4 Hz, 2H), 2.67 (t, J=5.4 Hz, 2 H), 2.05 (s, 3H); LC-MS (ESI) m/z 583 (M+H).

Compound 81: ¹H NMR (400 MHz, CDCl₃): 8.40 (s, 1H), 8.18 (d, J=8.0 Hz, 1H), 7.48-7.26 (m, 8H), 7.20 (d, J=8.0 Hz, 2H), 7.10 (t, J=7.2 Hz, 1H), 6.91 (d, J=7.2 Hz, 2H), 6.14 (t, J=5.1 Hz, 1H), 3.86 (dt, J=5.1, 5.1 Hz, 2H), 2.96 (t, J=5.1 Hz, 2 H), 0.27 (s, 9H); LC-MS (ESI) m/z 546 (M+H).

Compound 82: ¹H NMR (300 MHz, CDCl₃): 8.41 (s, 1H), 8.01 (d, J=7.2 Hz, 2H), 7. 51-7.33 (m, 8H), 7.26-7.24 (m, 3H), 7.16-7.11 (m, 1H), 6.50 (s, 1H), 6.48 (s, 1H), 5.89 (t, J=6.6 Hz, 1H), 3.90 (dt, J=6.6, 6.6 Hz, 2H), 2.99 (t, J=6.6 Hz, 2 H); LC-MS (ESI) m/z 484 (M+H).

Compound 83: LC-MS (ESI) m/z 421.1 (M+H).
Compound 84: LC-MS (ESI) m/z 483.1 (M+H).
Compound 85: LC-MS (ESI) m/z 421.1 (M+H).
Compound 86: LC-MS (ESI) m/z 483.1 (M+H).
Compound 87: LC-MS (ESI) m/z 435.2 (M+H).
Compound 88: LC-MS (ESI) m/z 471.1 (M+H).
Compound 89: LC-MS (ESI) m/z 457.1 (M+H).
Compound 90: LC-MS (ESI) m/z 443.1 (M+H).

Compound 91: ¹H NMR (300 MHz, CDCl₃): δ 8.44 (s, 1H), 7.97-7.92 (m, 1H), 7.47-7.38 (m, 6H), 7.34-7.28 (m, 4H), 7.24-7.20 (m, 3H), 7.05-7.02 (m, 1H), 6.97 (s, 1H, NH), 6.94 (s, 1H, NH), 6.84-6.80 (m, 1H), 4.70-4.66 (t, 1H), 3.72-3.66 (q, 2H), 2.76-2.72 (t, 2H); LC-MS (ESI) m/z 562.3 (M+H).

Compound 92: ¹H NMR (300 MHz, CDCl₃): δ 8.43 (s, 1H), 8.06-8.03 (m, 1H), 7.46-7.39 (m, 5H), 7.32-7.22 (m, 7H), 6.97-6.94 (m, 2H), 6.86-6.81 (m, 2H), 4.69-4.66 (t, 1H, NH), 3.72-3.66 (q, 2H), 2.75-2.74 (t, 2H); LC-MS (ESI) m/z 562.3 (M+H).

Compound 93: ¹H NMR (300 MHz, CDCl₃): δ 8.42 (s, 1H), 7.50 (s, 1H), 7.44-7.39 (m, 5H), 7.30-7.24 (m, 3H), 7.22-7.16 (m, 6H), 6.89-6.87 (d, J=8.4 Hz, 2H), 7.22-7.16 (m, 6H), 6.89-6.87 (d, J=8.4 Hz, 2H), 4.69-4.68 (t, 1H, NH), 3.66-3.66 (q, 2H), 2.71-2.67 (t, 2H); LC-MS (ESI) m/z 560.2 (M+H).

Compound 94: ¹H NMR (300 MHz, CDCl₃): δ 8.40 (s, 1H), 7.85-7.84 (m, 1H), 7.43-7.33 (m, 6H), 7.26-7.17 (m, 6H), 7.04-7.01 (m, 1H), 6.85-6.79 (m, 4H), 4.66-4.62 (t, 1H, NH), 3.65-3.59 (q, 2H), 2.66-2.61 (t, 2H); LC-MS (ESI) m/z 562.3 (M+H).

Compound 95: ¹H NMR (300 MHz, CDCl₃): δ 8.41 (s, 1H), 7.43-7.38 (m, 6H), 7.30-7.27 (m, 2H), 7.24-7.19 (m, 5H), 7.09 (s, 1H), 6.89-6.86 (d, J=7.8 Hz, 2H), 6.73 (s, 2H), 4.68-4.67 (t, 1H, NH), 3.80 (s, 3H), 3.79 (s, 3H), 3.65-3.61 (q, 2H), 2.70-2.66 (t, 2H); LC-MS (ESI) m/z 586.2 (M+H).

Compound 96: ¹H-NMR (300 MHz, CDCl₃): δ 8.43 (s,H), 8.11-8.25(t H), 7.11-7.26 (m, 17H), 4.67-4.70 (t, H), 3.61-3.67 (q, 2H), 2.64-2.69 (t, 2H); LC-MS (ESI) m/z 544.7 (M+H).

Compound 97: ¹H-NMR (300 MHz, CDCl₃):δ 10.01 (s, H), 8.70-8.71 (d, H), 8.67 (s, H), 8.44-8.58 (d, H), 7.17-7.46 (m, 14H), 4.66-4.70 (t, NH), 3.67-3.73 (q, 2H), 2.74-2.78 (t, 2H).

Compound 98: ¹H-NMR (300 MHz, CDCl₃): δ 8.41 (s, H), 7.17-7.27 (m,14 H), 7.01-7.04 (d, 2H), 6.82-6.84 (d, 2H), 4.64-4.68 (t, NH), 3.59-3.65 (q, 2H), 2.64-2.68 (t, 2H), 2.23 (s, 3H).

Compound 100: ¹H-NMR (300 MHz, CDCl₃): δ 8.41 (s, H), 7.47-7.48 (m, 4 H), 7.45-7.47 (m, 10H), 7.43-7.44 (d, 2H), 7.42-7.43 (d, 2H), 3.65-3.68 (q, 2H), 2.93 (s, 6H), 1.25-2.17 (t, 2H).

Compound 107: ¹H NMR (400 MHz, d₆-DMSO): δ 8.61 (s, 1H), 8.59 (s, 1H), 8.36 (s, 1H), 8.32 (t, J=6.8 Hz, 1H), 7.80-7.78 (m, 2H), 7.55-7.49 (m, 3H), 7.44-7.37 (m, 4H), 7.26 (d, J=8.4 Hz, 2H), 7.19 (d, J=8.4 Hz, 2H), 6.94 (t, J=7.6 Hz, 1H), 4.22 (q, J=7.2 Hz, 2H), 3.77 (td, J=6.8, 6.8 Hz, 2H), 2.87 (t, J=6.8 Hz, 2H), 2.87 (t, J=6.8 Hz, 2H), 1.09 (t, J=7.2 Hz, 3H); LC-MS (ESI) m/z 522.7 (M+H).

Compound 115: ¹H NMR (300 MHz, CD₃OD): δ 8.29 (s, 1H), 7.66 (s, 2H), 7.38~7.47 (m, 6H), 7.21~7.32 (m, 7H), 7.04 (brs, 4H), 6.93 (s, 1H), 6.90 (s, 1H), 3.67 (t, 2H), 3.41 (s, 2H), 2.72 (t, 2H), 2.26 (s, 6H).

Compound 118: ¹H NMR (300 MHz, CDCl₃): δ 8.42 (s, 1H), 7.39~7.46 (m, 6H), 7.21~7.31 (m, 9H), 6.99 (d, 2H), 6.94 (s, 1H), 6.91 (s, 1H), 4.66 (t, 1H), 3.67 (dt, 2H), 3.45 (s, 3H), 2.72 (t, 2H), 2.44 (br s, 8H), 2.27 (s, 3H).

Compound 119: ¹H NMR (300 MHz, CDCl₃): δ 8.42 (s, 1H), 7.35~7.38 (m, 6H), 7.22~7.31 (m, 9H), 7.11 (dd, 2H), 7.01 (d, 1H), 6.95 (s, 1H), 6.92 (s, 1H), 4.65 (t, 1H), 3.68 (dt, 2H), 3.38 (s, 2H), 2.73 (t, 2H), 2.22 (s, 6H).

Compound 122: ¹H NMR (300 MHz, CDCl₃): δ 8.42 (s, 1H), 7.38~7.47 (m, 6H), 7.21~7.31 (m, 8H), 7.03 (dd, 2H), 6.98 (d, 2H), 6.95 (s, 1H), 6.92 (s, 1H), 4.66 (t, 1H), 3.66 (dt, 2H), 3.45 (s, 2H), 2.73 (t, 2H), 2.44 (br s, 8H), 2.25 (s, 3H).

Compound 123: ¹H NMR (300 MHz, CDCl₃): δ 8.41 (s, 1H), 8.00 (dd, 1H), 7.8~7.47 (m, 5H), 7.21~7.32 (m, 7H), 7.22 (dd, 2H), 6.92 (d, 2H), 6.90 (d, 2H), 6.53 (s, 1H), 4.64 (t, 1H), 3.68 (dt, 2H), 3.38 (s, 2H), 2.73 (t, 2H), 2.02 (s, 6H); LC-MS (ESI) m/z 583.7 (M+H).

Compound 124: ¹H NMR (300 MHz, CDCl₃): δ 8.42 (s, 1H), 8.03 (dd, 1H), 7.39~7.50 (m, 6H), 7.19~7.34 (m, 8H), 7.05 (dd, 1H), 6.94~6.97 (m, 2H), 6.90 (dd, 1H), 6.53 (s, 1H), 4.67 (t, 1H), 3.68 (dt, 2H), 3.50 (s, 2H), 2.73 (t, 2H), 2.33 (brs, 4H), 1.41 (brs, 6H).

Compound 126: ¹H NMR (300 MHz, CDCl₃): δ 8.42 (s, 1H), 8.01 (dd, 1H), 7.40~7.49 (m, 5H), 7.23~7.34 (m, 9H), 7.10 (dd, 1H), 6.95~7.00 (m, 3H), 6.41 (s, 1H), 4.67 (t, 1H), 3.70 (dt, 2H), 3.54 (s, 2H), 2.76 (t, 2H), 2.40 (brs, 8H), 2.22)s, 3H).

Compound 146: LC-MS (ESI) m/z 527.2 (M+H).
Compound 147: LC-MS (ESI) m/z 527.1 (M+H).
Compound 148: LC-MS (ESI) m/z 527.1 (M+H).
Compound 151: LC-MS (ESI) m/z 528.2 (M+H).
Compound 152: LC-MS (ESI) m/z 528.1 (M+H).
Compound 160: LC-MS (ESI) m/z 531.2 (M+H).
Compound 161: LC-MS (ESI) m/z 531.2 (M+H).
Compound 163: LC-MS (ESI) m/z 547.1 (M+H).
Compound 164: LC-MS (ESI) m/z 547.1 (M+H).

Compound 171: ¹H NMR (400 MHz, CDCl₃): δ 8.44 (s, 1H), 7.53 (d, J=7.6 Hz, 2H), 7.33~7.48 (m, 9H), 7.22~7.24 (m, 3H), 7.13 (t, J=7.6 Hz, 1H), 6.87 (s, 1H), 4.76 (bt, J=6.0 Hz, 1H), 3.70 (q, J=6.4 Hz, 2H), 2.95 (t, J=6.4 Hz, 2H); LC-MS (ESI) m/z 533.2 (M+H).

Compound 172: ¹H NMR(CDCl₃): δ 8.20 (s, 1H), 7.44-7.18 (m, 15H), 7.02 (d, J=8.4 Hz, 2H), 6.95 (d, J=8.4 Hz, 2H), 3.67 (t, J=6.9 Hz, 2H), 2.75 (t, J=6.9 Hz, 2H); LCMS-ESI (m/z): 525 [M+H⁺].

Compound 173: ¹H NMR (DMSO-d₆): δ 8.63 (s, 1H), 8.61 (s, 1H) 8.17 (s, 1H), 7.43-7.34 (m, 4H), 7.25 (t, 2H, J=7.2 Hz), 7.13 (d, 2H, J=8.4 Hz), 6.93 (t, 1H, J=7.5 Hz), 6.79 (t, 1H, J=5.4 Hz), 3.62 (q, 2H, J=8.4 Hz), 2.81 (t, 2H, J=8.1 Hz), 2.70-2.61 (m, 4H), 1.82-1.73 (m, 2H).

Compound 175: ¹H NMR (400 MHz, CDCl₃) δ 8.49 (s, 1H),7.62-7.60 (m, 2H), 7.53 (d, J=7.2 Hz, 2H), 7.41-7.20 (m, 14H), 7.11 (d, J=8.0 Hz, 2H), 7.03 (t, J=7.2 Hz, 2H), 5.59 (brs, 1H), 3.89 (td, J=6.8, 6.8 Hz, 2H), 2.94 (t, J=6.8 Hz, 2H); LC-MS (ESI) m/z 526.4 (M+H).

Compound 176: ¹H NMR (400 MHz, d₆-DMSO) δ 8.61 (s, 1H), 8.58 (s, 1H), 8.33 (s, 1H), 8.00 (d, J=7.2 Hz, 2H), 7.98 (brs, 1H), 7.54 (t, J=7.6 Hz, 2H), 7.48-7.42 (m, 4H), 7.38 (d, J=7.6 Hz, 2H), 7.26 (t, J=7.6 Hz, 2H), 6.94 (t, J=7.6 Hz, 1H), 3.72 (brs, 2H), 2.90 (t, J=7.2 Hz, 2H); LC-MS (ESI) m/z 450.2 (M+H).

Compound 196: ¹H-NMR (400 MHz, DMSO-d₆): δ 8.62 (d, J=11.6 Hz, 2H), 8.29 (s, 1H), 7.44 (d, J=6.8 Hz, 2H), 7.38 (d, J=6.8 Hz, 2H), 7.25 (t, J=6.8 Hz, 2H), 7.16 (d, J=7.2 Hz, 2H), 6.95 (t, J=7.2 Hz, 1H), 6.69 (t, J=7.2 Hz, 1H), 3.67 (dd, J=6.8 Hz, 14 Hz, 2H), 3.00 (t, J=6.8 Hz, 2H), 2.93 (t, J=6.8 Hz, 2H), 2.85 (t, J=7.2 Hz, 2H), 2.42 (m, 2H); MS (ESI) m/z 430.6 (M+H).

Compound 197: ¹H-NMR (300 MHz, CDCl₃): δ 8.44 (s, H), 8.15-8.18 (d, H), 7.47-7.60 (m, 7H), 7.26-7.37 (m, 10H), 4.65-4.69 (t, NH), 3.65-3.71 (q, 2H), 2.71-2.75 (t, 2H).

Compound 198: ¹H-NMR (300 MHz, CDCl₃): δ 8.41 (s, H), 7.38-7.47(m, 12H), 7.27-7.28 (m, 2H), 4.64-4.67 (t, H), 3.64-3.68 (q, 2H), 3.36-3.40 (t, 2H), 2.68-2.71 (t, 2H), 2.58-2.59 (t, 2H), 2.35 (s, 6H).

Compound 199: ¹H-NMR (300 MHz, CDCl₃): δ 8.38 (s, H), 7.33-7.46(m, 12H), 7.29-7.30 (m, 2H), 4.64-4.67 (t, H), 3.63-3.72 (m, 4H), 3.39-3.40 (m, 2H), 2.63-2.68 (m, 2H); LC-MS (ESI) m/z 492.7 (M+H).

Compound 200: ¹H-NMR (300 MHz, CDCl₃): δ 8.43 (s, H), 7.17-7.48 (m, 14H), 6.87-6.90 (d, 2H), 5.84-5.88 (t, H), 4.65-5.29(t, H), 4.14-4.21 (q, 2H), 4.05-4.07 (d, 2H), 3.62-3.69 (q, 2H), 2.67-2.71 (t, 2H), 1.22-1.24 (t, 3H).

Compound 201: ¹H-NMR (300 MHz, CDCl₃): δ 8.41 (s, H), 7.37-7.42 (m, 4H), 7.20-7.26 (m, 8H), 6.89-6.92 (d, 2H), 4.64-4.68 (t, NH), 3.64-3.68 (q, 2H), 2.62-2.63 (t, 2H), 2.57-2.61 (m, 2H), 0.65-0.72 (q, 2H), 0.59-0.63 (t, 2H).

Compound 202: ¹H NMR (400 MHz, d₆-DMSO) δ 8.62 (s, 1H), 8.60 (s, 1H), 8.35 (s, 1H), 8.14-8.11 (m, 2H), 7.56-7.36 (m, 7H), 7.28-7.20 (m, 4H), 6.97-6.92 (m, 1H), 6.61 (t, J=6.4 Hz, 1H), 5.58 (t, J=6.0 Hz, 1H), 4.44 (d, J=6.0 Hz, 2H), 3.79 (td, J=6.4, 6.4 Hz, 2H), 2.89 (t, J=6.4 Hz, 2H); LC-MS (ESI) m/z 504.7 (M+H).

Compound 203: ¹H NMR (400 MHz, CDCl₃) δ 8.44 (s, 1H), 7.50 (brs, 1H), 7.49 (brs, 1H), 7.36-7.29 (m, 6H), 7.25-7.21 (m, 4H), 7.19 (d, J=8.4 Hz, 2H), 7.04-7.00 (m, 1H), 6.93 (d, J=8.4 Hz, 2H), 5.00 (t, J=6.4 Hz, 1H), 3.72 (td, J=6.4, 6.4 Hz, 2H), 2.77 (t, J=6.4 Hz, 2H); LC-MS (ESI) m/z 450.6 (M+H).

Compound 204: ¹H NMR (CDCl₃): δ 8.27 (s, 1H), 8.15 (d, J=7.2 Hz, 1H), 7.74 (d, J=9.0 Hz, 2H), 7.44-7.27 (m, 6H), 7.18 (d, J=8.4 Hz, 2H), 7.03 (t, J=7.2 Hz, 2H), 6.97 (d, J=8.7 Hz, 2H), 6.83 (s, 1H), 3.86 (s, 3H), 3.81 (t, J=6.9 Hz, 2H), 3.37 (brs, 2H), 2.96 (t, J=6.9 Hz, 2H); LCMS-ESI (m/z): 480 [M+H⁺].

Compound 205: ¹H NMR (DMSO): δ 9.93 (s, 1H), 8.23 (s, 1H), 8.01 (brs, 1H), 7.61 (d, J=6.3 Hz, 2H), 7.43 (d, J=5.4 Hz, 2H), 7.37 (d, J=6.3 Hz, 2H), 7.26 (t, J=6.0 Hz, 2H), 7.18 (d, J=6.3 Hz, 2H), 7.10(s, 1H), 6.95 (t, J=5.4 Hz, 1H), 6.88 (d, J=6.6 Hz, 2H), 3.70 (t, J=5.4 Hz, 2H), 3.27 (brs, 2H), 2.86 (t, J=5.4 Hz, 2H); LCMS-ESI (m/z): 466 [M+H$^+$].

Compound 206: $^1$H NMR (CD$_3$OD): δ 8.20 (s, 1H), 8.01 (brs, 1H), 7.74 (d, J=8.7 Hz, 2H), 7.40 (d, J=8.4 Hz, 2H), 7.34 (d, J=8.7 Hz, 2H), 7.26 (t, J=7.8 Hz, 2H), 7.19 (d, J=8.4 Hz, 2H), 7.04 (d, J=9.0 Hz, 2H), 6.99 (s, 1H), 6.98-6.96 (m, 1H), 4.15 (t, J=5.4 Hz, 2H), 3.78 (t, J=7.2 Hz, 2H), 2.91 (t, J=7.2 Hz, 2H), 2.78 (t, J=5.4 Hz, 2H), 2.35 (s, 6H); LCMS-ESI (m/z): 537 [M+H$^+$].

Compound 207: LCMS-ESI (m/z): 537.1 [M+H$^+$].

Compound 208: $^1$H-NMR (400 MHz, DMSO-d$_6$): δ 8.61 (d, J=10.8 Hz, 2H), 8.32 (s, 1H), 7.44 (d, J=4.0 Hz, 2H), 7.38 (d, J=4.0 Hz, 2H), 7.26 (t, J=7.6 Hz, 2H), 7.16)d, J=4.0 Hz, 2H), 6.95 (t, J=7.2 Hz, 1H), 6.66 (s, 1H), 4.64 (s, 2H), 4.09 (q, J=7.2 Hz, 2H), 3.35 (m, 4H), 2.95 (s, 2H), 2.85 (t, J=7.2 Hz, 2H), 1.20 (t, J=7.2 Hz, 2H); MS (ESI) m/z 517.7 (M+H).

Compound 209: $^1$H NMR (400 MHz, CDCl$_3$): δ 9.89 (br s, 1H), 8.42 (s, 1H), 8.03 (d, 1H), 8.01 (s, 2H), 7.47 (dt, 1H), 7.41 (dt, 2H), 7.37 (dd, 2H), 7.24~7.34 (m, 3H), 7.04 (dd, 1H), 6.95 (dt, 1H), 6.47 (s, 1H), 5.90 (t, 1H), 3.89 (dt, 2H), 3.38 (s, 2H), 2.99 (t, 2H), 2.04 (s, 6H); LC-MS (ESI) m/z 541.3 (M+H).

Compound 210: LCMS-ESI (m/z): 542.1 [M+H$^+$].

Compound 211: $^1$H NMR (300 MHz, CD$_3$OD): δ 9.89 (br s, 1H), 8.42 (s, 1H), 7.78~7.82 (m, 1H), 7.78 (s, 2H), 7.43 (dt, 2H), 7.37 (t, 1H), 7.34 (d, 2H), 7.25 (d, 1H), 7.22 (d, 2H), 7.13 (d, 1H), 7.11 (dd, 2H), 6.97 (dt, 1H), 3.79 (t, 2H), 3.42 (s, 2H), 2.95 (t, 2H), 2.11 (s, 6H); LC-MS (ESI) m/z 507.3 (M+H).

Compound 212: LCMS-ESI (m/z): 507.1 [M+H$^+$].

Compound 213: $^1$H NMR (300 MHz, d$_6$-DMSO) δ 8.63 (s, 1H), 8.61 (s, 1H), 8.38 (s, 1H), 7.47-7.43 (m, 5H), 7.36-7.24 (m, 6H), 7.03-6.92 (m, 3H), 5.43 (t, J=6.0 Hz, 1H), 3.64 (td, J=6.0, 6.0 Hz, 2H), 2.74 (t,J=6.0 Hz, 2H); LC-MS (ESI) m/z 484.7 (M+H).

Compound 214: $^1$H-NMR (300 MHz, CDCl$_3$): δ 8.40 (s, H), 7.36-7.45 (m, 4H), 7.18-7.28 (m, 8H), 6.85-6.87 (d, 2H), 4.27-4.34 (m, H), 3.63-3.66 (q, 2H), 2.64-2.67 (t, 2H), 2.18-2.29 (m, 2H), 1.74-1.84 (m, 2H), 1.55-1.63 (m, 2H).

Compound 215: $^1$H-NMR (300 MHz, CDCl$_3$): δ 8.33 (s, H), 7.81-7.82 (d, 2H), 7.16-7.60 (m, 9H), 6.91 (s, H), 3.81-3.85 (t, 2H), 3.63-3.67 (m, 2H), 3.55-3.58 (m, 2H), 2.95-3.39 (t, 2H).

Compound 216: $^1$H-NMR (300 MHz, CDCl$_3$): δ 8.38 (s, H), 7.80-7.81(d, 2H), 7.13-7.44 (m, 9H), 6.86(s, H), 3.82-3.87(t, 2H), 3.66-3.69 (t, 4H), 3.34-3.39 (q, 2H), 2.92-2.97 (t, 2H), 2.48-2.56 (m, 4H); LC-MS (ESI) m/z 487.7 (M+H).

Compound 217: $^1$H-NMR (300 MHz, CDCl$_3$): δ 8.40 (s, H), 7.38-7.49 (m, 3H), 7.22-7.30 (m, 6H), 5.87-5.90(t, NH), 5.24-5.27 (t, NH), 3.85-3.90 (q, 2H), 3.58-3.68 (m, 4H), 2.96-2.99 (t, 2H).

Compound 218: $^1$H-NMR (300 MHz, CDCl$_3$): δ 8.40 (s, H), 7.37-7.47 (m, 3H), 7.21-7.32 (m, 6H), 5.87-5.90(t, NH), 5.24-5.27 (t, NH), 3.84-3.91(q, 2H), 3.66-3.69(t, 4H), 3.33-3.39 (q, 2H), 2.95-2.99 (t, 2H), 2.50-2.54 (t, 2H), 2.17-2.47 (t, 4H).

Compound 219: $^1$H NMR (400 MHz, CDCl$_3$) δ 8.46 (s, 1H), 8.22 (ddd, J=7.6, 2.0, 2.0 Hz, 1H), 8.12 (s, 1H), 7.60-7.54 (m, 2H), 7.40-7.21 (m, 12H), 7.17 (d, J=8.4 Hz, 2H), 7.07 (t, J=7.6 Hz, 1H), 6.83 (d, J=8.4 Hz, 2H), 4.32 (t, J=5.6 Hz, 2H), 3.76 (td, J=5.6, 5.6 Hz, 2H), 2.71 (t, J=5.6 Hz, 2H); LC-MS (ESI) m/z 571.0 (M+H).

Compound 220: LC-MS (ESI) m/z 402.0 (M+H).

Compound 221: $^1$H NMR (CDCl$_3$): δ 8.30 (s, 1H), 7.44-7.30 (m, 9H), 7.19 (d, J=6.3 Hz, 2H), 7.09-7.01 (m, 2H), 7.00 (s, 1H), 6.93-6.89 (m, 1H), 3.88 (s, 3H), 3.82 (t, J=6.9 Hz, 2H), 3.37 (brs, 2H), 2.96 (t, J=6.9 Hz, 2H); LCMS-ESI (m/z): 480 [M+H$^+$].

Compound 222: $^1$H-NMR (300 MHz, CDCl$_3$): δ 8.42 (s, H), 7.39-7.49 (m, 12H), 6.95-7.17 (d, 2H), 4.71-4.74 (t, H), 4.64-4.67 (t, H), 3.66-3.71 (q, 2H), 3.24-3.29 (q, 2H), 2.72-2.75 (t, 2H), 1.47-1.54 (m, 2H), 1.30-1.40 (m, 2H), 0.90-0.93 (t, 3H).

Compound 223: $^1$H NMR (CDCl$_3$): δ 8.31 (s, 1H), 7.43-7.26 (m, 9H), 7.18 (d, J=8.4 Hz, 2H), 7.06-7.04 (m, 2H), 6.88 (s, 1H), 6.85-6.83 (m, 1H), 3.83 (t, J=6.3 Hz, 2H), 3.38 (brs, 2H), 2.96 (t, J=6.3 Hz, 2H); LCMS-ESI (m/z): 466 [M+H$^+$].

Compound 224: $^1$H NMR (CDCl$_3$): δ 8.31 (s, 1H), 8.01(d, J=5.7 Hz, 2H), 7.39-7.18 (m, 9H), 7.00-6.93 (m, 2H), 6.95 (s, 1H), 6.86-6.85 (m, 1H), 4.04 (t, J=5.7 Hz, 2H), 3.66 (t, J=6.3 Hz, 2H), 2.80 (t, J=6.3 Hz, 2H), 2.72 (t, J=5.7 Hz, 2H), 2.34 (s, 6H); LCMS-ESI (m/z): 537 [M+H$^+$].

Compound 225: $^1$H NMR (300 MHz, d$_6$-DMSO) δ 8.69 (s, 1H), 8.66 (s, 1H), 8.31 (s, 1H), 7.93 (t, J=6.6 Hz, 1H), 7.64-7.38 (m, 9H), 7.28-7.18 (m, 4H), 6.94 (d, J=7.2 Hz, 1H), 6.29 (t, J=5.1 Hz, 1H), 4.77 (d, J=5.1 Hz, 2H), 3.73 (td, J=6.6, 6.6 Hz, 2H), 2.85 (t, J=6.6 Hz, 2H); LC-MS (ESI) m/z 480.2 (M+H).

Compound 226: $^1$H NMR (400 MHz, d$_6$-DMSO) δ 8.64 (s, 1H), 8.61 (s, 1H), 7.51 (t, J=7.6 Hz, 2H), 7.44-7.38 (m, 5H), 7.26 (t, J=7.6 Hz, 2H), 7.17 (d, J=8.4 Hz, 2H), 7.11 (t, J=6.4 Hz, 1H), 6.94 (t, J=7.6 Hz, 1H), 3.70 (td, J=6.4, 6.4 Hz, 2H), 2.87 (t, J=6.4 Hz, 2H), 2.52 (s, 3H); LC-MS (ESI) m/z 464.2 (M+H).

Compound 227: $^1$H NMR (DMSO-d$_6$): δ 8.71 (s, 1H), 8.01-7.91 (m, 4H), 7.33-7.24 (m, 6H), 7.15-6.99 (m, 4H), 6.45 (t, 1H), 3.67 (t,2H, J=6.9 Hz), 3.16 (q, 2H, J=6.0 Hz), 3.08-2.94 (m, 2H), 2.83 (t, 2H, J=6.0 Hz), 1.84 (t, 1H, J=6.6 Hz).

Compound 228: $^1$H NMR (400 MHz, d$_6$-DMSO): δ 8.36 (s, 1H), 7.92~7.98 (m, 5H), 7.70 (dd, 2H), 7.47~7.57 (m, 6H), 7.23~7.28 (m, 3H), 3.76 (dt, 2H), 2.92 (t, 2H), LC-MS (ESI) m/z 469.7 (M+H).

Compound 229: $^1$H NMR (400 MHz, d$_6$-DMSO): δ 10.19 (s, 1H), 8.28 (s, 1H), 8.12 (brs, 1H), 7.93 (d, 2H), 7.78 (d, 2H), 7.69 (d, 2H), 7.37~7.57 (m, 7H), 7.25 (d, 2H), 3.72 (dt, 2H), 2.91 (t, 2H).

Compound 230: LC-MS (ESI) m/z 579.0 (M+H).

Compound 231: LC-MS (ESI) m/z 451.2 (M+H).

Compound 232: $^1$H-NMR (300 MHz, CDCl$_3$): δ 8.37 (s, H), 8.16-8.17(d, 2H), 8.00-8.02 (d, 2H), 7.20-7.50 (m, 9H), 3.85-3.90 (q, 2H), 2.96-2.99 (t, 2H).

Compound 233: $^1$H-NMR (300 MHz, CDCl$_3$): δ 8.35 (s, H), 7.28-7.45 (m, 9H), 6.88 (s, H), 3.82-3.85(t, 2H), 3.35-3.38 (t, 2H), 2.93-2.96 (t, 2H), 2.57-2.60 (t, 2H), 2.30 (s, 6H).

Compound 234: LC-MS (ESI) m/z 479.2 (M+H).

Compound 235: $^1$H NMR (CDCl$_3$): δ 8.31 (s, 1H), 7.80 (d, J=6.3 Hz, 1H), 7.74 (d, J=9.3 Hz, 2H), 7.43-7.27 (m, 6H), 7.16 (d, J=8.7 Hz, 2H), 7.08-7.01(m, 1H), 6.98 (d, J=8.7 Hz, 2H), 6.78 (s, 1H), 4.28 (t, J=6.0 Hz, 2H), 3.86-3.80 (m, 4H), 2.95 (t, J=6.6 Hz, 2H); LCMS-ESI (m/z): 529 [M+H$^+$].

Compound 236: $^1$H NMR (CDCl$_3$): δ 8.26 (s, 1H), 7.73 (d, J=8.7 Hz, 2H), 7.45-7.41 (m, 2H), 7.36 (d, J=8.7 Hz, 2H), 7.32-7.26 (m, 3H), 7.17 (d, J=8.4 Hz, 2H), 7.04-7.01 (m, 1H), 6.97 (d, J=9.0 Hz, 2H), 6.88 (s, 1H), 4.41-4.20 (m, 4H), 3.80 (t, J=6.9 Hz, 2H), 3.45-3.36 (m, 3H), 3.05 (d, J=11.4 Hz, 2H), 2.95 (t, J=6.9 Hz, 2H), 2.84 (d, J=5.7 Hz. 2H), 2.17 (t, J=12.0 Hz, 2H), 1.78 (d, J=11.4 Hz, 2H); LCMS-ESI (m/z): 607 [M+H$^+$].

Compound 237: $^1$H NMR (CDCl$_3$): δ 8.26 (s, 1H), 7.73 (d, J=9.0 Hz, 2H), 7.45-7.26 (m, 7H), 7.19 (d, J=8.4 Hz, 2H), 7.05-7.02 (m, 1H), 6.96 (d, J=9.0 Hz, 2H), 6.89 (s, 1H), 4.08

(t, J=6.0 Hz, 2H), 3.83-3.78 (m, 4H), 3.46-3.35 (m, 3H), 3.18 (d, J=12.0 Hz, 2H), 2.96 (t, J=6.9 Hz, 2H), 2.75 (t, J=7.8 Hz. 2H), 2.27-2.20 (m, 2H), 2.11 (t, J=12.0 Hz, 2H), 1.78 (d, J=13.5 Hz, 2H); LCMS-ESI (m/z): 621 [M+H$^+$].

Compound 238: LC-MS (ESI) m/z 530.0 (M+H).

Compound 239: $^1$H NMR (CDCl$_3$): δ 8.29 (s, 1H), 7.70 (d, J=9.3 Hz, 2H), 7.44-7.26 (m, 7H), 7.13 (d, J=8.4 Hz, 2H), 7.05-7.00 (m, 1H), 6.94 (d, J=8.7 Hz, 2H), 6.77 (s, 1H), 4.14 (t, J=5.7 Hz, 2H), 3.81-3.78 (m, 4H), 3.41-3.39 (m, 1H), 3.23-3.17 (m, 2H), 2.95-2.92 (m, 2H), 2.85 (t, J=5.7 Hz, 2H), 1.99-1.90 (m, 2H), 1.44-1.37 (m, 2H); LCMS-ESI (m/z): 593 [M+H$^+$].

Compound 240: $^1$H NMR (CDCl$_3$): δ 8.28 (s, 1H), 7.70 (d, J=7.2 Hz, 2H), 7.44-7.25 (m, 7H), 7.15 (d, J=8.4 Hz, 2H), 7.05-7.02 (m, 1H), 6.93 (d, J=9.0 Hz, 2H), 6.79 (s, 1H), 4.03 (t, J=6.0 Hz, 2H), 3.78 (d, J=6.9 Hz, 2H), 3.68-3.62 (m, 2H), 3.42-3.37 (m, 1H), 2.92 (t, J=6.6 Hz, 2H), 2.86-2.82 (m, 2H), 2.54 (t, J=7.5 Hz. 2H), 2.19-2.13 (m, 2H), 2.05-1.90 (m, 4H); LCMS-ESI (m/z): 607 [M+H$^+$].

Compound 241: $^1$H NMR (CDCl$_3$): δ 8.28 (s, 1H), 7.70 (d, J=7.2 Hz, 2H), 7.45-7.26 (m, 7H), 7.14 (d, J=8.4 Hz, 2H), 7.04-7.00 (m, 1H), 6.94 (d, J=9.0 Hz, 2H), 6.80 (s, 1H), 4.06 (t, J=6.0 Hz, 2H), 3.79 (d, J=6.6 Hz, 2H), 3.64 (dd, J=11.1, 4.2 Hz, 1H), 3.48 (dd, J=11.1, 3.6 Hz, 1H), 3.40-3.37 (m, 1H), 2.93 (t, J=6.6 Hz, 2H), 2.70-2.33 (m, 4H), 2.10-1.74 (m, 6H); LCMS-ESI (m/z): 607 [M+H$^+$].

Compound 242: $^1$H NMR (CDCl$_3$): δ 8.28 (s, 1H), 7.70 (d, J=7.2 Hz, 2H), 7.44-7.26 (m, 7H), 7.14 (d, J=8.4 Hz, 2H), 7.06-7.03 (m, 1H), 6.94 (d, J=9.0 Hz, 2H), 6.79 (s, 1H), 4.06 (t, J=6.0 Hz, 2H), 3.79 (d, J=6.3 Hz, 2H), 3.47-3.40 (m, 4H), 2.93 (t, J=6.6 Hz, 2H), 2.56 (d, J=7.2 Hz, 2H), 2.46-2.43 (m, 4H), 2.02-1.98 (m, 2H), 1.46 (s, 9H); LCMS-ESI (m/z): 692 [M+H$^+$].

Compound 243: $^1$H NMR (400 MHz, d$_6$-DMSO) δ 8.61 (s, 1H), 8.58 (s, 1H), 8.40 (s, 1H), 8.26 (brs, 1H), 8.17 (d, J=7.6 Hz, 2H), 7.63-7.53 (m, 3H), 7.44-7.42 (m, 2H), 7.37 (t, J=8.4 Hz, 2H), 7.28-7.24 (m, 2H), 7.18 (d, J=8.4 Hz, 2H), 6.96-6.92 (m, 1H), 3.71 (brs,2H), 2.89 (t, J=7.2 Hz, 2H); LC-MS (ESI) m/z 530.1 (M+2+H), 528.1 (M+H).

Compound 244: $^1$H NMR (CDCl$_3$): δ 8.34 (s, 1H), 7.95 (d, J=8.7 Hz, 2H), 7.43-7.39 (m, 4H), 7.28 (d, J=8.4 Hz, 2H), 7.11 (d, J=8.4 Hz, 2H), 7.07-7.03 (m, 1H), 7.00 (d, J=8.7 Hz, 2H), 3.85 (t, J=6.6 Hz, 2H), 3.39 (brs, 2H), 2.96 (t, J=6.6 Hz, 2H); LCMS-ESI (m/z): 514 [M+H$^+$].

Compound 245: $^1$H NMR (CDCl$_3$): δ 8.56 (s, 1H), 8.25 (s, 1H), 8.00 (brs), 7.73 (d, J=9.0 Hz, 2H), 7.37 (d, J=8.4 Hz, 2H), 7.18 (d, J=8.4 Hz, 3H), 7.07 (d, J=9.0 Hz, 2H), 3.81 (s, 3H), 3.69 (t, J=6.9 Hz, 2H), 2.87 (t, J=6.9 Hz, 2H); LCMS-ESI (m/z): 537 [M+H$^+$].

Compound 246: $^1$H NMR (CDCl$_3$): δ 8.56 (s, 1H), 8.25 (s, 1H), 8.00 (brs), 7.73 (d, J=9.0 Hz, 2H), 7.37 (d, J=8.4 Hz, 2H), 7.18 (d, J=8.4 Hz, 3H), 7.07 (d, J=9.0 Hz, 2H), 3.81 (s, 3H), 3.69 (t, J=6.9 Hz, 2H), 2.87 (t, J=6.9 Hz, 2H); LCMS-ESI (m/z): 481 [M+H$^+$].

Compound 247: LC-MS (ESI) m/z 551.0 (M+H).
Compound 248: LC-MS (ESI) m/z 458.2 (M+H).
Compound 249: $^1$H NMR (400 MHz, d$_6$-DMSO) δ 8.62 (s, 1H), 8.59 (s, 1H), 8.33 (s, 1H), 8.13-8.10 (m, 2H), 7.54-7.50 (m, 2H), 7.45-7.38 (m, 5H), 7.28-7.18 (m, 4H), 7.07 (t, J=6.0 Hz, 1H), 6.97-6.92 (m, 1H), 5.36 (t, J=6.0 Hz, 1H), 3.75 (td, J=6.0, 6.0 Hz, 2H), 2.86 (t, J=6.0 Hz, 2H), 2.73 (t, J=6.0 Hz, 2H); LC-MS (ESI) m/z 518.4 (M+H).

Compound 250: $^1$H NMR (400 MHz, CDCl$_3$) δ 8.37 (s, 1H), 7.70-7.68 (m, 2H), 7.43-7.35 (m, 14H), 7.10 (d, J=8.4 Hz, 2H), 7.04 (t, J=7.6 Hz, 1H), 6.34 (d, J=4.0 Hz, 1H), 6.33 (d, J=4.0 Hz, 1H), 4.40 (s, 2H), 3.84 (t, J=6.4 Hz, 2H), 2.90 (t, J=6.4 Hz, 2H); LC-MS (ESI) m/z 546.2 (M+H).

Compound 251: $^1$H NMR (400 MHz, d$_6$-DMSO) δ 8.69 (s, 1H), 8.66 (s, 1H), 8.30 (s, 1H), 7.68 (d, J=8.0 Hz, 2H), 7.51 (t, J=8.0 Hz, 2H), 7.44 (d, J=8.0 Hz, 2H), 7.48-7.37 (m, 3H), 7.26 (t, J=8.0 Hz, 2H), 7.17 (d, J=8.0 Hz, 2H), 6.96-6.92 (m, 2H), 4.61 (t, J=6.0 Hz, 1H), 3.74 (td, J=6.4, 6.4 Hz, 2H), 3.43 (td, J=6.0, 6.0 Hz, 2H), 2.92 (t, J=6.4 Hz, 2H), 2.88 (t, J=6.0 Hz, 2H), 1.65-1.48 (m, 4H); LC-MS (ESI) m/z 522.3 (M+H).

Compound 252: $^1$H NMR (400 MHz, CD$_3$OD): δ 8.26 (s, 1H), 8.03 (d, 1H), 7.96 (s, 2H), 7.32~7.48 (m, 8H), 7.19~7.26 (m, 2H), 6.95 (d, 2H), 3.81 (t, 1H), 3.44 (s, 2H), 2.24 (s, 6H); LC-MS (ESI) m/z 541.3 (M+H).

Compound 253: $^1$H NMR (400 MHz, CDCl$_3$): δ 8.37 (s, 1H), 8.01 (dt, 2H), 7.40~7.50 (m, 7H), 7.29 (s, 2H), 7.27 (s, 1H), 7.23 (d, 2H), 7.19 (s, 1H), 5.97 (dt, 1H), 3.85 (td, 2H), 3.57 (s, 2H), 2.96 (t, 2H), 2.36 (s, 6H); LC-MS (ESI) m/z 541.3 (M+H).

Compound 254: LC-MS (ESI) m/z 409.0 (M+H).
Compound 255: LC-MS (ESI) m/z 457.0 (M+H).
Compound 256: LC-MS (ESI) m/z 491.2 (M+H).
Compound 257: LC-MS (ESI) m/z 540.0 (M+H).

EXAMPLE 184

Co-crystallization of a Fused Bicyclic Pyrimidine Compound and Aurora Kinase

Expression and Purification of Aurora A: Aurora A catalytic domain (residues 123-401) with one mutation at residue 288 (T288D) and six His as the tag at the N-terminus was cloned into the pET-28a vector and expressed in BL21 DE3 *E. coli*. The protein was then purified by nickel column following the procedures as suggested by the suppliers (Amersham Biosciences, Piscataway, N.J.). The bound protein was washed with 10% of buffer solution (40 mmol HEPES (pH 7.5), 50 mmol NaCl and 500 mmol imidazole) and eluted with 100% of buffer solution. The fractions containing Aurora A catalytic domain was then treated with TEV protease (Invitrogen) overnight at 4° C. to remove the His tag and concentrated to 8 mg/mL in a buffer containing 40 mmol HEPES pH 7.5, 50 mmol NaCl, 1 mmol DTT.

Crystallization and Structure Determination: The hanging drop method was used to obtain the crystals of Aurora A in complex with test compounds. A drop of 1.5 l protein pre-incubated with a test compound for half hour on ice was mixed with the equal volume of reservoir solution (22% PEG400 and 0.1 mmol ammonia sulfate). The crystals were grown at 18° C. for 3-7 days. Before being flash-frozen in liquid nitrogen, the crystal was immersed briefly in a cryo-protectant containing 37% PEG400. Diffraction data were collected on beamline SP12B2 at the SPring-8 (Japan) and beamlines, BL13B1 and BL13C1, at the NSRRC (Taiwan). The data were processed by DENZO (see Otwinowski, Z.; Minor, W. Processing of x-ray diffraction data collected in oscillation mode. *Methods in Enzymology* 1997, 276, 307-326) and reduced with SCALEPACK. The structure was solved by molecular replacement in MOLREP (see Vagin A, T. A. MOLREP: an automated program for molecular replacement. *J. Appl. Cryst.* 1997, 30, 1022-1025) using the published Aurora A structure (PDB code: 1MQ4) as the search model. The refinement calculation were performed by REFMAC5 (see Murshudov G N, V. A., Dodson E J. Refinement of macromolecular structures by the maximum-likelihood method. *Acta Crystallogr* 1997, D, 240-255) and model building was carried out with the program O9.0 (see Jones T A, Z. J., Cowan S W, Kjeldgaard. Improved methods for building protein models in electron density maps and the location of errors in these models. *Acta Crystallogr* 1991, A, 110-119).

Compounds 6, 202, and 206 were each co-crystallized with Aurora A. Each of the compound-Aurora A complex structures was solved by x-ray crystallography.

EXAMPLE 185

Inhibiting Aurora A Activity

Aurora kinase A protein purification: The GST-tAurora A (123-401aa) fusion protein was produced by baculovirus expression system. The Aurora A catalytic domain with an N-terminal GST tag was constructed in pBacPAK8 plasmid and expressed in sf9 cells. Recombinant baculovirus infected sf9 cells were harvested by centrifugation, and the pellets were resuspended in PBS buffer (PBS, pH 7.3, 0.2 mM PMSF, 0.5 mM $Na_3VO_4$, 0.5 mM EDTA, 2 mM DTT, Complete Protease Inhibitor Cocktail table (1125700, Roche). Cells were lysed by sonication, and lysates were cleared by centrifugation at 15,000 rpm for 30 min. The supernatants were loaded into 1 ml of GST Sepharose 4 Fast Flow (17-5132-01, GE healthcare) column previously washed with PBS buffer. The column were washed with 30 volumes of PBS buffer, and then eluted by elution buffer (50 mM Tris (pH 8.0), 10 mM glutathione). To concentrate GST-tAurora A, buffer was replaced with Tris buffer (100 mM Tris (pH 7.5), 300 mM NaCl, 1 mM EDTA, 4 mM DTT) using Amicon ultra-15 (MWCO:30K, Millipore) to 2.4 mg/ml. After the addition of equal volume of glycerol and 0.04% Triton X-100, the proteins were stored aliquoted at −80° C.

Aurora Kinase A luminescent kinase assay: The inhibitory activity of the compounds of this invention against Aurora kinase was assessed using GST-tAurora A (123-401aa) fusion protein obtained above, according to a modified method described in Koresawa, M.; Okabe, T. *Assay Drug Dev Technol* 2004, 2, 153. Briefly, a test compound, enzyme, substrate-tetra(LRRWSLG), DTT and ATP were dissolved in Aur buffer (50 mM Tris-HCl pH 7.4, 10 mM NaCl, 10 mM $MgCl_2$, and 100 µg/ml BSA) individually before the assay. Test compounds were consecutively diluted from 10 mM stock (for single dose: compounds were diluted from 10 mM stock to 100 µM and 20 µM; for $IC_{50}$: 5× serial dilution was made from 100 µM to 0.16 µM) in Aur buffer. Diluted compounds (25 µl) were pre-incubated with purified 105 ng (10 µl) of GST-tAurora A (123-401aa) fusion protein at 25° C. for 15 min into 96 well U-bottomed plates (268152, NUNC). 5 µM ATP (5 µl), 1 mM DTT (5 µl) and 0.1 mM tetra(LRRWSLG) peptide substrate (5 µl) were added into the reactions of test compounds and GST-tAurora A. The reactions were incubated at 37° C. for 90 min. 50 µl of Kinase-Glo Plus Reagent (V3771, Promega) was added into the reactions, followed by the incubation at 25° C. for 20 min. 70 µl of reaction solutions were transferred to 96 well black plates (237108, NUNC) to quantify the ATP remaining in the solutions, which inversely relates to kinase activity. The luminescence was recorded by vector$^2$ (V-1420 multilabel HTS counter, Perkin Elmer).

Compounds 1-98, 100, 107, 115, 118, 119, 122-124, 126, 146-148, 151, 152, 160, 161, 163, 164, 171-173, 175, 176, and 196-257 were tested in this assay. Unexpectedly, Compounds 1, 3-10, 13-24, 26-32, 34, 40-42, 45, 52, 56-82, 91-98, 100, 107, 115, 118, 119, 122-124, 126, 146-148, 151, 160, 161, 163, 164, 171-173, 176, 196-242, 244, 245, and 247-256 showed $IC_{50}$ values (i.e., the concentration of a test compound at which activity of 50% of Aurora A is inhibited) lower than 1 µM. Among them, Compounds 5, 8-10, 13-15, 17-21, 23, 27-32, 41, 42, 45, 52, 56, 57, 59, 61-63, 66, 67, 70, 71, 73, 76-80, 82, 91, 96-98, 119, 123, 146, 147, 161, 163, 171, 172, 196, 198, 199, 201-212, 214, 217-226, 230, 232, 235-237, 239-242, 244, 247, 249, 250, 253, 254, and 256 showed $IC_{50}$ values between 45 nM and 400 nM; and Compounds 6, 16, 24, 58, 60, 251, 252, and 255 showed $IC_{50}$ values between 0.001 nM and 45 nM.

EXAMPLE 186

In vitro Anticancer Activity

HCT-116 cell viability was examined by the MTS assay (Promega, Madison, Wis., USA). 2000 HCT-116 cells in 100 µL McCoy's 5a medium were seeded in each well of a 96-well plate. After 96-h incubation with a test compound, the cells were incubated with 20 µL of a MTS/PMS mixture (MTS/PMS ratio: 20: 1) for 2 h at 37° C. in a humidified incubator with 5% $CO_2$ to allow viable cells to convert the tetrazolium salt (MTS) into formazan. The amount/concentration of formazan, which indicates the number of live cells, was determined by measuring the absorbance at 490 nm using a PerkinElmer Victor2 plate reader (PerkinElmer, Shelton, Cont., USA).

Compounds 6, 10, 13-16, 19-21, 23, 24, 27-33, 35, 36, 38-42, 57, 58, 60, 61, 79, 80, 82, 91-98, 100, 107, 115, 118, 119, 122-124, 126, 146-148, 151, 152, 160, 161, 163, 164, 171-173, 175, 176, and 196-257 were tested in this assay. Unexpectedly, Compounds 6, 14, 23, 24, 42, 57, 58, 60, 61, 79, 80, 82, 92, 93, 96, 115, 123, 147, 148, 171, 172, 176, 196, 202, 204, 207, 211-215, 217-226, 230, 232, 235-237, 239-241, 244, 245, and 247-256 showed $IC_{50}$ values (i.e., the concentration of a test compound which causes 50% of the cell death) between 100 nM and 900 nM; and Compounds 205, 206, 209, and 210 showed $IC_{50}$ values lower than 100 nM.

EXAMPLE 187

In vivo Anticancer Activity

In vivo efficacy of the compounds of this invention was assessed using colon tumor xenograft mice (injected with HCT-116), as described in Cancer Research 2004, 64, 4621-4628.

HCT-116 cells were grown as subcutaneous tumors in nude mice. When well-established HCT-116 xenografts were palpable with tumor size of ~100 $mm^3$, mice were randomly assigned to three groups: a vehicle control group (10 mice), a positive control group (10 mice), and a treatment group (21 mice). Of the treated mice, ten received Compound 209 at a daily dosage of 5 mg/kg and eleven received the same compound at a daily dosage of 15 mg/kg of via IV injection through the tail veins for 5 days/week for 2 consecutive weeks (days 1-5 and 8-12). The positive control mice received VX-680 (a known anti-cancer compound) at a daily dosage of 50 mg/kg, also via IV injection through the tail veins for 5 days/week for 2 consecutive weeks (days 1-5 and 8-12).

At the dosage of 5 mg/kg, Compound 209 suppressed tumor growth insignificantly while at a higher dosage, 15 mg/kg, Compound 209, unexpectedly showed inhibition of tumor growth comparable to that of VX-680 at a dosage of 50 mg/kg, indicating potent in vivo anti-cancer activity. More specifically, the treated mice on average had a tumor size of 381 $mm^3$ on the fourth day and 654 $mm^3$ on the eleventh day, while the vehicle control mice on average had a tumor size 567 mm³ on the fourth day and 1254 mm³ on the eleventh day.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

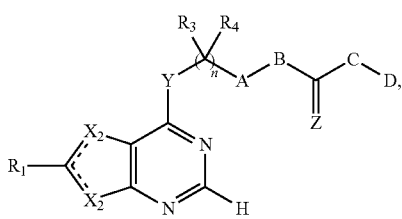

wherein
one of the two ═bonds is a single bond and the other is a double bond;
$X_1$ is $NR_a$ and $X_2$ is $CR_2$, in which $R_a$ is H, alkyl, alkenyl, alkynyl, aryl, or heteroaryl;
each of Y and Z, independently, is O, S, or $NR_b$, in which $R_b$ is H, alkyl, alkenyl, alkynyl, aryl, heteroaryl, cycloalkyl, cycloalkenyl, heterocycloalkyl, heterocycloalkenyl, cyano, or $NO_2$;
each of $R_1$ and $R_2$, independently, is H, alkyl, alkenyl, alkynyl, aryl, heteroaryl, halo, $C(O)OR_c$, or $C(O)NR_c R_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl;
each of $R_3$ and $R_4$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;
A is arylene or heteroarylene;
B is O, S, or $NR_e$, in which $R_e$ is H, alkyl, alkenyl, or alkynyl;
C is O, S, alkylene, or $NR_f$, in which $R_f$ is H, alkyl, alkenyl, or alkynyl; or B and C, together with the carbon atom to which they are bonded, are heterocycloalkyl or heterocycloalkenyl;
D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl or heteroaryl; and
n is 1, 2, 3, or 4.
2. The compound of claim 1, wherein $X_1$ is NH and $X_2$ is $CR_2$.

3. The compound of claim 2, wherein $R_1$ is H, alkyl, alkynyl, aryl, or heteroaryl.
4. The compound of claim 3, wherein Z is O and each of B and C is NH.
5. The compound of claim 4, wherein $R_1$ is phenyl optionally substituted with hydroxy or alkoxy.
6. The compound of claim 5, wherein $R_2$ is H, alkyl, alkynyl, halo, aryl, or heteroaryl.
7. The compound of claim 6, wherein Y is NH and n is 2.
8. The compound of claim 7, wherein A is phenyl; D is alkyl, aryl, heteroaryl, or cycloalkyl; and each of $R_3$ and $R_4$ is H.
9. The compound of claim 1, wherein $R_1$ is H, alkyl, alkynyl, aryl, or heteroaryl.
10. The compound of claim 9, wherein $R_1$ is phenyl optionally substituted with hydroxy or alkoxy.
11. The compound of claim 10, wherein $R_2$ is H, alkyl, alkynyl, halo, aryl, or heteroaryl.
12. The compound of claim 11, wherein $R_2$ is H, halo, or phenyl optionally substituted with hydroxy, alkoxy, or acylamino.
13. The compound of claim 1, wherein Z is O and each of B and C is NH.
14. The compound of claim 13, wherein $R_1$ is phenyl optionally substituted with hydroxy or alkoxy.
15. The compound of claim 14, wherein $R_2$ is H, halo, or phenyl optionally substituted with hydroxy, alkoxy, or acylamino.
16. A compound of formula (I):

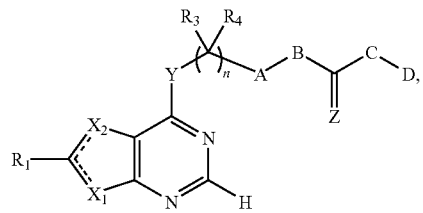

wherein
one of the two ═bonds is a single bond and the other is a double bond;
$X_1$ is S and $X_2$ is $CR_2$, or $X_1$ is $CR_2$ and $X_2$ is S;
each of Y and Z, independently, is O, S, or $NR_b$, in which $R_b$ is H, alkyl, alkenyl, alkynyl, aryl, heteroaryl, cycloalkyl, cycloalkenyl, heterocycloalkyl, heterocycloalkenyl, or cyano;
$R_1$ and $R_2$, together with the carbon atoms to which they are bonded, are cycloalkenyl, heterocycloalkenyl, aryl, or heteroaryl;
each of $R_3$ and $R_4$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;
A is arylene or heteroarylene;
B is O, S or $NR_e$, in which $R_e$ is H, alkyl, alkenyl, or alkynyl;
C is O, S, alkylene, or $NR_f$, in which $R_f$ is H, alkyl, alkenyl, or alkynyl; or B and C, together with the carbon atom to which they are bonded, are heterocycloalkyl or heterocycloalkenyl;

D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl, or heteroaryl; and n is 1, 2, 3, or 4.

17. The compound of claim 16, wherein $X_1$ is S and $X_2$ is $CR_2$.

18. The compound of claim 17, wherein Z is O and each of B and C is NH.

19. The compound of claim 18, wherein Y is NH and n is 2.

20. The compound of claim 19, wherein A is phenyl; D is alkyl, aryl, heteroaryl, or cycloalkyl; and each of $R_3$ and $R_4$ is H.

21. The compound of claim 20, wherein $R_1$ and $R_2$, together with the carbon atoms to which they are bonded, are cyclohexenyl.

22. The compound of claim 16, wherein the compound is

[Compound 42]

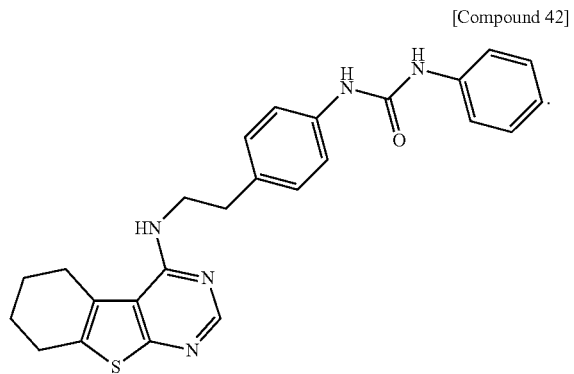

23. A pharmaceutical composition, comprising a compound of claim 1 and a pharmaceutically acceptable carrier.

24. A pharmaceutical composition, comprising a compound of claim 16 and a pharmaceutically acceptable carrier.

25. The compound of claim 1, wherein each of $R_1$ and $R_2$, independently, is H or aryl.

26. A compound of formula (I):

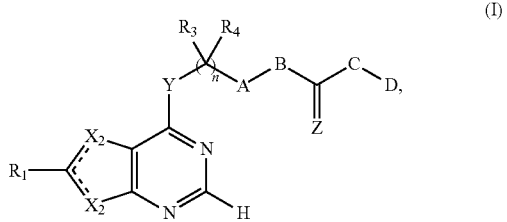

(I)

wherein one of the two ═bonds is a single bond and the other is a double bond;

$X_1$ is O or NH and $X_2$ is $CR_2$;

Y is O, S, or $NR_b$, in which $R_b$ is H, alkyl, alkenyl, alkynyl, aryl, heteroaryl, cycloalkyl, cycloalkenyl, heterocycloalkyl, heterocycloalkenyl, cyano, or $NO_2$;

Z is O;

$R_1$ is phenyl optionally substituted with hydroxyl or alkoxy, or heteroaryl;

$R_2$ is H, alkyl, alkenyl, alkynyl, aryl, heteroaryl, halo, C(O)$OR_c$, or C(O)$NR_cR_d$, in which each of $R_c$ and $R_d$, independently, is H, alkyl, alkenyl, alkynyl, aryl, heteroaryl, cycloalkyl, cycloalkenyl, heterocycloalkyl, or heterocycloalkenyl;

each of $R_3$ and $R_4$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;

A is arylene or heteroarylene;

each of B and C is NH;

D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl or heteroaryl; and n is 1, 2, 3, or 4.

27. The compound of claim 26, wherein $R_2$ is H, alkyl, alkynyl, halo, aryl, or heteroaryl.

28. The compound of claim 27, wherein Y is NH and n is 2.

29. The compound of claim 28, wherein A is phenyl; D is alkyl, aryl, heteroaryl, or cycloalkyl; and each of $R_3$ and $R_4$ is H.

30. The compound of claim 26, wherein $R_1$ is phenyl optionally substituted with hydroxy or alkoxy.

31. The compound of claim 30, wherein $R_2$ is H, halo, or phenyl optionally substituted with hydroxy, alkoxy, or acylamino.

32. A pharmaceutical composition, comprising a compound of claim 26 and a pharmaceutically acceptable carrier.

33. The compound of claim 26, wherein $R_1$ is aryl and $R_2$ is H or aryl.

34. The compound of claim 26, wherein the compound is one of compounds as shown below:

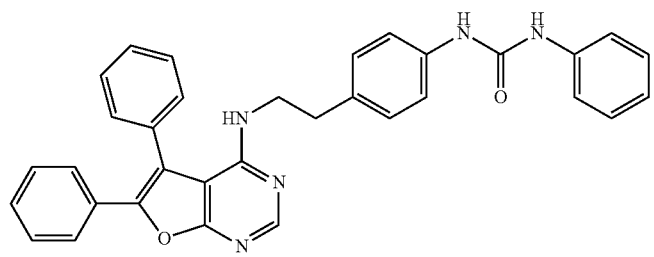

-continued
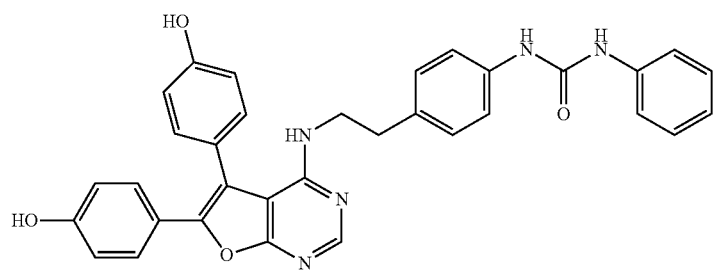
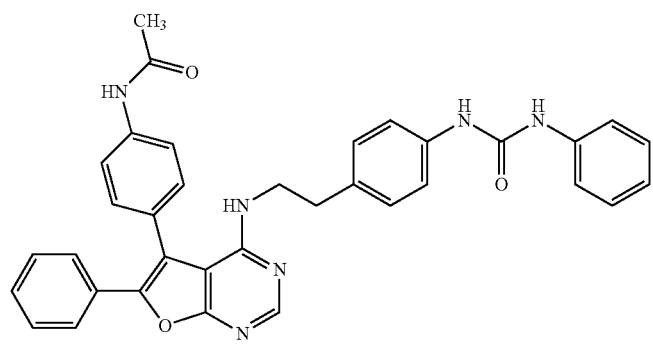
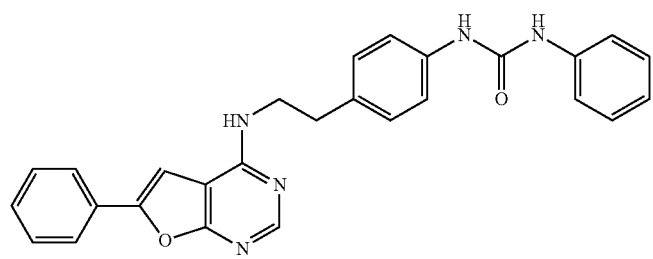
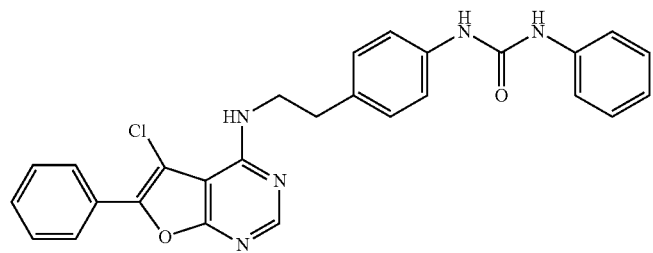
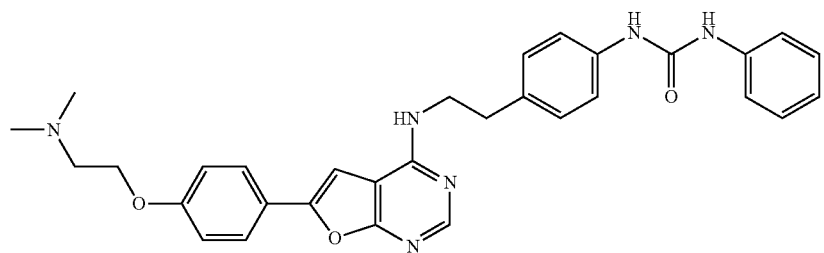
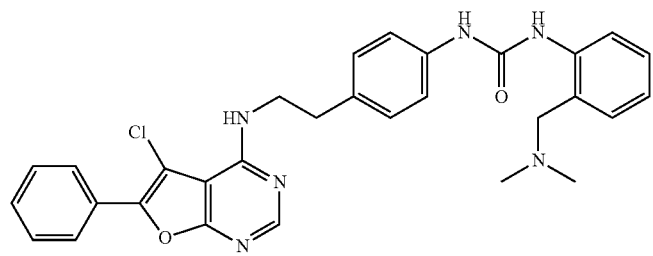

-continued
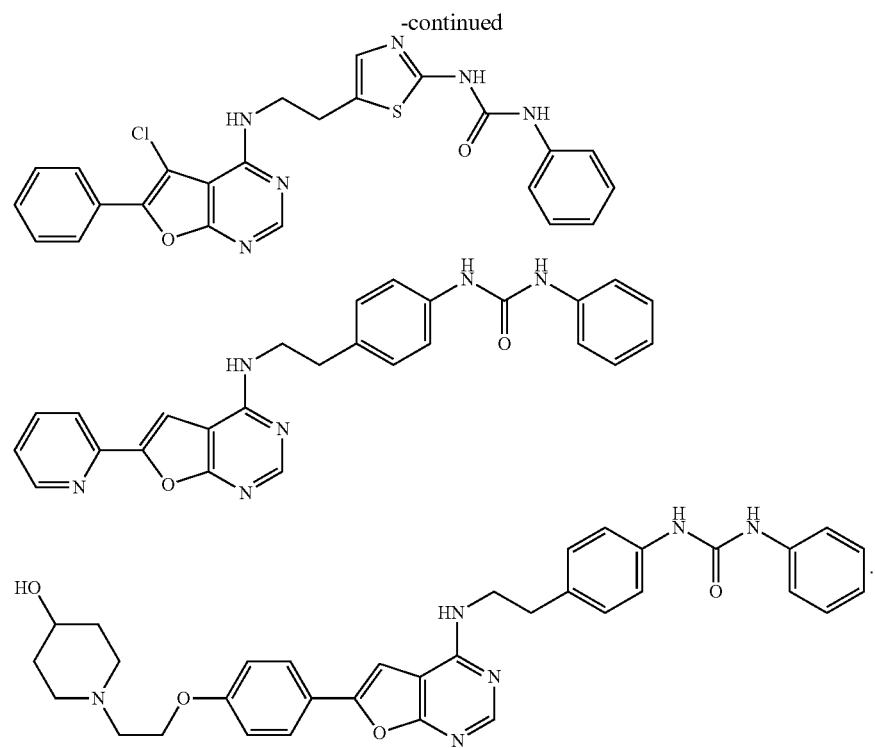
* * * * *

UNITED STATES PATENT AND TRADEMARK OFFICE
CERTIFICATE OF CORRECTION

PATENT NO. : 8,138,194 B2
APPLICATION NO. : 12/428044
DATED : March 20, 2012
INVENTOR(S) : Hsing-Pang Hsieh et al.

It is certified that error appears in the above-identified patent and that said Letters Patent is hereby corrected as shown below:

Please amend claim 1, in column 87, line 20, to read as follows:

A compound of formula (I):

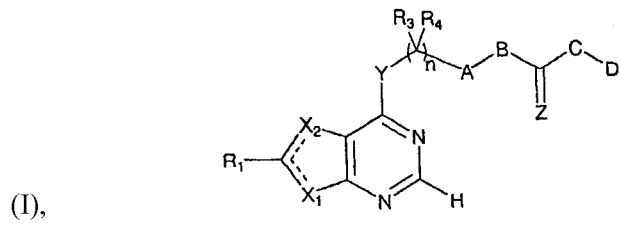

(I),
wherein
one of the two ---- bonds is a single bond and the other is a double bond;
X1 is NRa and X2 is CR2, in which Ra is H, alkyl, alkenyl, alkynyl, aryl, or heteroaryl;
each of Y and Z, independently, is O, S, or NRb, in which Rb is H, alkyl, alkenyl, alkynyl, aryl, heteroaryl, cycloalkyl, cycloalkenyl, heterocycloalkyl, heterocycloalkenyl, cyano, or NO2;
each of R1 and R2, independently, is H, alkyl, alkenyl, alkynyl, aryl, heteroaryl, halo, C(O)ORc, or C(O)NRcRd, in which each of Rc and Rd, independently, is H, alkyl, alkenyl, alkynyl, aryl, heteroaryl, cycloalkyl, cycloalkenyl, heterocycloalkyl, or heterocycloalkenyl;
each of R3 and R4, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;
A is arylene or heteroarylene;
B is O, S, or NRe, in which Re is H, alkyl, alkenyl, or alkynyl;
C is O, S, alkylene, or NRf, in which Rf is H, alkyl, alkenyl, or alkynyl; or B and C, together with the carbon atom to which they are bonded, are heterocycloalkyl or heterocycloalkenyl;
D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl or heteroaryl; and n is 1, 2, 3, or 4.

Please amend claim 26, in column 89, line 39, to read as follows:

Signed and Sealed this
Nineteenth Day of February, 2013

Teresa Stanek Rea
*Acting Director of the United States Patent and Trademark Office*

A compound of formula (I):

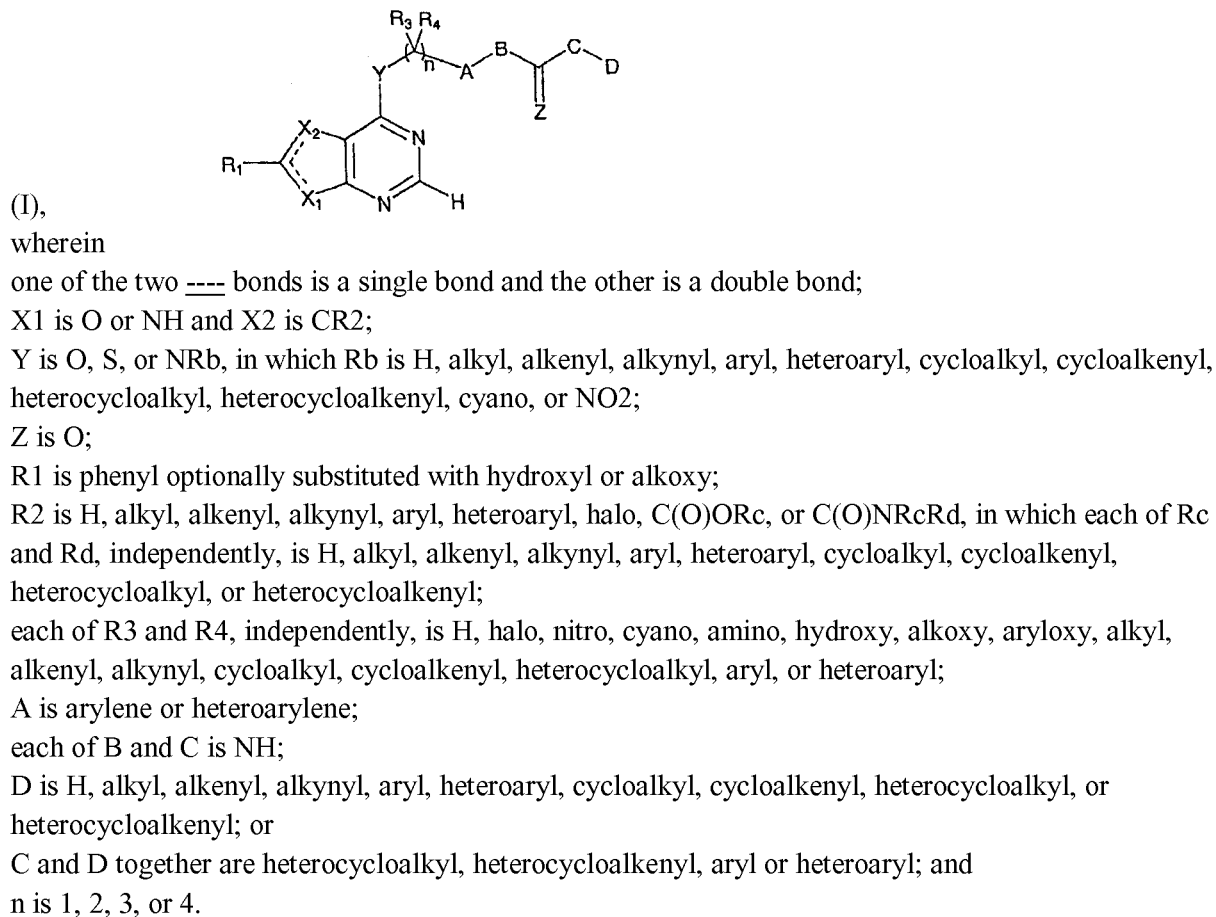

(I),
wherein
one of the two ---- bonds is a single bond and the other is a double bond;
X1 is O or NH and X2 is CR2;
Y is O, S, or NRb, in which Rb is H, alkyl, alkenyl, alkynyl, aryl, heteroaryl, cycloalkyl, cycloalkenyl, heterocycloalkyl, heterocycloalkenyl, cyano, or NO2;
Z is O;
R1 is phenyl optionally substituted with hydroxyl or alkoxy;
R2 is H, alkyl, alkenyl, alkynyl, aryl, heteroaryl, halo, C(O)ORc, or C(O)NRcRd, in which each of Rc and Rd, independently, is H, alkyl, alkenyl, alkynyl, aryl, heteroaryl, cycloalkyl, cycloalkenyl, heterocycloalkyl, or heterocycloalkenyl;
each of R3 and R4, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;
A is arylene or heteroarylene;
each of B and C is NH;
D is H, alkyl, alkenyl, alkynyl, aryl, heteroaryl, cycloalkyl, cycloalkenyl, heterocycloalkyl, or heterocycloalkenyl; or
C and D together are heterocycloalkyl, heterocycloalkenyl, aryl or heteroaryl; and
n is 1, 2, 3, or 4.